US012152054B2

(12) United States Patent
Liu et al.

(10) Patent No.: US 12,152,054 B2
(45) Date of Patent: Nov. 26, 2024

(54) METHODS OF PURIFYING POLYPEPTIDES

(71) Applicant: Genentech, Inc., South San Francisco, CA (US)

(72) Inventors: Hui F. Liu, Oceanside, CA (US); Brian David Kelley, Burlingame, CA (US); Deanna E. Myers, Encinitas, CA (US); Beth McCooey, Oceanside, CA (US); Krista Marie Petty, San Jose, CA (US)

(73) Assignee: Genentech, Inc., South San Francisco, CA (US)

( * ) Notice: Subject to any disclaimer, the term of this patent is extended or adjusted under 35 U.S.C. 154(b) by 157 days.

(21) Appl. No.: 17/369,765

(22) Filed: Jul. 7, 2021

(65) Prior Publication Data

US 2022/0064209 A1 Mar. 3, 2022

Related U.S. Application Data

(63) Continuation of application No. 16/749,888, filed on Jan. 22, 2020, now abandoned, which is a continuation of application No. 16/167,364, filed on Oct. 22, 2018, now abandoned, which is a continuation of application No. 13/682,620, filed on Nov. 20, 2012, now abandoned, which is a continuation of application No. PCT/US2011/037977, filed on May 25, 2011.

(60) Provisional application No. 61/348,143, filed on May 25, 2010.

(51) Int. Cl.
*C07K 1/18* (2006.01)
*B01D 15/36* (2006.01)
*B01D 15/38* (2006.01)
*C07K 1/16* (2006.01)
*G01N 30/88* (2006.01)

(52) U.S. Cl.
CPC .............. *C07K 1/18* (2013.01); *B01D 15/362* (2013.01); *B01D 15/3847* (2013.01); *C07K 1/165* (2013.01); *G01N 2030/8831* (2013.01)

(58) Field of Classification Search
None
See application file for complete search history.

(56) References Cited

U.S. PATENT DOCUMENTS

| 4,399,216 A | 8/1983 | Axel |
| 4,419,446 A | 12/1983 | Howley et al. |
| 4,601,978 A | 7/1986 | Karia |
| 4,676,980 A | 6/1987 | Segal et al. |
| 4,704,362 A | 11/1987 | Itakura |
| 4,816,567 A | 3/1989 | Cabilly |
| 4,965,199 A | 10/1990 | Capon et al. |
| 5,208,020 A | 5/1993 | Chari |
| 5,229,275 A | 7/1993 | Goroff |
| 5,500,362 A | 3/1996 | Robinson |
| 5,534,615 A | 7/1996 | Baker |
| 5,545,328 A | 8/1996 | Pliura |
| 5,545,807 A | 8/1996 | Surani et al. |
| 5,565,332 A | 10/1996 | Hoogenboom |
| 5,567,610 A | 10/1996 | Borrebaeck |
| 5,571,894 A | 11/1996 | Wels |
| 5,573,905 A | 11/1996 | Lerner |
| 5,587,458 A | 12/1996 | King |
| 5,589,369 A | 12/1996 | Seidman |
| 5,591,669 A | 1/1997 | Krimpenfort |
| 5,591,828 A | 1/1997 | Bosslet |
| 5,693,780 A | 12/1997 | Newman |
| 5,712,374 A | 1/1998 | Kuntsmann |
| 5,731,168 A | 3/1998 | Carter |
| 5,736,137 A | 4/1998 | Anderson et al. |
| 5,821,337 A | 10/1998 | Carter |
| 5,840,523 A | 11/1998 | Simmons et al. |
| 6,703,018 B2 | 3/2004 | Jardieu |
| 7,169,901 B2 | 1/2007 | Baca |
| 7,521,541 B2 | 4/2009 | Eigenbrot |
| 2006/0067930 A1 | 3/2006 | Adams |
| 2009/0050566 A1 | 2/2009 | Kozlov |
| 2009/0105465 A1 | 4/2009 | Arunakumari |
| 2009/0148435 A1 | 6/2009 | Lebreton |
| 2011/0065901 A1 | 3/2011 | Soice |
| 2012/0148576 A1* | 6/2012 | Sharma ............ A61K 39/39591 424/133.1 |
| 2012/0178910 A1* | 7/2012 | Arunakumari ........... C07K 1/18 530/416 |

(Continued)

FOREIGN PATENT DOCUMENTS

| CN | 1114836 A | 1/1996 |
| CN | 1299370 A | 6/2001 |

(Continued)

OTHER PUBLICATIONS

Anonymous "Ion Exchange Chromatography Using Fractogel EMD and Fractoprep Tentacle Media" Product Brochure, EMD Chemicals, Inc. (Year: 2005).*
Brown et al. "Overloading ion-exchange membranes as a purification step for monoclonal antibodies" Biotechnol. Appl. Biochem. 56:59-70. (Year: 2010).*
Aebi, H. (1982). Introduction to Practical Biochemistry, Karger, Basel, pp. 68-71, 6 pages. (With English Translation).
Alberts, B. et al. (2002). Molecular Biology of The Cell, 4th Ed. Garland Science pp. 481-484, 6 pages.
Amersham Bio-Sciences Handbook. (2001). "Protein Purification," 7 pages.

(Continued)

Primary Examiner — Sudhakar Katakam
Assistant Examiner — Zachary J Miknis
(74) Attorney, Agent, or Firm — Morrison & Foerster LLP

(57) ABSTRACT

The present invention provides methods for purifying a polypeptide from a composition comprising the polypeptide and at least one contaminant and formulations comprising the polypeptide purified by the methods. The methods for purifying include cation exchange material and/or mixed mode material.

27 Claims, 30 Drawing Sheets

(56) References Cited

U.S. PATENT DOCUMENTS

2020/0399307 A1  12/2020  Liu et al.

FOREIGN PATENT DOCUMENTS

| | | |
|---|---|---|
| CN | 1496993 A | 5/2004 |
| EP | 0073657 A1 | 3/1983 |
| EP | 0308936 B1 | 3/1989 |
| EP | 0402226 A1 | 12/1990 |
| EP | 0404097 A2 | 12/1990 |
| EP | 2360183 A1 | 8/2011 |
| JP | 2008501712 A | 1/2008 |
| WO | 198905859 A1 | 6/1989 |
| WO | 1991000360 A1 | 1/1991 |
| WO | 199220373 A1 | 11/1992 |
| WO | 199308829 A1 | 5/1993 |
| WO | 199311161 A1 | 6/1993 |
| WO | 199316185 A2 | 8/1993 |
| WO | 199411026 A2 | 5/1994 |
| WO | 199411026 C1 | 5/1994 |
| WO | 199411026 A3 | 8/1994 |
| WO | 1995008574 | 3/1995 |
| WO | 199727757 A1 | 8/1997 |
| WO | 199957134 A1 | 11/1999 |
| WO | 2003097692 A1 | 11/2003 |
| WO | 2003102132 A2 | 12/2003 |
| WO | 2005117978 A2 | 12/2005 |
| WO | 2006043895 A1 | 4/2006 |
| WO | WO-2006099308 A2 * | 9/2006 ............. B01D 15/30 |
| WO | 2006110277 A1 | 10/2006 |
| WO | 2006116064 A2 | 11/2006 |
| WO | 2008086335 A2 | 7/2008 |
| WO | 2008086335 A3 | 10/2008 |
| WO | 2008145351 A1 | 12/2008 |
| WO | WO-2009058812 A1 * | 5/2009 ............. A61P 19/02 |
| WO | 2009126603 A1 | 10/2009 |
| WO | 2010019148 A1 | 2/2010 |
| WO | 2011035282 A1 | 3/2011 |
| WO | 2012068134 A1 | 5/2012 |

OTHER PUBLICATIONS

Amersham Bio-Sciences Handbook. (2002). "Antibody Purification", Chapter 5 and excerpt of chapter 4, pp. 39-44 and 55-69.

Amersham Bio-Sciences Handbook. (2004). "Ion Exchange Chromatography & Chromatofocusing," Chapter 1 pp. 11, 18, and 35, 6 pages.

Anonymous. (May 2005). "Ion Exchange Chromatography Using Fractogel EMO and Fractoprep Tentacle Media" EMO Chemicals, Inc., 8 pages.

Ashkenazi, A et al. (1995) "Immunoadhesins: An Alternative to Human Monoclonal Antibodies," Methods: A Companion to Methods in Enzymology 8:104-115.

Atoll GmbH Atoll MediaScout catalogue 2008, pp. 6, downloaded from http://www.chromate.co.kr/download/old/1_MediaScout_Catalogue.pdf.

Brennan, M. et al. (Jul. 5, 1985). "Preparation of Bispecific Antibodies by Chemical Recombination of Monoclonal Immunoglobulin G1 Fragments," Science 229:81-83.

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brown, A. et al. (2010). "Overloading Ion-Exchange Membranes as a Purification Step for Monoclonal Antibodies," Biotechnol. App. Biochem. 56:59-70.

Brüggermann, M. et al. (1993). "Designer Mice: The Production Of Human Antibody Repertoires In Transgenic Animals," Year Immunology 7:33-40.

Capel, P.J. et al. (Feb. 1994). "Heterogeneity of Human IgG Fc Receptors," Immunomethods 4(1):25-34.

Caron, P.C. et al. (Oct. 1, 1992). "Engineering Humanized Dimeric Forms of IgG Are More Effective Antibodies," J. Exp Med. 176:1191-1195.

Carter, P. et al. (Feb. 1992). "High Level *Escherichia coli* Expression and Production of a Bivalent Humanized Antibody Fragment," Bio/Technology 10:163-167.

Carter, P. et al. (May 1992). "Humanization of an Anti-p185HER2 Antibody for Human Cancer Therapy," Proc. Natl. Acad. Sci. USA 89:4285-4289.

Chen, J. et al. (2010, e-pub. Sep. 23, 2009) "The Distinctive Separation Attributes of Mixed-Mode Resins and Their Application in Monoclonal Antibody Downstream Purification Process," Journal of Chromatography A, 1217 (2):216-224.

Chothia, C. et al. (Aug. 20, 1987). "Canonical Structures for the Hypervariable Regions of Immunoglobulins," J. Mol. Biol. 196(4):901-917.

Chung, W.K. et al. (Jan. 8, 2010, e-pub. Aug. 7, 2009). "Investigation of Protein Binding Affinity in Multimodal Chromatographic Systems Using a Homologous Protein Library," J Chromatography A 1217:191-198.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Communication from Mewburn Ellis, to the European Patent Office, for European Patent Application No. 11787363.8, mailed on Aug. 13, 2018, for Proprietor F. Hoffmann-La Roche AG, Opponent Bayer Intellectual Property GmbH, 33 pages.

Cunningham, B.C. et al. (Jun. 2, 1989). "High-Resolution Epitope Mapping of hGH-Receptor Interactions by Alanine-Scanning Mutagenesis," Science 24:1081-1085.

Daeron, M. (1997). "Fc Receptor Biology," Ann. Rev. Immunol. 15:203-234.

De Haas, M. et al. (1995). 'Fcγ Receptors of Phagocytes, J. Lab. Clin. Med. 126(4):330-341.

EMD Chemicals Inc."Ion Exchange Chromatography Using FRACTOGEL EMD and FRACTOPREP Tentacle Media" Product Brochure. EMD Biosciences. Accessed on the Internet Apr. 22, 2013 athttp:/ /85.238.144.1 8/lifescience/literatu re/Using Em D Ion Exchange Bioch rom a tog raphy Media. pdf, 8 pages.

Eriksson, K. et al. (Feb. 2009). "MAb Contaminant Removal with a Multimodal Anion Exchanger. A Platform Step to Follow Protein A," BioProcess International 7(2):52-56.

European Opposition Dated Jan. 30, 2020, Opponent: Bayer Intellectual Property GmbH, Patent Proprietor: F. Hoffmann-La Roche Ag, for European Patent No. 2575847, 9 pages.

Facts and Submission for European Opposition mailed on Jan. 3, 2019, for European Patent Application No. 11787363.8, to the European Patent Office for Opposition, 12 pages.

Fahrner, R.L. et al. (2001, e-pub. Apr. 15, 2018). "Industrial Purification of Pharmaceutical Antibodies: Development, Operation, and Validation of Chromatography Processes," Biotechnol. Genet. Eng. Rev. 18:301-327.

Fleer, R. et al. (Oct. 1, 1991). "Stable Multicopy Vectors for High-Level Secretion of Recombinant Human Serum Albumin by Kluyveromyces Yeasts," Bio/Technology 9(10):968-975.

Gagnon, P. (2009). "Chapter 6: Purification of Monoclonal Antibodies By Mixed-Mode Chromatorgraphy," in Process Scale Purification of Antibodies, John Wiley & Sons, Inc., pp. 125-143.

Gagnon, P. et al. (Feb. 2010). "Minibodies and Multimodal Chromatography Methods: A Convergence of Challenge and Opportunity," Bioprocess Int. 8(2):26-35, 21 pages.

Gallus Immunotech Inc. Printout of the webpage http://gallusimmunotech.com/about-igy/comparison-of-igg-ige-igy-and-igy-deltafc.html, including WayBackmaschine printout, published on Aug. 4, 2014, 5 pages.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

GE Healthcare Bio-Sciences Handbook. (2010). "Strategies for Protein Purification," Chapters 2, 4 and 5, pp. 17-29 and 39-56.

GE Healthcare. (2007). "Selective Removal of Aggregates With Capto Adhere, Application Note 28-9078-93 AA, process-Scale Antibody Purification," GE Healthcare, 6 pages.

(56) References Cited

OTHER PUBLICATIONS

Goding, J.W. (1986). Monoclonal Antibodies: Principles and Practice, pp. 59-103.
Gopal, A.K. et al. (Aug. 1, 2008, e-pub. May 23, 2008). "Rituximab Blocks Binding of Radiolabeled Anti-CD20 Antibodies (Ab) but not Radiolabled Anti-CD45Ab" Blood 112(3):830-835.
Gottschalk, U. (2008). "Bioseparation in Antibody Manufacturing: The Good, The Bad, and the Ugly," Biotechnol. Prog. 24(3):496-503.
Graham, F.L. et al. (Apr. 1973). "A New Technique for the Assay of Infectivity of Human Adenovirus 5 DNA," Virology 52(2):456-467.
Griffiths, A.D. et al. (1993). "Human Anti-Self Antibodies with High Specificity from Phage Display Libraries," EMBO J. 12(2):725-734.
Gruber, M. et al. (1994). "Efficient Tumor Cell Lysis Mediated by a Bispecific Single Chain Antibody Expressed in *Escherichia coli*," J. Immunol. 152:5368-5374.
Guyer, R.L. et al. (Aug. 1976). "Immunoglobulin Binding By Mouse Intestinal Epithelial Cell Receptors," J. Immunol. 117(2):587-593.
Hahn, B.H. et al. (Dec. 1984). "A Public Idiotypic Determinant is Present on Spontaneous Cationic IgG Antibodies to DNA From Mice of Unrelated Lupus-Prone Strains" J. Immunol. 133(6):3015-3019.
Hardin, A.-M. et al. (May 15, 2009). "Ion exchange Chromatography Of Monoclonal Antibodies: Effect Of Resin Ligand Density On Dynamic Binding Capacity," Journal of Chromatography A, 1216(20):4366-4371, 14 pages.
Harinarayan, C. et al. (Dec. 5, 2006, e-pub. Aug. 8, 2006). "An Exclusion Mechanism in Ion Exchange Chromatography," Biotechnology and Bioengineering 95(5):775-787.
Hendy, S. et al. (1999). "Rapid Production of Single Chain Fv Fragments in Plants Using a Potato Virus X Episomal Vector," J. Immunol. Methods 231:137-146.
Hiller, K. (1999/2000).Dictionary of Biochemistry, Lexikon Der Biochemie Elsevier, pp. 197-198, 9 pages. with English Translation.
Holliger, P. et al. (Jul. 1993). "Diabodies": Small Bivalent and Bispecific Antibody Fragments, Proceedings of the National Academy of Sciences USA 90:6444-6448.
Holm, J. et al. (Jun./Aug. 2002). "A Combination Of Cation Exchange And Ligand-Affinity Chromatography For Purification of Two Molecular Species Of The Folate Binding Protein In Human Milk, One Equipped With A Hydrophobic Glycosyl Phosphatidylinositol Tail: Characterization Of Hydrophobicity And Electrical Charge," Biosci. Rep. 22(3-4):443-454.
Holtzhauer, M., et al. (1995). Biochemical Laboratory Methods, Springer, Second Revised Edition, pp. 12-14,110-117. With English Translation.
Hou, Y. et al. (2008). "Progress in Technology of Antibody Purification and Separation," Biotechnology Bulletin 3:60-62.
Hsiao, C.L. et al. (Aug. 1979). "High-Frequency Transformation of Yeast by Plasmids Containing the Cloned Yeast ARG4 Gene," Proc. Natl. Acad. Sci. (USA) 76(8):3829-3833.
International Preliminary Report on Patent Ability issued on Nov. 27, 2012, for PCT Application No. PCT/US2011/037977, filed on May 25, 2011, 6 pages.
International Search Report mailed on Oct. 28, 2011, for PCT Application No. PCT/US2011/037977, filed on May 25, 2011, 3 pages.
International Search Report mailed on Oct. 28, 2011, for PCT Application No. PCT/US2011/37977, filed on May 25, 2011, 2 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Johnson, K.S. et al. (1993). "Human Antibody Engineering," Current Opinion in Structural Biology 3:564-571.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest (Table of Contents and Introduction), 5th edition, Bethesda, MD: Public Health Service, NIH, vol. 1, 21 pages.
Keown, W.A. et al. (1990). "Methods for Introducing DNA into Mammalian Cells," Methods in Enzymology 185:527-537.
Kim, J-K. et al. (1994). "Localization of the Site of the Murine IgGI Molecule That is Involved in Binding to the Murine Intestinal Fc Receptor," Eur. J. Immunol. 24:2429-2434.
Kleber, H.-P. (1988). Biochemical Practical Work, 3rd Edition, Gustav Fischer Verlag, pp. 139-141, 10 pages. With English Translation.
Kohler, G. et al. (Aug. 7, 1975) "Continuous Cultures Of Fused Cells Secreting Antibody Of Predefined Specificity," Nature 256:495-497.
Kostelny, S.A. et al. (Mar. 1, 1992). "Formation of a Bispecific Antibody By The Use of Leucine Zippers," J. Immunol. 148(5):1547-1553.
Kozbor, D. et al. (Dec. 1984). "A Human Hybrid Myeloma for Production of Human Monoclonal Antibodies," J. Immunol. 133(6):3001-3005.
Larrick, J.W. et al. (Jul. 1998). "Production of Antibodies in Transgenic Plants" Res. Immunol. 149(6):603-608.
Lehniger, A.L. (1975). "The Amino Acid Building Blocks of Proteins," Chapter 4 in Biochemistry, second ed., Worth Publishers, New York, pp. 73-75.
Lenhoff, A. M. et al. (Dec. 9, 2011). "Protein Adsorption and Transport in Polymer-Functionalized Ion-Exchangers," Journal of Chromatography A 1218(49):8748-8759, 24 pages.
Liu, H.F. et al. (2011, e-pub. Aug. 12, 2011). "Exploration of Overloaded Cation Exchange Chromatography for Monoclonal Antibody Purification," J. Chromatogr. A 1218(39):6943-6952.
Mansour, S.L. et al. (Nov. 24, 1988). "Disruption of the Proto-Oncogene Int-2 in Mouse Embryo-Derived Stem Cells: A General Strategy For Targeting Mutations to Non-Selectable Genes," Nature 336:348-352.
Marks, J.D. et al. (1991). "By-Passing Immunization. Human Antibodies From V-Gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
Merrifield, R. B. (Jul. 20, 1963). "Solid Phase Peptide Synthesis. I. The Synthesis of a Tetrapeptide," J. Am. Chem. Soc. 85:2149-2154.
Mhatre, R. et al. (1995). "Purification of Antibody Fab Fragments by Cation-Exchange Chromatography and pH Gradient Elution," Journal of Chromatography A 707:225-231.
Milstein, C. et al. (Oct. 6, 1983) "Hybrid Hybridomas and their use in Immunohistochemistry," Nature 305:537-540.
Moore, A. et al. (1995). "Apoptosis in CHO Cell Batch Cultures: Examination by Flow Cytometry" Cytotechnology 17:1-11.
Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Munson, P.J. et al. (1980). "Ligand: A Versatile Computerized Approach for Characterization of Ligand-Binding Systems," Anal. Biochem. 107:220-239.
Niu, L., et al. (May 2011). "Preparative Isolation Of Alkaloids From Corydalis bungeana Turcz. by High-Speed Counter-Current Chromatography Using Stepwise Elution," Journal of Separation Science 34(9):987-994, 13 pages.

(56) References Cited

OTHER PUBLICATIONS

Notice of Opposition mailed on Mar. 3, 2018, for European Patent Application No. 11787363.8, filed on May 25, 2011, Opponent Bayer Intellectual Property GmbH, Proprietor F. Hoffmann-La Roche AG, 38 pages.
Plückthun, A. (1992). "Mono- and Bivalent Antibody Fragments Produced in *Escherichia coli*: Engineering, Folding and Antigen Binding," Immunol. Revs. 130:151-188.
Plückthun, A. (1994) "Antibodies from *Escherichia coli*," Chapter 11 in Handbook of Experimental Pharmacology 113:269-315.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151 (5):2623-2632.
Price, N. C. et al. (1989). Fundamentals of Enzymology, 2nd Ed. Oxford University Press, 2nd Edition, pp. 23-25.
Qu, J.-B. et al. (2009, e-pub. Aug. 3, 2009) "A Novel Stationary Phase Derivatized From Hydrophilic Gigaporous Polystyrene-Based Microspheres For High-Speed Protein Chromatography," Journal of Chromatography A, 1216 (37):6511-6516.
Ravetch, J.V. et al. (1991). "Fc Receptors," Annu. Rev. Immunol. 9:457-492.
Reyes, G.R. et al. (Jun. 17, 1982) "Expression of Human ß-interferon cDNA Under the Control of a Thymidine Kinase Promoter from Herpes Simplex Virus," Nature 297:598-601.
Riechmann, L. et al. (Mar. 24, 1988). "Reshaping Human Antibodies for Therapy," Nature 332:323-327.
Shaw, C.H. et.al. (Sep. 1983). "A General Method for the Transfer of Cloned Genes to Plant Cells," Gene 23 (3):315-330.
Shopes, B. et al. (May 1, 1992). "A Genetically Engineered Human IgG Mutant With Enhanced Cytolytic Activity," J. Imniunol. 148:2918-2922.
Sims, M.J. et al. (Aug. 15, 1993). "A Humanized CD18 Antibody Can Block Function Without Cell Destruction," J. Immunol. 151(4):2296-2308.
Skerra, A. (1993). "Bacterial Expression of Immunoglobulin Fragments," Curr. Opinion in Immunol. 5:256-262.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Stinchcomb, D.T. et al. (Nov. 1, 1979). "Isolation and Characterisation of a Yeast Chromosomal Replicator," Nature 282:39-43.
Suresh, M.R. et al. (1986). "Bispecific Monoclonal Antibodies From Hybrid Hybridomas," Methods in Enzymology 121:210-228, 19 pages.
Traunecker, A. et al. (1991). "Bispecific Single Chain Molecules (Janusins) Target Cytotoxic Lymphocytes on HIV Infected Cells," EMBO J. 10(12):3655-3659.
Tugcu, N. et al. (2008). "Maximizing Productivity of Chromatography Steps for Purification of Monoclonal Antibodies," Biotechnol Bioeng. 99(3):599-613.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Van Den Berg, J.A. et al. (Feb. 1990). "Kluyveromyces as a Host for Heterologous Gene Expression: Expression and Secretion of Prochymosin", Bio/Technology, 8:135-139.
Van Solingen, P. et al. (May 1977). "Fusion of Yeast Spheroplasts,"Journal of Bacteriology 130(2):946-947.
Verhoeyen, M. et al. (Mar. 25, 1988). "Reshaping Human Antibodies: Grafting an Antilysozyme Activity," Science 239:1534-1536.
Vitetta, E.S. et al. (Nov. 20, 1987). "Redesigning Nature's Poisons to Create Anti-Tumor Reagents," Science 238:1098-1104.
Waterhouse, P. et al. (1993). "Combinatorial Infection and in Vivo Recombination: a Strategy for Making Large Phage Antibody Repertoires," Nucl. Acids Res. 21(9):2265-2266.
Wikipedia Definition "Chromatography," retrieved from https://web.archive.org/web/20100118233155/https:/en.wikipedia.org/wiki/Chromatography, last visited Nov. 7, 2018, 15 pages.
Wikipedia Definition "High-Performance Liquid Chromatorgraphy," retrieved from https://web.archive.org/web/20100616034602/https:/en.wikipedia.org/wiki/High-perf . . . , last visited Jan. 8, 2018, 18 pages.
Wikipedia Definition "Partition Coefficeint," retrieved from https://web.archive.org/web/20111011193624/http:/en.wikipedia.org/wiki/Partition_c . . . , last visited Nov. 7, 2018, 12 pages.
Wolff, E.A et al. (Jun. 1, 1993). "Monoclonal Antibody Homodimers: Enhanced Antitumor Activity in Nude Mice," Can Res 53:2560-2565.
Written Opinion mailed on Oct. 28, 2011, for PCT Application No. PCT/US2011/037977, filed on May 25, 2011, 5 pages.
Yang, C. et al. (Aug. 2007). Bioseparation Technology, Beijing, China Agriculture Press, 4 pages.
Yaniv, M. (May 6, 1982). "Enhancing Elements for Activation of Eukaryotic Promoters," Nature 297:17-18.
Decision to Maintain the European Patent in Amended Form (Art. 101(3)(a)EPC), dated Mar. 31, 2022, for European Patent No. 2575847, 1 page.
European Opposition Communication Dated Jul. 16, 2021, Opponent: Bayer Intellectual Property GmbH, Patent Proprietor. F. Hoffmann-La Roche Ag, for European Patent No. 2575847, 18 pages.
European Opposition Pursuant to Rule 82(2) EPC, dated Jan. 25, 2022, for European Patent No. 2575847, 4 pages.
Interlocutory Decision in Opposition Proceedings Dated Oct. 11, 2021, for European Patent No. 2575847, 228 pages.
Termination of European Opposition Proceedings dated Mar. 25, 2022, for European Patent No. 2575847, 1 page.

\* cited by examiner

FIG. 6C

| Sample ID | Anti-CD11a Collected (g/L CV) | HMW% |
|---|---|---|
| Load | - | 4.83 |
| 2 | 2.20 | n.a. |
| 4 | 40.9 | 0.05 |
| 6 | 109 | 0.10 |
| 8 | 179 | 0.32 |
| 10 | 250 | 0.85 |
| 15 | 424 | 1.89 |
| 20 | 597 | 2.49 |
| 24 | 681 | 2.76 |
| Strip | - | 35.3 |

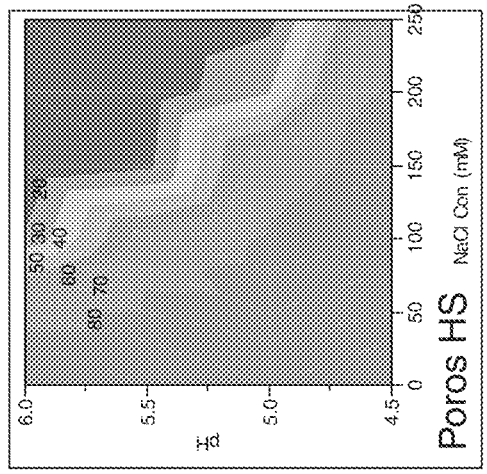

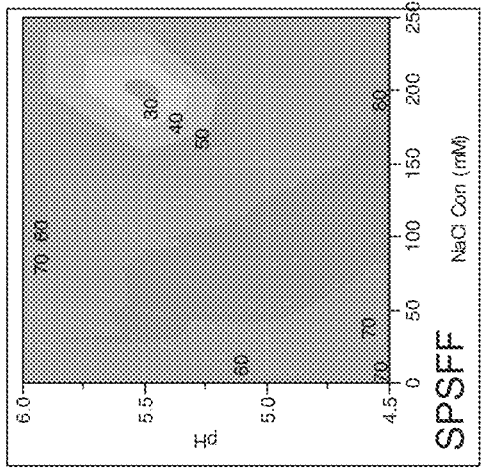
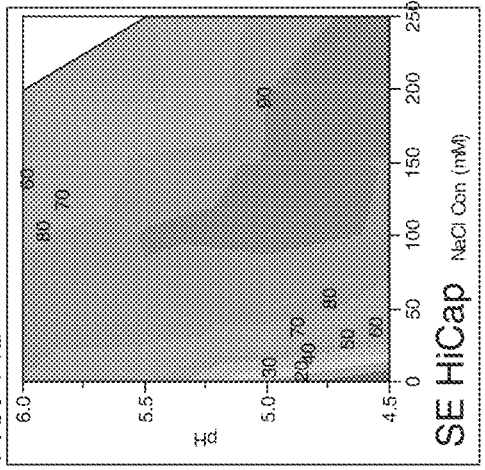
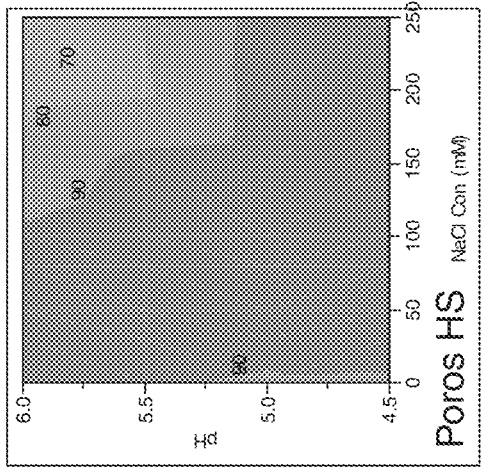
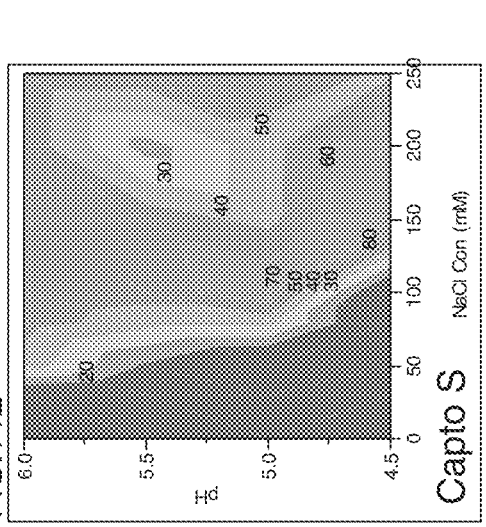
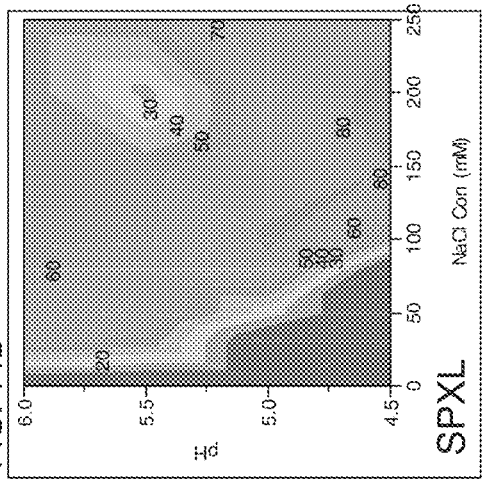

X-axis: run time

X-axis: Antibody Load Amount

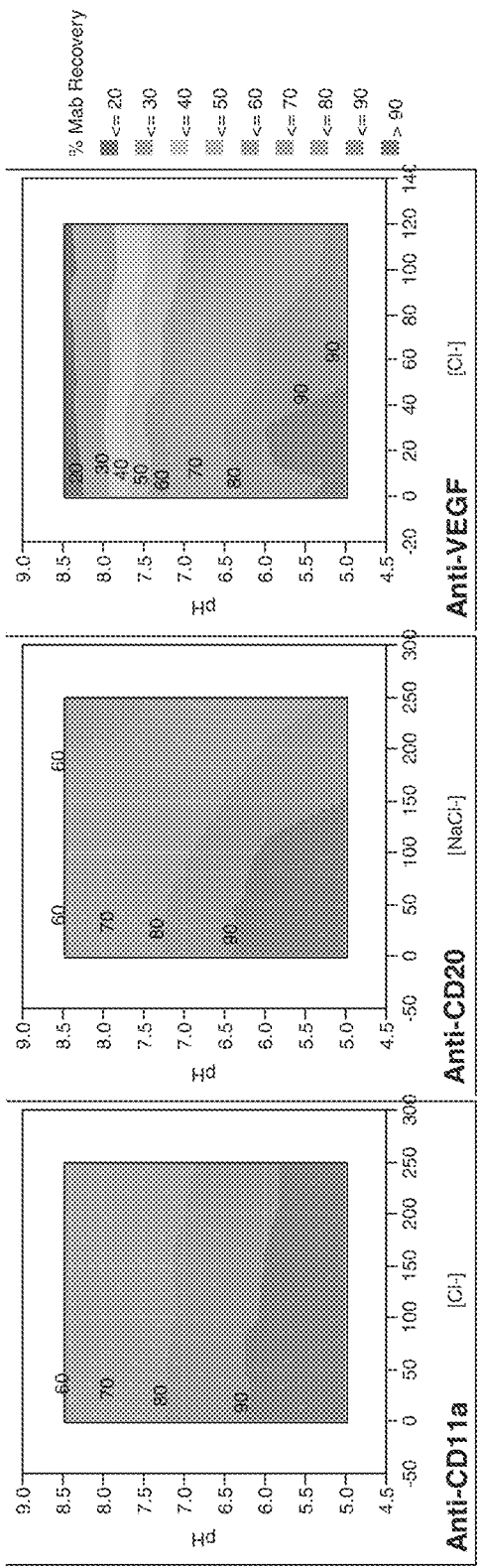

NaAc as buffering salt
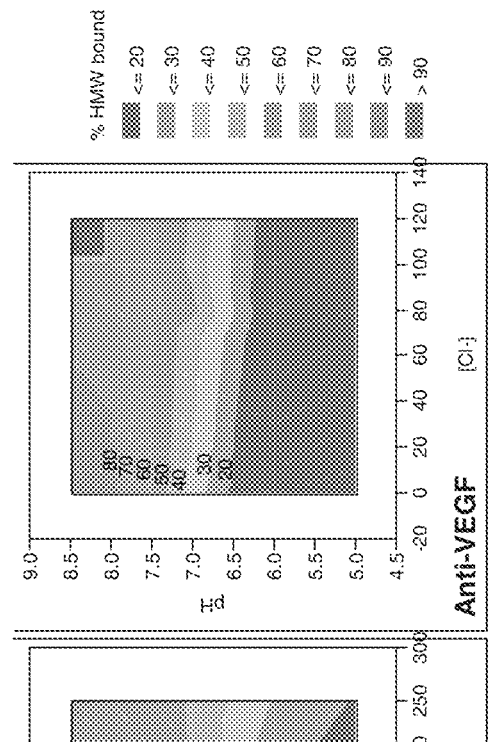
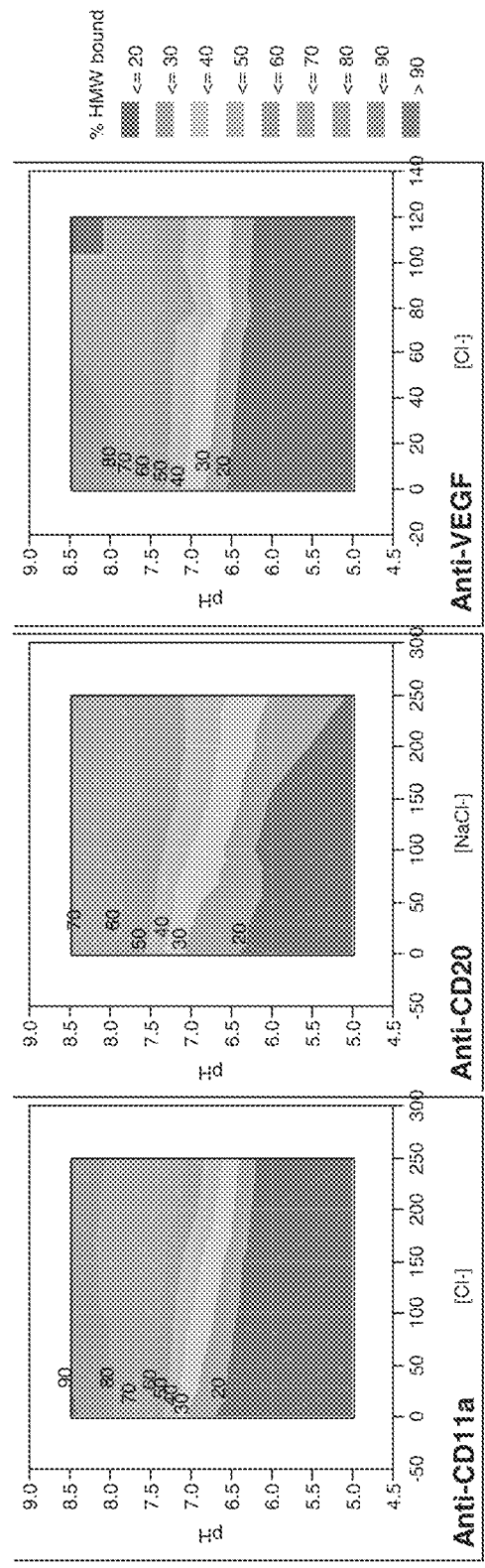
Glycine HCl as buffering salt
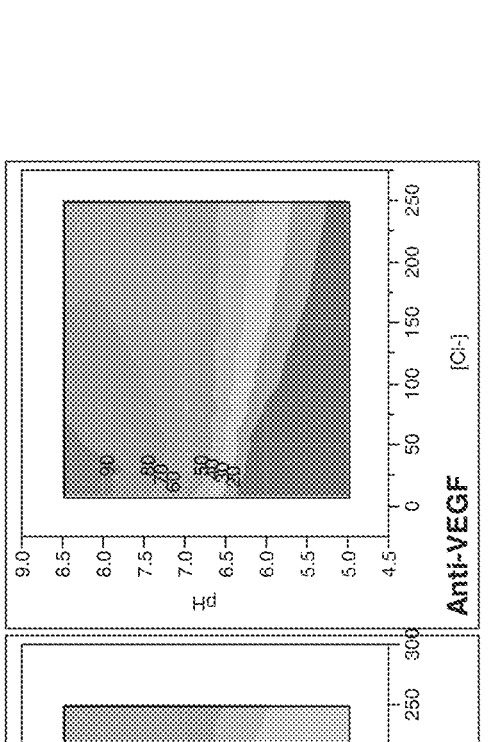
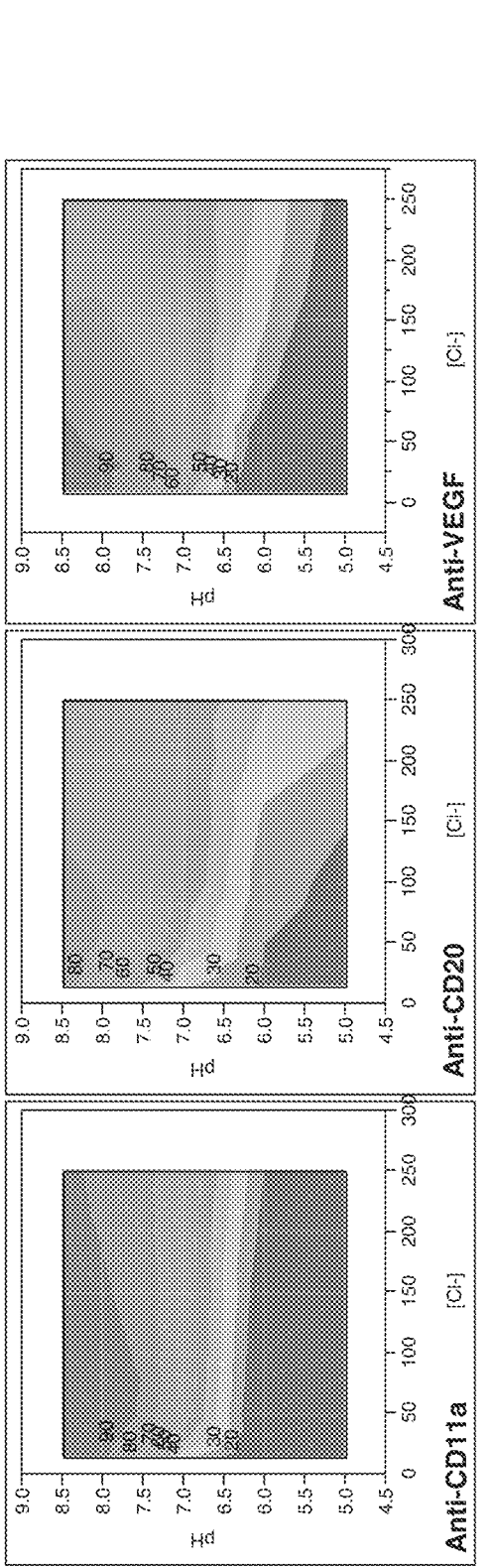

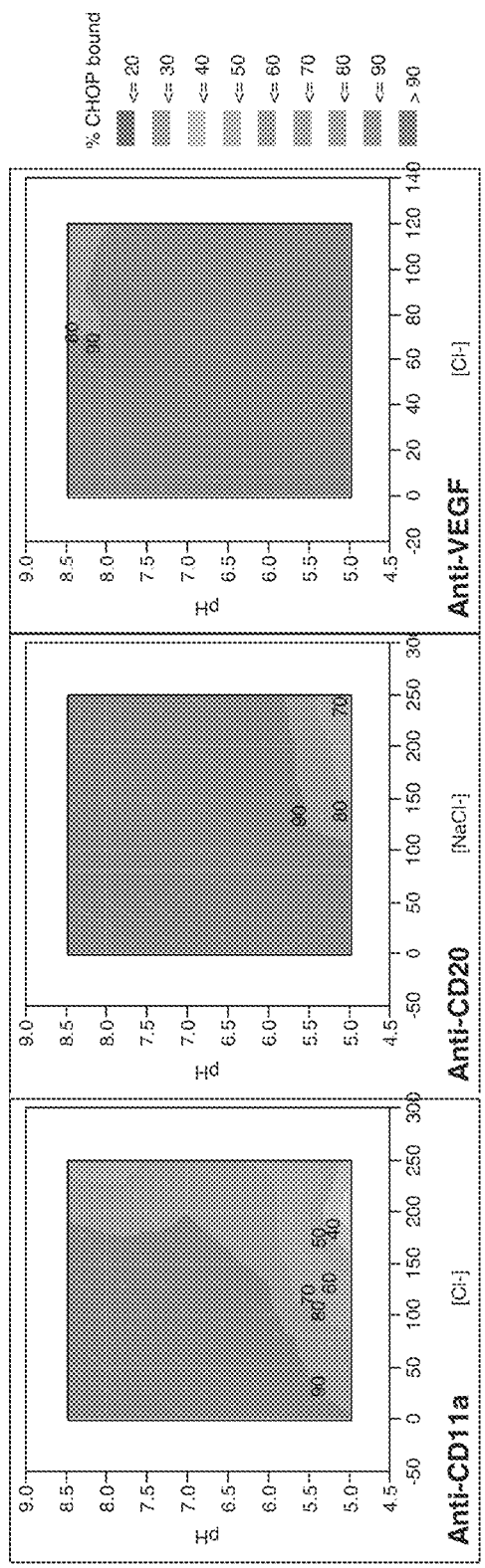
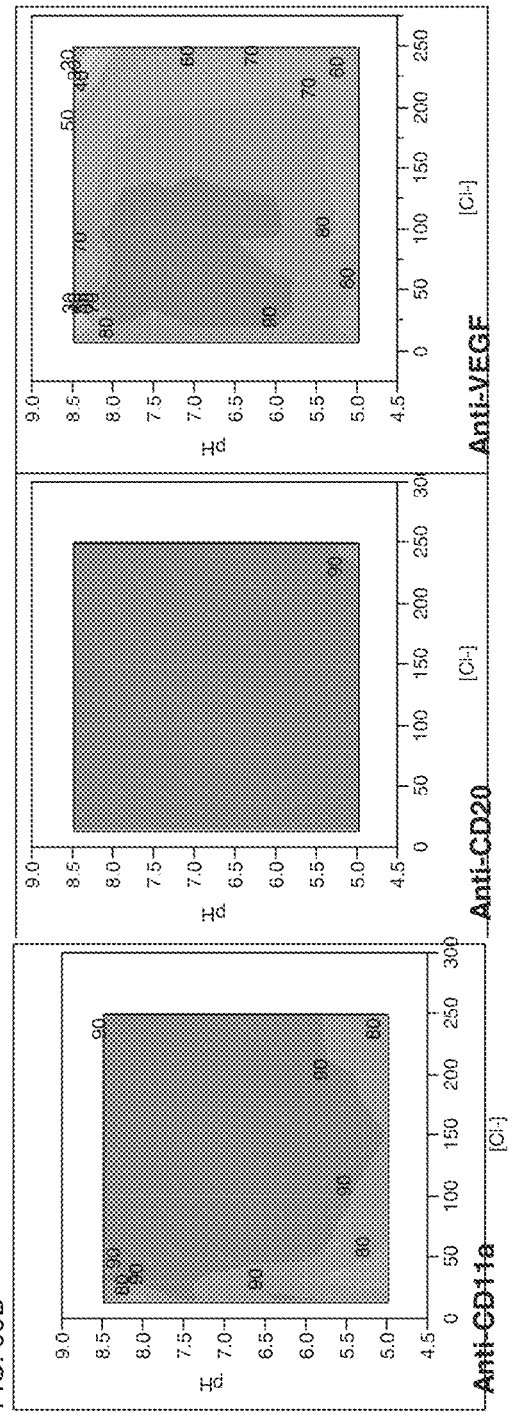

METHODS OF PURIFYING POLYPEPTIDES

CROSS-REFERENCE TO RELATED APPLICATIONS

This application is a continuation of U.S. patent application Ser. No. 16/749,888, filed on Jan. 22, 2020, which is a continuation of U.S. patent application Ser. No. 16/167,364, filed on Oct. 22, 2018, now Abandoned, which is a continuation of U.S. patent application Ser. No. 13/682,620, filed on Nov. 20, 2012, now Abandoned, which is a continuation of International Patent Application No. PCT/US2011/037977, filed May 25, 2011, which claims priority benefit to U.S. Provisional Patent Application No. 61/348,143 filed May 25, 2010, the content of each of which is hereby incorporated herein by reference in its entirety.

FIELD OF THE INVENTION

The present invention provides methods for purifying a polypeptide from a composition comprising the polypeptide and at least one contaminant and formulations comprising the polypeptide purified by the methods.

BACKGROUND OF THE INVENTION

The large-scale, economic purification of polypeptides is increasingly an important problem for the biotechnology industry. Generally, polypeptides are produced by cell culture, using either mammalian or bacterial cell lines engineered to produce the polypeptide of interest by insertion of a recombinant plasmid containing the gene for that polypeptide. Since the cell lines used are living organisms, they must be fed with a complex growth medium, containing sugars, amino acids, and growth factors, usually supplied from preparations of animal serum. It is desirable to separate the polypeptide of interest from a mixture of compounds fed to the cells and from the by-products of the cells themselves.

The separation of the polypeptide of interest from other products produced by the cell is usually attempted using a combination of different chromatography techniques. These techniques separate mixtures of polypeptides on the basis of their charge, degree of hydrophobicity, size, or the specific interaction between the polypeptide of interest and an immobilized capture agent. Several different chromatography resins are available for each of these techniques, allowing accurate tailoring of the purification scheme to the particular polypeptide involved. The essence of each of these separation methods is that polypeptides can be caused either to move at different rates down a long column, achieving a physical separation that increases as they pass further down the column, or to adhere selectively to the separation medium, being then differentially eluted by different solvents. In some cases, the polypeptide of interest is separated from impurities when the impurities specifically adhere to the column, and the polypeptide of interest does not, that is, the polypeptide of interest is present in the "flow-through."

The large-scale, cost-effective purification of a polypeptide to sufficient purity for use as a human therapeutic remains a formidable challenge.

BRIEF SUMMARY

Provided herein are methods for purifying a polypeptide from a composition comprising the polypeptide and at least one contaminant, wherein the method comprises either (i) or (ii): (i) sequential steps of (a) loading the composition onto a cation exchange material at a loading density of greater than about 150 g/L of cation exchange material; and (b) loading a composition recovered from the cation exchange material onto a mixed mode material; or (ii) sequential steps of (a) loading the composition onto a mixed mode material; and (b) loading a composition recovered from mixed mode material onto a cation exchange material at a loading density of greater than about 150 g/L of cation exchange material.

In some embodiments of any of the methods, the polypeptide has a pI of between about 6 and about 10. In some embodiments, the polypeptide has a pI of between about 7 and about 9.

In some embodiments of any of the methods, the polypeptide is an antibody or an immunoadhesin. In some embodiments, the polypeptide is an immunoadhesin. In some embodiments, the polypeptide is an antibody. In some embodiments, the antibody is a monoclonal antibody. In some embodiments, the monoclonal antibody is a chimeric antibody, humanized antibody, or human antibody. In some embodiments, the monoclonal antibody is an IgG monoclonal antibody. In some embodiments, the antibody is an antigen binding fragment. In some embodiments, the antigen binding fragment is selected from the group consisting of a Fab fragment, a Fab' fragment, a F(ab')$_2$ fragment, a scFv, a Fv, and a diabody.

In some embodiments of any of the methods, the at least one contaminant is any one or more of Chinese Hamster Ovary Protein (CHOP), leached protein A, DNA, aggregated protein, cell culture media component, gentamicin, and viral contaminant.

In some embodiments of any of the methods, the sequential steps in (i) and/or (ii) are continuous. In some embodiments of any of the methods, the sequential steps in (i) and/or (ii) are discontinuous. In some embodiments of any of the methods, the method is (i). In some embodiments of any of the methods, the method is (ii).

In some embodiments of any of the methods, the loading density is between about 150 g/L and about 2000 g/L. In some embodiments, the density is between about 150 g/L and about 1000 g/L. In some embodiments, the density is between about 500 g/L and about 700 g/L In some embodiments of any of the methods, the cation exchange material comprises a carboxylic acid functional group or a sulfonic acid functional group. In some embodiments, the functional group is sulphopropyl, sulfoethyl, sulfoisobutyl, or caboxyl. In some embodiments, the cation exchange material is a membrane, a monolith, or resin particles. In some embodiments, the cation exchange material is a resin. In some embodiments, the cation exchange material is MUSTANG® S (modified hydrophilic pholyethersulfone with sulphonic acid), SARTOBIND® S (cross-linked cellulose matrix with sulphonic acid), SO3 Monolith, S CERAMIC HYPERD® (high capacity hydrogel, polymerized within the gigapores of a rigid ceramic bead), POROS® HS50 cross-linked poly(styrene-divinylbenzene) flow-through particles with a polyhydroxylated polymer functionalized with sulfopropyl groups), POROS® HS20, SP-SEPHAROSE® FAST FLOW (SPSFF) (sulphopropyl immobilized on agarose), SP-SEPHAROSE® XL (sulphopropyl immobilized on agarose) (SPXL), CM SEPHAROSE FAST FLOW™ (carboxymethyl immobilized on agarose) CM, CAPTO S™ (highly cross-linked agarose with sulfonate), FRACTOGEL-SE HICAP™, FRACTOGEL-SO3™ or FRACTOGEL™ COO (synthetic polymer resins). In some embodiments, the cation exchange material is POROS® HS50.

In some embodiments of any of the methods, the mixed mode material comprises functional groups capable of anionic exchange and hydrophobic interactions. In some embodiments, the mixed mode material is CAPTO™-ADHERE (highly cross-linked agarose with N-benzyl-n-methyl ethanolamine) resin, MEP HYPERCEL™ (cellulose matrix with 4-mercapto-ethyl-pyridine) resin, HEA HYPERCEL™ (cellulose matrix with hexylamine) resin, PPA HYPERCEL™ (cellulose matrix with phenylpropylamine) resin, or CHROMASORB™ (Ultra High Molecular Weight Polyethylene with primary amine) membrane. In some embodiments, the mixed mode material is CAPTO™-ADHERE resin.

In some embodiments of any of the methods, the method comprises use of an equilibration buffer, a wash buffer, and/or a loading buffer with the cation exchange material and/or anion exchange material, and the conductivity of the equilibration buffer, the wash buffer, and/or the loading buffer is between about 2 mS/cm to about 25 mS/cm. In some embodiments, the conductivity of the equilibration buffer, the wash buffer, and/or the loading buffer is between about 3 mS/cm and 8 mS/cm.

In some embodiments of any of the methods, the method comprises use of an equilibration buffer, a wash buffer, and/or a loading buffer with the cation exchange material and/or the anion exchange material, and the pH of the equilibration buffer, the wash buffer, and/or the loading buffer is between about 4.5 and about 6.5.

In some embodiments of any of the methods, the equilibration buffer, the wash buffer, and/or the loading buffer with the cation exchange material and/or the anion exchange material are the same. In some embodiments of any of the methods, the equilibration buffer, the wash buffer, and/or the loading buffer with the cation exchange material and/or the anion exchange material are the different.

In some embodiments of any of the methods, the method further comprising subjecting the composition comprising the polypeptide to one or more further purification steps either before or after steps (a) and (b). In some embodiments of any of the methods, the method further comprises recovering the purified polypeptide. In some embodiments of any of the methods, the method further comprises combining the purified polypeptide with a pharmaceutically acceptable carrier.

BRIEF DESCRIPTION OF THE DRAWINGS

FIG. 6C shows HMW % with varying amount of the product comprising anti-CD11a antibody collected (mg/mL) using SPSFF.

FIG. 13A-E show the % HMW bound to the resin (POROS® HS50, SE HiCap, SPSFF, SPXL, and CAPTO S™) using the product comprising anti-CD20 antibody under various pHs and salt concentrations.

FIG. 14A-E show the % CHOP bound to the resin (POROS® HS50, SE HiCap, SPSFF, SPXL, and CAPTO S™) using the product comprising anti-CD20 antibody under various pHs and salt concentrations.

FIG. 31A-F show the % Mab recovery for anti-VEGF antibody (in FT fraction), anti-CD11a antibody, and anti-CD20 antibody, using CAPTO™ ADHERE resin under various pHs and conductivities (with either NaAC or glycine HCl as buffering salt).

FIG. 32A-F show the % HMW bound using CAPTO™ ADHERE resin under various pHs and conductivities (with either NaAC or glycine HCl as buffering salt) for anti-VEGF antibody, anti-CD11a antibody, and anti-CD20 antibody.

FIG. 33A-F show the % CHOP bound using CAPTO™ ADHERE resin under various pHs and conductivities (with either NaAC or glycine HCl as buffering salt) for anti-VEGF antibody, anti-CD11a antibody, and anti-CD20 antibody.

DETAILED DESCRIPTION OF THE INVENTION

I. Definitions

Figure 1A:
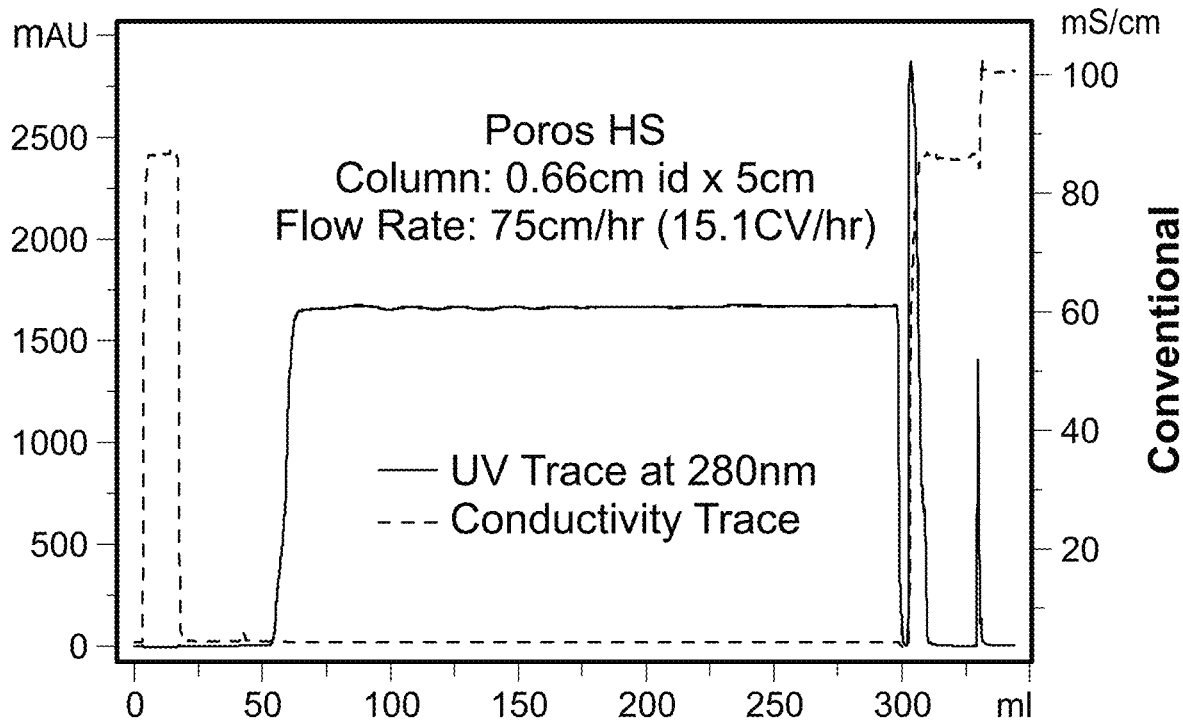
FIG. 1A-D show the chromatograms using POROS® HS50, SPSFF, SO3 Monolith, and MUSTANG® S for the purification of anti-CD11a antibody.
Figure 1B:
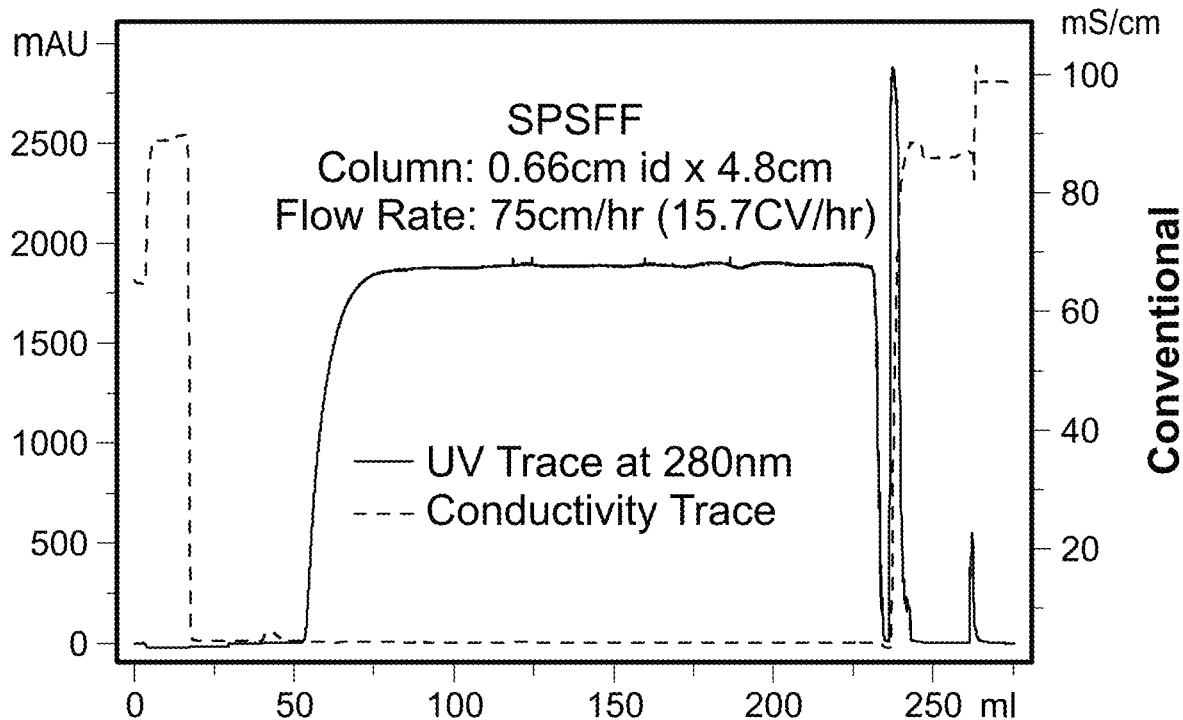
Figure 1C:
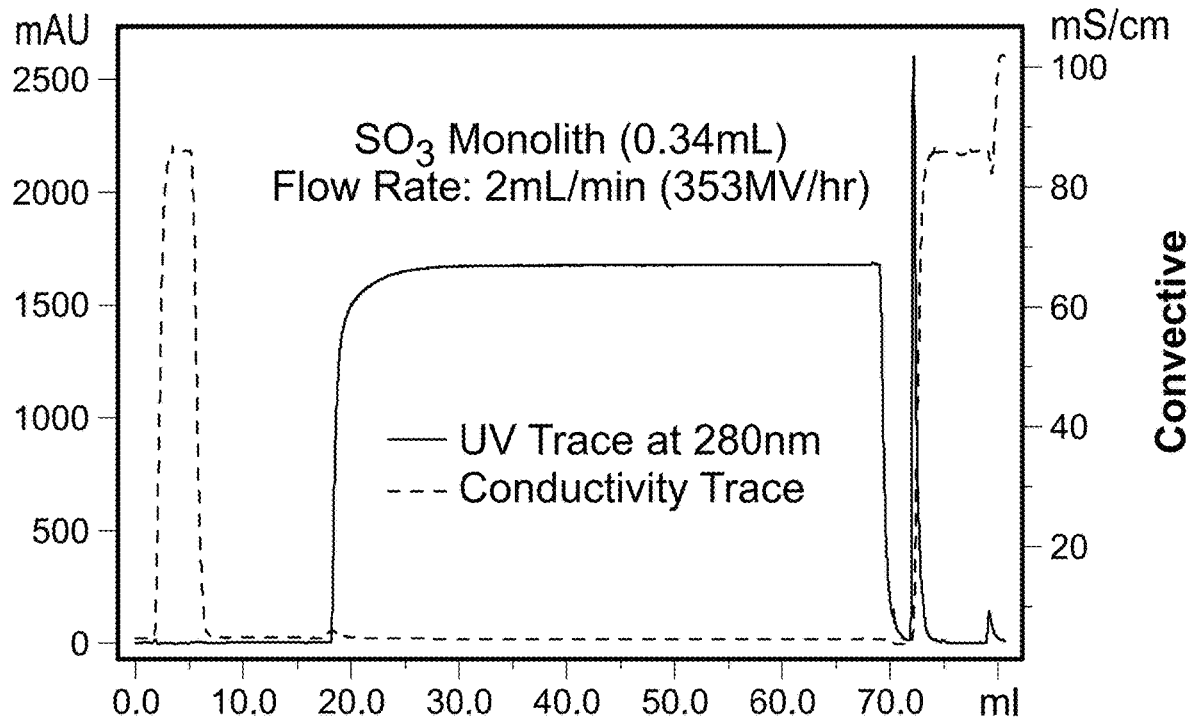
Figure 1D:
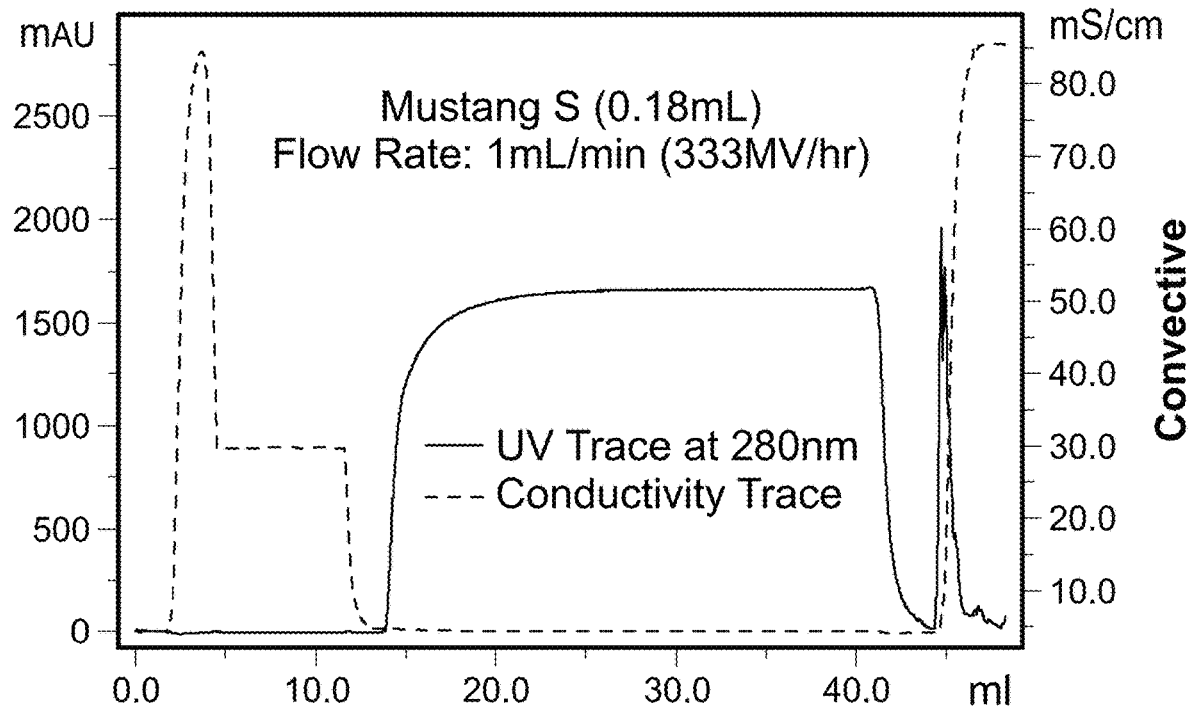

The term "polypeptide" or "protein" is meant a sequence of amino acids for which the chain length is sufficient to produce the higher levels of tertiary and/or quaternary structure. Thus, proteins are distinguished from "peptides" which are also amino acid-based molecules that do not have such structure. Typically, a protein for use herein will have a molecular weight of at least about 5-20 kD, alternatively at least about 15-20 kD, preferably at least about 20 kD. "Peptide" is meant a sequence of amino acids that generally does not exhibit a higher level of tertiary and/or quaternary structure. Peptides generally have a molecular weight of less than about 5 kD.

Examples of polypeptides encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

"Purified" polypeptide (e.g., antibody) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "epitope tagged" when used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a polypeptide which retain a biological and/or an immunological activity of native or naturally-occurring polypeptide, wherein "biological" activity refers to a biological function (either inhibitory or stimulatory) caused by a native or naturally-occurring polypeptide other than the ability to induce the production of an antibody against an antigenic epitope possessed by a native or naturally-occurring polypeptide and an "immunological" activity refers to the ability to induce the production of an antibody against an antigenic epitope possessed by a native or naturally-occurring polypeptide.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

"Complement dependent cytotoxicity" or "CDC" refer to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., J. Immunol. Methods 202:163 (1996), may be performed.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the polypeptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

A polypeptide that "inhibits the growth of tumor cells" or a "growth inhibitory" polypeptide is one which results in measurable growth inhibition of cancer cells. In one embodiment, growth inhibition can be measured at a polypeptide concentration of about 0.1 to about 30 pg/ml or about 0.5 nM to about 200 nM in cell culture, where the growth inhibition is determined 1-10 days after exposure of the tumor cells to the polypeptide. The polypeptide is growth inhibitory in vivo if administration of the polypeptide at about 1 pg/kg to about 100 mg/kg body weight results in reduction in tumor size or tumor cell proliferation within about 5 days to about 3 months from the first administration of the polypeptide, preferably within about 5 to about 30 days.

A polypeptide which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the polypeptide which induces apoptosis is one which results in about 2 to about 50 fold, preferably about 5 to about 50 fold, and most preferably about 10 to about 50 fold, induction of annexin binding relative to untreated cell in an annexin binding assay.

A polypeptide which "induces cell death" is one which causes a viable cell to become nonviable. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the polypeptide is able to induce cell death, loss of membrane integrity as evaluated by uptake of propidium iodide (PI), trypan blue (see Moore et al. Cytotechnology 17:1-11 (1995)) or 7AAD can be assessed relative to untreated cells.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed therebetween to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (LI), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab'fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab'fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *PNAS (USA)* 95:652-656 (1998).

"Human effector cells" are leukocytes that express one or more FcRs and perform effector functions. In some embodiments, the cells express at least FecγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FecγRI, FecγRII, and Fcγ RIII subclasses, including allelic variants and alternatively spliced forms of these receptors. FecγRII receptors include FecγRIIA (an "activating receptor") and FecγRIIB (an "inhibiting receptor"), which have similar amino acid sequences that differ primarily in the cytoplasmic domains thereof. Activating receptor FecγRIIA contains an immunoreceptor tyrosine-based activation motif (ITAM) in its cytoplasmic domain. Inhibiting receptor FecγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "sequential" as used herein refers to having no chromatography step between step (a) and (b) of the method.

The term "continuous" as used herein refers to having the cation exchange material and the mixed mode material either directly connected or some other mechanism which allows for continuous flow between the cation exchange material and the mixed mode material.

"Contaminants" refer to materials that are different from the desired polypeptide product. The contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Purification

Provided herein are methods for purifying a polypeptide from a composition comprising the polypeptide and at least one contaminant. In particular, the methods comprise using an overloaded cation exchange material. For example, the methods comprise loading onto a cation exchange material at a loading density of greater than about 150 g/L of cation exchange material.

The methods of purifying provided herein may further comprise loading onto a mixed mode material. For example, in some embodiments, the methods comprise the sequential steps of (a) loading the composition onto a cation exchange material at a loading density of greater than about 150 g/L of cation exchange material; and (b) loading a composition recovered from the cation exchange material onto a mixed mode material. In another example, in some embodiments, the methods comprise the sequential steps of (a) loading the composition onto a mixed mode material; and (b) loading a composition recovered from the mixed mode material onto a cation exchange material at a loading density of greater than about 150 g/L of cation exchange material. In some embodiments of any of the methods described herein, the sequential steps are continuous. In some embodiments of any of the methods described herein, the sequential steps are discontinuous. In some embodiments, the continuous purification utilizes the same flow rate, conductivity, and/or pH.

The methods described above may further comprise the step of loading onto a Protein A affinity chromatography material. The step of loading onto a Protein A affinity chromatography material is generally, but not necessarily, performed before the other chromatography step(s). In some embodiments, the step of loading onto a Protein A affinity chromatography material may be combined with the sequential steps of overloaded cation exchange and mixed mode, in any order, chromatography. In some embodiments, the sequential steps are continuous. In some embodiments, the continuous purification utilizes the same flow rate, conductivity, and/or pH.

Cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In a preferred embodiment, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate.

In some embodiments of any of the methods described herein, the cation exchange material may utilize a conventional chromatography material or a convective chromatography material. The conventional chromatography materials include, for example, perfusive materials (e.g., poly(styrene-divinylbenzene) resin) and diffusive materials (e.g., cross-linked agarose resin). In some embodiments, the poly(styrene-divinylbenzene) resin can be POROS® HS resin. The POROS® HS resin can be POROS® HS 50 μm or POROS® HS 20 μm particles. In some embodiments, the cross-linked agarose resin may be SP-SEPHAROSE® FAST FLOW ("SPSFF") resin. The convective chromatography material may be a membrane (e.g., polyethersulfone) or monolith material (e.g. cross-linked polymer). The polyethersulfone membrane may be Mustang S. The cross-linked polymer monolith material may be cross-linked poly(glycidyl methacrylate-co-ethylene dimethacrylate), e.g., monolith SO3.

Examples of cation exchange materials are known in the art include, but are not limited to MUSTANG® S, SARTO-BIND® S, SO3 Monolith, S CERAMIC HYPERD®, POROS® HS50, POROS® HS20, SPSFF, SP-SEPHAR-OSE® XL (SPXL), CM SEPHAROSE FAST FLOW™, CAPTO S™, FRACTOGEL-SE HICAP™, FRACTOGEL-SO3™, or FRACTOGEL™ COO. In some embodiments of any of the methods described herein, the cation exchange material is POROS® H550. In some embodiments, the POROS® HS resin may be POROS® HS 50 μm or POROS® HS 20 μm particles.

In some embodiments of any of the methods described herein, the mixed mode material comprises functional groups capable of one of more of the following functionalities: anionic exchange, hydrogen bonding, and hydrophobic interactions. In some embodiments, the mixed mode material comprises functional groups capable of anionic exchange and hydrophobic interactions. The mixed mode material may contain N-benzyl-N-methyl ethanol amine, 4-mercapto-ethyl-pyridine, hexylamine, or phenylpropylamine as ligand or contain cross-linked polyallylamine. Examples of the mixed mode materials include CAPTO™-ADHERE, MEP HYPERCEL™, HEA HYPERCEL™ or PPA HYPERCEL™ resin or CHROMASORB™ membrane. In some embodiments, the mixed mode material is CAPTO™-ADHERE resin.

In some embodiments, provided herein are methods for purifying a polypeptide from a composition comprising the polypeptide and at least one contaminant, wherein the method comprises either (i) or (ii): (i) sequential steps of (a) loading the composition onto POROS® HS50 at a loading density of greater than about 150 g/L of resin; and (b) loading a composition recovered from the POROS® HS50 onto CAPTO™-ADHERE; or (ii) sequential steps of (a) loading the composition onto CAPTO™-ADHERE; and (b) loading a composition recovered from CAPTO™-ADHERE onto POROS® HS50 at a loading density of greater than about 150 g/L of resin.

In some embodiments of any of the methods described herein, the composition is loaded onto a cation exchange material at a loading density of greater than about any of 150 g/L, 200 g/L, 300 g/L, 400 g/L, 500 g/L, 550 g/L, 600 g/L, 650 g/L, 700 g/L, 800 g/L, 900 g/L, or 1000 g/L of cation exchange material. The composition may be loaded onto a cation exchange material at a loading density of between about any of 150 g/L and 2000 g/L, 150 g/L and 1500 g/L, 150 g/L and 1000 g/L, 200 g/L and 1500 g/L, 300 g/L and 1500 g/L, 400 g/L and 1000 g/L, or 500 g/L and 1000 g/L of cation exchange material. In some embodiments, the composition is loaded onto a cation exchange material at a loading density of about any of 150 g/L, 300 g/L, 500 g/L, 550 g/L, 600 g/L, 650 g/L, 700 g/L, 800 g/L, 850 g/L, 900 g/L, 1000 g/L, 1500 g/L, or 2000 g/L of cation exchange material.

In some embodiments of any of the methods described herein, the composition is loaded onto a mixed mode material at a loading density of greater than about any of 25 g/L, 50 g/L, 75 g/L, 100 g/L, 150 g/L, 200 g/L, 300 g/L, 400 g/L, 500 g/L, or 550 g/L of mixed mode material. The composition is loaded onto a mixed mode material at a loading density of between about any of 25 g/L and 1000 g/L, 25 g/L and 700 g/L, or 25 g/L and 500 g/L of mixed mode material.

Various buffers which can be employed depending, for example, on the desired pH of the buffer, the desired conductivity of the buffer, the characteristics of the protein of interest, and the purification method. In some embodiments of any of the methods described herein, the methods comprise using a buffer. The buffer can be a loading buffer, an equilibration buffer, or a wash buffer. In some embodiments, one or more of the loading buffer, the equilibration buffer, and/or the wash buffer are the same. In some embodiments, the loading buffer, the equilibration buffer, and/or the wash buffer are different. In some embodiments of any of the methods described herein, the buffer comprises a salt. The buffer may comprise sodium chloride, sodium acetate, or a mixture thereof. In some embodiments, the buffer is a sodium chloride buffer. In some embodiments, the buffer is a sodium acetate buffer.

Load, as used herein, is the composition loaded onto a chromatography material. Loading buffer is the buffer used to load the composition comprising the polypeptide of interest onto a chromatography material. The chromatography material may be equilibrated with an equilibration buffer prior to loading the composition which is to be purified. The wash buffer is used after loading the composition onto a chromatography material to elute the polypeptide of interest from the solid phase.

Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments of any of the methods described herein, the conductivity has a conductivity of greater than about any of 2 mS/cm, 5 mS/cm, 7.5 mS/cm, or 10 mS/cm. The conductivity may be between about any of 2 mS/cm and 25 mS/cm, 2 mS/cm and 10 mS/cm, 3 mS/cm and 8 mS/cm, 2 mS/cm and 6 mS/cm, 4 mS/cm and 6 mS/cm, or 2 mS/cm and 4 mS/cm. In some embodiments, the conductivity is about any of 2 mS/cm, 3 mS/cm, 4 mS/cm, 5 mS/cm, 6 mS/cm, 8 mS/cm, or 10 mS/cm. In one aspect, the conductivity is the conductivity of the loading buffer, the equilibration buffer, and/or the wash buffer. In some embodiments, the conductivity of one or more of the loading buffer, the equilibration buffer, and the wash buffer are the same. In some embodiments, the conductivity of the loading buffer is different from the conductivity of the wash buffer and/or equilibration buffer.

In some embodiments of any of the methods described herein, the buffer has a pH of less than about any of 10, 9, 8, 7, or 6. The buffer may have a pH of between about any of 3 and 10, 4 and 8, 4 and 6, or 5 and 6. In some embodiments, the pH is about any of 4, 4.5, 5, 5.5, 6, 6.5, 7, 7.5, or 8. The pH can be the pH of the loading buffer, the equilibration buffer, or the wash buffer. In some embodiments, the pH of one or more of the loading buffer, the equilibration buffer, and/or the wash buffer are the same. In some embodiments, the pH of the loading buffer is different from the pH of the equilibration buffer and/or the wash buffer.

In some embodiments of any of the methods described herein, the flow rate is less than about any of 50 CV/hr, 40 CV/hr, or 30 CV/hr. The flow rate may be between about any of 5 CV/hr and 50 CV/hr, 10 CV/hr and 40 CV/hr, or 18 CV/hr and 36 CV/hr. In some embodiments, the flow rate is about any of 9 CV/hr, 18 CV/hr, 25 CV/hr, 30 CV/hr, 36 CV/hr, or 40 CV/hr. In some embodiments of any of the methods described herein, the flow rate is less than about any of 100 cm/hr, 75 cm/hr, or 50 cm/hr. The flow rate may be between about any of 25 cm/hr and 150 cm/hr, 25 cm/hr and 100 cm/hr, 50 cm/hr and 100 cm/hr, or 65 cm/hr and 85 cm/hr. The flow rate can be the flow rate over the cation exchange material or the flow rate over the mixed mode material. In some embodiments, the flow rate over the cation exchange material is the same as the flow rate over the mixed mode material. In some embodiments, the flow rate over the cation exchange material is different from the flow rate over the mixed mode material.

Bed height is the height of chromatography material used. In some embodiments of any of the method described herein, the bed height is greater than about any of 3 cm, 10 cm, or 15 cm. The bed height may be between about any of 3 cm and 35 cm, 5 cm and 15 cm, 3 cm and 10 cm, or 5 cm and 8 cm. In some embodiments, the bed height is about any of 3 cm, 5 cm, 10 cm, or 15 cm. In some embodiments, the bed height of the cation exchange material is the same as the bed height of the mixed mode material. In some embodiments, the bed height of the cation exchange material is different from the bed height of the mixed mode material.

In some embodiments of any of the methods described herein, the at least one contaminant is any one or more of CHOP, leached protein A, DNA, aggregated protein, cell culture media component, gentamicin, and viral contaminant.

CHOP are proteins from host cells, i.e., Chinese Hamster Ovary Proteins. The amount of CHOP may be measured by enzyme-linked immunosorbent assay ("ELISA") or Meso Scale Discovery ("MSO"). In some embodiments of any of the methods described herein, the amount of CHOP is reduced by greater than about any of 10%, 20%, 30%, 40%, 50%, 60%, 70%, 80%, 90%, or 95%. The amount of CHOP may be reduced by between about any of 10% and 99%, 30% and 95%, 30% and 99%, 50% and 95%, 50% and 99%, 75% and 99%, or 85% and 99%. In some embodiments, the amount of CHOP is reduced by about any of 10%, 20%, 30%, 40%, 50%, 60%, 70%, 80%, 85%, 90%, 95%, or 98%. In some embodiments, the reduction is determined by comparing the amount of CHOP in the composition recovered from a purification step(s) to the amount of CHOP in the composition before the purification step(s).

Aggregated polypeptide can be high molecular weight (HMW) protein. In some embodiments, the aggregated polypeptide is multimers of the polypeptide of interest. The HMW may be a dimmer, up to 8x monomer, or larger of the polypeptide of interest. Methods of measuring aggregated protein (e.g., HMW) are known in the art and described in the examples section. In some embodiments of any of the methods described herein, the amount of aggregated protein is reduced by greater than about any of 5%, 10%, 20%, 30%, 40%, 50%, 60%, 70%, 80%, 90%, or 95%. The amount of aggregated protein may be reduced by between about any of 10% and 99%, 30% and 95%, 30% and 99%, 50% and 95%, 50% and 99%, 75% and 99%, or 85% and 99%. The amount of aggregated protein may be reduced by about any of 5%, 10%, 20%, 30%, 40%, 50%, 60%, 70%, 80%, 90%, or 95%. In some embodiments, the reduction is determined by comparing the amount of aggregated protein (e.g., HMW) in the composition recovered from a purification step(s) to the amount of aggregated protein (e.g., HMW) in the composition before the purification step(s).

Leached Protein A is Protein A detached or washed from a solid phase to which it is bound. For example, leached Protein A can be leached from Protein A chromatography column. The amount of Protein A may be measured, for example, by ELISA. In some embodiments of any of the methods described herein, the amount of leached Protein A is reduced by greater than about any of 10%, 20%, 30%, 40%, 50%, 60%, 70%, 80%, or 90%. The amount of leached Protein A may be reduced by between about any of 10% and 99%, 30% and 95%, 30% and 99%, 50% and 95%, 50% and 99%, 75% and 99%, or 85% and 99%. In some embodiments, the amount of leached Protein A is reduced by about any of 10%, 20%, 30%, 40%, 50%, 60%, 70%, 80%, 90%, or 95%. In some embodiments, the reduction is determined by comparing the amount of leached Protein A in the composition recovered from a purification step(s) to the amount of leached Protein A in the composition before the purification step(s).

Methods of measuring DNA such as CHO cell DNA are known in the art and described in the examples section. In some embodiments of any of the methods described herein, the amount of DNA is reduced by greater than about any of 10%, 20%, 30%, 40%, 50%, 60%, 70%, 80%, or 90%. The amount of DNA may be reduced by between about any of 10% and 99%, 30% and 95%, 30% and 99%, 50% and 95%, 50% and 99%, 75% and 99%, or 85% and 99%. The amount of DNA may be reduced by about any of 10%, 20%, 30%, 40%, 50%, 60%, 70%, 80%, 90%, 95%, or 99%. In some embodiments, the reduction is determined by comparing the amount of DNA in the composition recovered from a purification step(s) to the amount of DNA in the composition before the purification step(s).

Cell culture media component refers to a component present in a cell culture media. A cell culture media may be a cell culture media at the time of harvesting cells. In some embodiments, the cell culture media component is gentamicin. The amount of gentamicin may be measured by ELISA. In some embodiments of any of the methods described herein, the amount of cell culture media component is reduced by greater than about any of 10%, 20%, 30%, 40%, 50%, 60%, 70%, 80%, or 90%. The amount of cell culture media component may be reduced by between about any of 10% and 99%, 30% and 95%, 30% and 99%, 50% and 95%, 50% and 99%, 75% and 99%, or 85% and 99%. In some embodiments, the amount of cell culture media component is reduced by about any of 10%, 20%, 30%, 40%, 50%, 60%, 70%, 80%, 90%, 95%, or 98%. In some embodiments, the reduction is determined by comparing the amount of cell culture media component in the composition recovered from a purification step(s) to the amount of cell culture media component in the composition before the purification step(s).

In some embodiments of any of the methods described herein, the methods may further comprise one or more purification steps either prior to, or after, any of the chromatography steps described herein. In some embodiments, the methods further comprise subjecting the composition comprising the polypeptide to one or more further purification steps either before or after steps (a) and (b). Other purification procedures include, for example, hydroxylapatite chromatography; gel filtration chromatography; affinity chromatography; gel electrophoresis; dialysis; ethanol precipitation; reverse phase HPLC; chromatography on silica; chromatofocusing; SDS-PAGE; ammonium sulfate precipitation; and metal chelating columns to bind epitope-tagged forms of the polypeptide.

In some embodiments of any of the methods described herein, the methods further comprise recovering the purified polypeptide. In some embodiments, the purified polypeptide is recovered from any of the purification steps described herein. The chromatography step may be cation exchange chromatography, mixed mode chromatography, or Protein A chromatography.

In some embodiments of any of the methods described herein, the methods further comprise combining the purified polypeptide of the methods of purification with a pharmaceutically acceptable carrier.

III. Polypeptides

Polypeptides are provided for use in any of the methods of purifying polypeptides and formulations comprising the polypeptides purified by the methods described herein.

In some embodiments, the polypeptide is a therapeutic polypeptide. The therapeutic polypeptide may inhibit the growth of tumor cells, induce apoptosis, and/or induce cell death. In some embodiments, the polypeptide is an antagonist. In some embodiments, the polypeptide is an agonist. In some embodiments, the polypeptide is an antibody.

In some embodiments, the polypeptide has a molecular weight of greater than about any of 5,000 Daltons, 10,000 Daltons, 15,000 Daltons, 25,000 Daltons, 50,000 Daltons, 75,000 Daltons, 100,000 Dalton, 125,000 Daltons, or 150,000 Daltons. The polypeptide may have a molecular weight between about any of 50,000 Daltons to 200,000 Daltons or 100,000 Daltons to 200,000 Daltons. Alternatively, the polypeptide for use herein may have a molecular weight of about 120,000 Daltons or about 25,000 Daltons.

pI is the isoelectric point and is the pH at which a particular molecule or surface carries no net electrical charge. In some embodiments of any of the methods described herein, the pI of the polypeptide may be between about any of 6 to 10, 7 to 9, or 8 to 9. In some embodiments, the polypeptide has a pI of about any of 6, 7, 7.5, 8, 8.5, 9, 9.5, or 10.

The polypeptides to be purified using the methods described herein is generally produced using recombinant techniques. Methods for producing recombinant proteins are described, e.g., in U.S. Pat. Nos. 5,534,615 and 4,816,567, specifically incorporated herein by reference. In some embodiments, the protein of interest is produced in a CHO cell (see, e.g. WO 94/11026). When using recombinant techniques, the polypeptides can be produced intracellularly, in the periplasmic space, or directly secreted into the medium.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

(A) Antibodies

In some embodiments of any of the methods described herein, the polypeptide for use in any of the methods of purifying polypeptides and formulations comprising the polypeptides purified by the methods described herein is an antibody.

Molecular targets for antibodies include CD proteins and their ligands, such as, but not limited to: (i) CD3, CD4, CD8, CD19, CD11a, CD20, CD22, CD34, CD40, CD79a (CD79a), and CD79P (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and □v/□3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mp1 receptor; CTLA-4; protein C, BR3, c-met, tissue factor, □7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

(i) Polyclonal Antibodies

In some embodiments, the antibodies are polyclonal antibodies. Polyclonal antibodies are preferably raised in animals by multiple subcutaneous (sc) or intraperitoneal (ip) injections of the relevant antigen and an adjuvant. It may be useful to conjugate the relevant antigen to a polypeptide that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the polypeptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different polypeptide and/or through a different cross-linking reagent. Conjugates also can be made in recombinant cell culture as polypeptide fusions. Also, aggregating agents such as alum are suitably used to enhance the immune response.

(iii) Monoclonal Antibodies

In some embodiments, the antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., Nature 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, California USA, and SP-2 or X63-Ag8-653 cells available from the American Type Culture Collection, Rockville, Maryland USA. Human myeloma and mouse-human heteromyeloma cell lines also have been described for the production of human monoclonal antibodies (Kozbor, J. Immunol. 133:3001 (1984); Brodeur et al., Monoclonal Antibody Production Techniques and Applications pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem. 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-SEPHAROSE®, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., Curr. Opinion in Immunol. 5:256-262 (1993) and Plückthun, Immunol. Revs., 130:151-188 (1992).

In a further embodiment, antibodies or antibody fragments can be isolated from antibody phage libraries generated using the techniques described in McCafferty et al., Nature 348:552-554 (1990). Clackson et al., Nature 352:624-628 (1991) and Marks et al., J. Mol. Biol. 222:581-597 (1991) describe the isolation of murine and human antibodies, respectively, using phage libraries. Subsequent publications describe the production of high affinity (nM range) human antibodies by chain shuffling (Marks et al., Bio/

Technology 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., Proc. Natl Acad. Sci. USA 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

(iv) Humanized Antibodies

In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(v) Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(vi) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab'fragment, a F(ab')$_2$ fragment, a scFv, a Fv, and a diabody.

(vii) Bispecific Antibodies

In some embodiments, the antibody is a bispecific antibody. Bispecific antibodies are antibodies that have binding specificities for at least two different epitopes. Exemplary bispecific antibodies may bind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab'fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab'portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(viii) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

(ix) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. J., *Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in the methods of purifying polypeptides (e.g., antibodies) described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, Science 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 1 below under the heading of "preferred substitutions." If such substitutions result in a change in biological activity, then more substantial changes, denominated "exemplary substitutions" in the Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |

TABLE 1-continued

| Original Residue | Exemplary Substitutions | Preferred Substitutions |
| --- | --- | --- |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, Biochemistry second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polyeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(ii) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, CH1, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated polypeptides. Examples include $^{212}$Bi, $^{131}$I, $^{131}$In, $^{90}$Y, and $^{186}$Re. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC1065, and the derivatives of these toxins that have toxin activity, are also contemplated herein.

Maytansinoids are mitototic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disufide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics are capable of producing double-stranded DNA breaks at sub-picomolar concentrations. For the preparation of conjugates of the calicheamicin family, see, e.g., U.S. Pat. No. 5,712,374. Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase).

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to covert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e.g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 18th edition, Gennaro, A. R., Ed., (1990).

IV. Obtaining Polypeptides for Use in the Formulations and Methods

The polypeptides used in the methods of purification described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and $F(ab')_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

Suitably, the polynucleotides described herein may be isolated and/or purified. In some embodiments, the polynucleotides are isolated polynucleotides.

The term "isolated polynucleotide" is intended to indicate that the molecule is removed or separated from its normal or natural environment or has been produced in such a way that it is not present in its normal or natural environment. In some embodiments, the polynucleotides are purified polynucleotides. The term purified is intended to indicate that at least some contaminating molecules or substances have been removed.

Suitably, the polynucleotides are substantially purified, such that the relevant polynucleotides constitutes the dominant (i.e., most abundant) polynucleotides present in a composition.

Recombinant nucleic acids comprising an insert coding for a heavy chain variable domain and/or for a light chain variable domain may be used in the methods as described herein. By definition such nucleic acids comprise coding single stranded nucleic acids, double stranded nucleic acids consisting of said coding nucleic acids and of complementary nucleic acids thereto, or these complementary (single stranded) nucleic acids themselves.

Modification(s) may also be made outside the heavy chain variable domain and/or of the light chain variable domain of the antibody. Such a mutant nucleic acid may be a silent mutant wherein one or more nucleotides are replaced by other nucleotides with the new codons coding for the same amino acid(s). Such a mutant sequence may be a degenerate sequence. Degenerate sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or the light chain variable domain.

Sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity."

In some embodiments, homologous amino acid sequence and/or nucleotide sequence should encode a polypeptide which retains the functional activity and/or enhances the activity of the antibody. In some embodiments, homologous sequence is taken to include an amino acid sequence which may be at least about any of 75, 85, or 90% identical, preferably at least about 95 or 98% identical to the subject sequence. Typically, the homologues will comprise the same active sites etc. as the subject amino acid sequence. Although homology can also be considered in terms of similarity (i.e., amino acid residues having similar chemical properties/functions). In some embodiments, it is preferred to express homology in terms of sequence identity.

In the present context, a homologous sequence is taken to include a nucleotide sequence which may be at least about any of 75, 85, or 90% identical, preferably at least about 95 or 98% identical to a nucleotide sequence encoding a polypeptide described herein (the subject sequence). Typically, the homologues will comprise the same sequences that code for the active sites etc. as the subject sequence. Although homology can also be considered in terms of similarity (i.e., amino acid residues having similar chemical properties/functions). In some embodiments, it is preferred to express homology in terms of sequence identity.

These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the polypeptide.

(B) Expression of Polynucleotides

The description below relates primarily to production of polypeptides by culturing cells transformed or transfected with a vector containing polypeptide-encoding polynucleotides. It is, of course, contemplated that alternative methods, which are well known in the art, may be employed to prepare polypeptides. For instance, the appropriate amino acid sequence, or portions thereof, may be produced by direct peptide synthesis using solid-phase techniques (see, e.g., Stewart et al., *Solid-Phase Peptide Synthesis* W.H. Freeman Co., San Francisco, Calif. (1969); Merrifield, *J. Am. Chem. Soc.* 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the polypeptide may be chemically synthesized separately and combined using chemical or enzymatic methods to produce the desired polypeptide.

Polynucleotides as described herein are inserted into an expression vector(s) for production of the polypeptides. The term "control sequences" refers to DNA sequences necessary for the expression of an operably linked coding sequence in a particular host organism. The control sequences include, but are not limited to, promoters (e.g., naturally-associated or heterologous promoters), signal sequences, enhancer elements, and transcription termination sequences.

A polynucleotide is "operably linked" when it is placed into a functional relationship with another polynucleotide sequence. For example, nucleic acids for a presequence or secretory leader is operably linked to nucleic acids for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

For antibodies, the light and heavy chains can be cloned in the same or different expression vectors. The nucleic acid segments encoding immunoglobulin chains are operably linked to control sequences in the expression vector(s) that ensure the expression of immunoglobulin polypeptides.

Selection Gene Component—Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., U.S. Pat. No. 4,704,362). In some embodiments, selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the nucleic acid encoding antibodies described herein, such as DHFR, thymidine kinase, metallothionein-I and —III, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding a polypeptide described herein, wild-type DHFR protein, and another selectable marker such as aminoglycoside 3-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 (1979)). The trp1 gene provides a selection marker for a mutant strain of yeast lacking the ability to grow in tryptophan, for example, ATCC No. 44076 or PEP4-1. Jones, *Genetics* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K lactis*. Van den Berg, *Bio/Technology* 8:135 (1990). Stable multi-copy expression vectors for secretion of mature recombinant human serum albumin by industrial strains of *Kluyveromyces* have also been disclosed. Fleer et al., *Bio/Technology* 9:968-975 (1991).

Signal Sequence Component—The polypeptides may be produced recombinantly not only directly, but also as a fusion polypeptide with a heterologous polypeptide, which is preferably a signal sequence or other polypeptide having a specific cleavage site at the N-terminus of the mature polypeptide. The heterologous signal sequence selected preferably is one that is recognized and processed (i.e., cleaved by a signal peptidase) by the host cell. A signal sequence can be substituted with a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The nucleic acid sequence for such precursor region is ligated in reading frame to the nucleic acid sequence encoding the polypeptide described herein.

Origin of Replication-Both expression and cloning vectors contain a polynucleotide sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2p plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Promoter Component—Expression and cloning vectors usually contain a promoter that is recognized by the host organism and is operably linked to the nucleic acid encoding the polypeptide. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide.

Suitably, the expression control sequences are eukaryotic promoter systems in vectors capable of transforming or transfecting eukaryotic host cells (e.g., COS cells—such as COS 7 cells—or CHO cells). Once the vector has been incorporated into the appropriate host, the host is maintained under conditions suitable for high level expression of the nucleotide sequences, and the collection and purification of the cross-reacting antibodies.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

The transcription of the polypeptides described herein from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

Enhancer Element Component—Transcription of a DNA encoding the polypeptide described herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Transcription Termination Component—Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. One useful transcription termination component is the bovine growth hormone polyadenylation region. See WO94/11026 and the expression vector disclosed therein.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and about 98 to 99% or more homogeneity is most preferred, for pharmaceutical uses.

(C) Constructs

Typically the construct will be an expression vector allowing expression, in a suitable host, of the polypeptide(s) encoded by the polynucleotide. The construct may comprise, for example, one or more of the following: a promoter active in the host; one or more regulatory sequences, such as enhancers; an origin of replication; and a marker, preferably a selectable marker. The host may be a eukaryotic or prokaryotic host, although eukaryotic (and especially mammalian) hosts may be preferred. The selection of suitable promoters will obviously depend to some extent on the host cell used, but may include promoters from human viruses such as HSV, SV40, RSV and the like. Numerous promoters are known to those skilled in the art.

The construct may comprise a polynucleotide which encodes a polypeptide comprising three light chain hypervariable loops or three heavy chain hypervariable loops. Alternatively the polynucleotide may encode a polypeptide comprising three heavy chain hypervariable loops and three light chain hypervariable loops joined by a suitably flexible linker of appropriate length. Another possibility is that a single construct may comprise a polynucleotide encoding two separate polypeptides—one comprising the light chain loops and one comprising the heavy chain loops. The separate polypeptides may be independently expressed or may form part of a single common operon.

The construct may comprise one or more regulatory features, such as an enhancer, an origin of replication, and one or more markers (selectable or otherwise). The construct may take the form of a plasmid, a yeast artificial chromosome, a yeast mini-chromosome, or be integrated into all or part of the genome of a virus, especially an attenuated virus or similar which is non-pathogenic for humans.

The construct may be conveniently formulated for safe administration to a mammalian, preferably human, subject. Typically, they will be provided in a plurality of aliquots, each aliquot containing sufficient construct for effective immunization of at least one normal adult human subject.

The construct may be provided in liquid or solid form, preferably as a freeze-dried powder which, typically, is rehydrated with a sterile aqueous liquid prior to use.

The construct may be formulated with an adjuvant or other component which has the effect of increasing the immune response of the subject (e.g., as measured by specific antibody titer) in response to administration of the construct.

(D) Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

The vectors may be for example, plasmid, virus or phage vectors provided with an origin of replication, optionally a promoter for the expression of the said polynucleotide and optionally a regulator of the promoter. Vectors may contain one or more selectable marker genes which are well known in the art.

These expression vectors are typically replicable in the host organisms either as episomes or as an integral part of the host chromosomal DNA.

(E) Host Cells

The host cell may be a bacterium, a yeast or other fungal cell, insect cell, a plant cell, or a mammalian cell, for example.

A transgenic multicellular host organism which has been genetically manipulated may be used to produce a polypeptide. The organism may be, for example, a transgenic mammalian organism (e.g., a transgenic goat or mouse line).

Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P), *Pseudomonas* such as *P. aeruginosa*, and *Streptomyces*. These examples are illustrative rather than limiting. Strain W3110 is one particularly preferred host or parent host because it is a common host strain for recombinant polynucleotide product fermentations. Preferably, the host cell secretes minimal amounts of proteolytic enzymes. For example, strain W3110 may be modified to effect a genetic mutation in the genes encoding polypeptides endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan'; *E. coli* W3110 strain 37D6, which has the complete genotype tonA ptr3 phoA E15 (argF-lac)169 degP ompT rbs7 ilvG kan'; *E. coli* W3110 strain 40B4, which is strain 37D6 with a non-kanamycin resistant degP deletion mutation; and an *E. coli* strain having mutant periplasmic protease. Alternatively, in vitro methods of cloning, e.g., PCR or other nucleic acid polymerase reactions, are suitable.

In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Eukaryotic microbes may be used for expression. Eukaryotic microbes such as filamentous fungi or yeast are suitable cloning or expression hosts for polypeptide-encoding vectors. *Saccharomyces cerevisiae* is a commonly used lower eukaryotic host microorganism. Others include *Schizosaccharomyces pombe; Kluyveromyces* hosts such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans*, and *A. niger*. Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides as described herein and in some instances are preferred (See Winnacker, *From Genes to Clones* VCH Publishers, N.Y., N.Y. (1987). For some embodiments, eukaryotic cells may be preferred, because a number of suitable host cell lines capable of secreting heterologous polypeptides (e.g., intact immunoglobulins) have been developed in the art, and include CHO cell lines, various Cos cell lines, HeLa cells, preferably, myeloma cell lines, or transformed B-cells or hybridomas. In some embodiments, the mammalian host cell is a CHO cell.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR(CHO or CHO-DP-12 line); mouse sertoli cells; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Alternatively, polypeptide-coding sequences can be incorporated into transgenes for introduction into the genome of a transgenic animal and subsequent expression in the milk of the transgenic animal. Suitable transgenes include coding sequences for light and/or heavy chains in operable linkage with a promoter and enhancer from a mammary gland specific gene, such as casein or beta lactoglobulin.

Alternatively, the antibodies described herein can be produced in transgenic plants (e.g., tobacco, maize, soybean and alfalfa). Improved 'plantibody' vectors (Hendy et al., *J. Immunol. Methods* 231:137-146 (1999)) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see Larrick et al., *Res. Immunol.* 149:603-608 (1998)).

Host cells are transfected or transformed with expression or cloning vectors described herein for polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach* M. Butler, ed. (IRL Press, 1991).

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride or electroporation is generally used for prokaryotes. Infection with *Agrobacterium tumefaciens* is used for transformation of certain plant cells, as described by Shaw et al., Gene 23:315 (1983) and WO 89/05859 published 29 Jun. 1989. For mammalian cells without such cell walls, the calcium phosphate precipitation method of Graham and van der Eb, *Virology* 52:456-457 (1978) can be employed. General aspects of mammalian cell host system transfections have been described in U.S. Pat. No. 4,399,216. Transformations into yeast are typically carried out according to the method of Van Solingen et al., *J. Bact.* 130:946 (1977) and Hsiao et al., *Proc. Natl. Acad. Sci.* (USA) 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology* 185:527-537 (1990) and Mansour et al., *Nature* 336:348-352 (1988).

Polypeptides, e.g., antibodies, can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of polypeptides in bacteria, see, e.g., U.S. Pat. No. 5,840,523, which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

Suitable host cells for the expression of glycosylated polypeptides described herein are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein, particularly for transfection of *Spodoptera frugiperda* cells.

The host cells used to produce the polypeptide may be cultured in a variety of media. Commercially available media such as Ham's F10 (Sigma), Minimal Essential Medium (MEM), (Sigma), RPMI-1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

V. Formulations and Methods of Making of the Formulations

Provided herein are also formulations and methods of making the formulation comprising the polypeptides (e.g., antibodies) purified by the methods described herein. For example, the purified polypeptide may be combined with a pharmaceutically acceptable carrier.

The polypeptide formulations in some embodiments may be prepared for storage by mixing a polypeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, the polypeptide in the polypeptide formulation maintains functional activity.

The formulations to be used for in vivo administration must be sterile. This is readily accomplished by filtration through sterile filtration membranes.

The formulations herein may also contain more than one active compound as necessary for the particular indication being treated, preferably those with complementary activities that do not adversely affect each other. For example, in addition to a polypeptide, it may be desirable to include in the one formulation, an additional polypeptide (e.g., antibody). Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

V. Articles of Manufacture

The polypeptides purified by the methods described herein and/or formulations comprising the polypeptides purified by the methods described herein may be contained within an article of manufacture. The article of manufacture may comprise a container containing the polypeptide and/or the polypeptide formulation. Preferably, the article of manufacture comprises: (a) a container comprising a composition comprising the polypeptide and/or the polypeptide formulation described herein within the container; and (b) a package insert with instructions for administering the formulation to a subject.

The article of manufacture comprises a container and a label or package insert on or associated with the container. Suitable containers include, for example, bottles, vials, syringes, etc. The containers may be formed from a variety of materials such as glass or plastic. The container holds or contains a formulation and may have a sterile access port (for example the container may be an intravenous solution bag or a vial having a stopper pierceable by a hypodermic injection needle). At least one active agent in the composition is the polypeptide. The label or package insert indicates that the composition's use in a subject with specific guidance regarding dosing amounts and intervals of polypeptide and any other drug being provided. The article of manufacture may further include other materials desirable from a commercial and user standpoint, including other buffers, diluents, filters, needles, and syringes. In some embodiments, the container is a syringe. In some embodiments, the syringe is further contained within an injection device. In some embodiments, the injection device is an autoinjector.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Example 1—Selection of Overloaded Cation Exchange Materials

This example describes a cation exchange chromatography process for purifying a recombinant humanized anti-vascular endothelial growth factor (VEGF) antibody, a recombinant humanized anti-CD11a antibody, and a recombinant chimeric anti-CD20 antibody. The structures of anti-VEGF antibody, anti-CD11a antibody, and anti-CD20 antibody were disclosed in U.S. Pat. Nos. 7,169,901, and 6,703,018, and 5,736,137, respectively, each of which is expressly incorporated herein by reference.

Materials and Methods

Purification Methods

The cell culture fluid containing monoclonal antibody produced in Chinese hamster ovary cells was processed by continuous centrifuge to remove cellular debris, and further clarified through filtration with depth filters and 0.2 um filter. The harvested cell culture fluids were purified through protein A chromatography. The loading and washing conditions were at neutral pH range and elution was carried out at low pH range during the chromatography. pH and conductivity of the protein pools obtained from the protein A column were adjusted to the loading conditions used for cation exchange chromatography and then 0.22 um filtered. The same pH and conductivity were used for the cation exchange chromatography loading conditions, equilibration conditions, and initial wash conditions. The filtered and equilibrated protein pools were used as the product for subsequent cation exchange chromatography. Concentration of product (g/L) was determined by absorbance 280 nm. Specific cation exchange chromatography conditions were performed as indicated in the Experimental Procedures and Results section below.

Assays

Assays for all examples were performed as indicated below.

Antibody Concentration Assay

Antibody concentration in harvested cell culture fluid (HCCF) was determined using a POROS® protein A HPLC assay (Applied Biosystems, Foster City, Calif.). The column was operated at a flow rate of 2.0 mL/min where it was equilibrated in sodium phosphate/sodium chloride buffer at pH 6.3 and eluted with acetic acid/glycine solution at pH 2.5. Absorbance at 280 nm was monitored and the elution peak area used to quantify antibody concentration from a standard curve. Antibody in purified pools obtained through protein A affinity or ion exchange chromatography was determined by absorbance at 280 nm (with absorbance at 320 nm subtracted to correct for light scattering), using a spectrophotometer with 10 mm path length flow cell. Antibody concentration was calculated as [(absorbance at 280 nm×absorbance at 320 nm)×dilution]/extinction coefficient.

CHOP Assay

Two CHOP assays, enzyme linked immunosorbent assay (ELISA) and Meso Scale Discovery (MSD) assays, were used.

CHOP ELISA Assay-Samples from selected runs were submitted to an assay group that performed a standard and validated ELISA to quantitate the levels of CHOP. Affinity-purified goat anti-CHOP antibodies were immobilized on microtiter plate wells. Dilutions of the samples containing CHOP, standards, and controls, were incubated in the wells, followed by incubation with goat anti-CHOP antibodies conjugated to horseradish peroxidase. The horseradish peroxidase enzymatic activity was detected with o-phenylenediamine dihydrochloride. The CHOP was quantitated by reading absorbance at 492 nm in a microtiter plate reader. A computer curve-fitting program was used to generate the standard curve and automatically calculate the sample concentration. The assay range for the ELISA was typically 5 ng/mL to 320 ng/mL, and results were standardized to ppm for pool comparisons.

CHOP MSD Assay-Samples from selected runs were submitted to an assay group that performed a standard and validated MSD assay to quantitate the levels of CHOP. Affinity-purified goat anti-CHOP antibodies were immobilized on microtiter plate wells. Dilutions of the samples containing CHOP, standards, and controls, were incubated in the wells, followed by incubation with goat anti-CHOP antibodies conjugated to MSD SULFO-TAG NHS-ESTER. The NHS-ESTER has an amine-reactive linker, N-hydroxysuccinimide ester, which readily couples to primary amine groups of proteins. The CHOP concentration was measured after addition of the MSD Read Buffer and applying electricity to the bottom of the plate. The labeled detection antibodies interacted with the tripropylamine-containing Read Buffer to emit light upon electrochemical stimulation initiated at the electrode surfaces of Multi-Array microplates at 620 nm and was measured by a CCD camera. The concentration was then obtained by inverse regression on the standard curve. The assay range for the assay was 5 ng/mL to 1530 ng/mL, and results were standardized to ppm for pool comparison.

Protein A Assay

Leached Protein A in samples where Protein A chromatography has been used for the recovery process was detected. The level of Protein-A was determined by a sandwich Protein-A ELISA. Chicken anti-staphylococcal protein A antibodies were immobilized on microtiter plate wells. The sample treatment procedure included sample dilution and then dissociation of the Protein A/IgG complex using microwave assisted heating as a pretreatment step before running the samples on a sandwich ELISA. Protein A, if present in the sample, bound the coat antibody. Bound protein A was detected with horseradish peroxidase conjugated anti-protein antibodies. Horseradish peroxidase enzymatic activity was quantified with a 2 component TMB substrate solution which produces a colorimetric signal.

Gentamicin Assay

A competitive ELISA was used to determine gentamicin concentrations in all of the pools. Goat polyclonal antibodies to gentamicin-BSA were immobilized on microtiter platre wells. Gentamicin competed with biotinylated-gentamicin for binding to the antibodies. The amount of bound biotin-labeled gentamicin was detected with the addition of horseradish peroxidase-streptavidin and o-phenylendiamine substract. Samples were serially diluted in assay diluent so that the absorbance reading fell within the quantifiable range of the assay (0.37-90 ng/mL).

Size Exclusion Chromatography

The size heterogeneity of the monoclonal antibodies was determined by a high-performance size exclusion chromatography assay. It employed a TSK-GEL® G3000SWXL column (7.8 mm×300 mm, Tosoh Bioscience, Montgomery-ville, Pa.) to separate monomer and higher molecular weight species (HMWs). The column was operated at a flow rate of 0.3 mL/min using a 200 mM potassium phosphate, 250 mM potassium chloride pH 6.2 mobile phase. 20 µg of antibody was injected for each sample. Absorbance at 280 nm was used to monitor the separation of monomer and HMWs. Percentages of monomer and HMWs were calculated based on their peak areas.

DNA Assay

Taqman® PCR for CHO cell DNA assay uses real-time PCR to detect and quantify CHO DNA in product samples. DNA from samples and controls are first extracted using Qiagen's Virus BIOROBOT® kit. The extracted samples, controls, and standard DNA, are subject to Taqman® real time Polymerase chain reaction (PCR) using PCR primers and probe in a 96-well plate with ABI's sequence detection system. The primers are defined by a 110 base pair segment of a repetitive DNA sequence in the *Cricetulus griseus* genome. The probe was labeled with a fluorescent reporter dye at 5' end and a quencher dye at the 3' end. When the probe is intact, the emission spectrum of the reporter is suppressed by the quencher. The 5' nuclease activity of polymerase hydrolyzes the probe and releases the report, which results in an increase in fluorescence emission. The sequence detector quantifies the amplified product in direct proportion to the increase in fluorescence emission measured continuously during the DNA amplification. Cycle numbers at which DNA has amplified past the threshold (CT) are calculated for the standard curve. A standard curve ranging 1 pg/mL-10,000 pg/mL is generated, which is used for quantifying DNA in samples.

Experimental Procedures and Results
Purification of Anti-CD11a Antibody

Three types of cation exchange materials were evaluated in this study: resin, membrane, and monolith. The overloaded cation exchange purification processes of anti-CD11a antibody using these three cation exchange materials were evaluated with respect to process performance (e.g., impurities removal, step yield, and product quality).

The chromatograms of the three types of cation exchange materials, resin (POROS® HS50 column (0.66 cm inner diameter ("i.d.")×5 cm, 15.1 CV/hr) and SP SEPHAROSE FF™ ("SPSFF") (0.66 cm i.d.×4.8 cm, 15.7 CV/hr)), monolith (SO3 Monolith (0.34 mL, 353 MV/hr)), and membrane (MUSTANG S® (0.18 mL, 333 MV/hr)), loaded with the product up to 1000 g/L CV (column volume) or MV (membrane or monolith volume), were run at pH 5.5 and 3 mS/cm. See FIG. 1.

Figure 2:
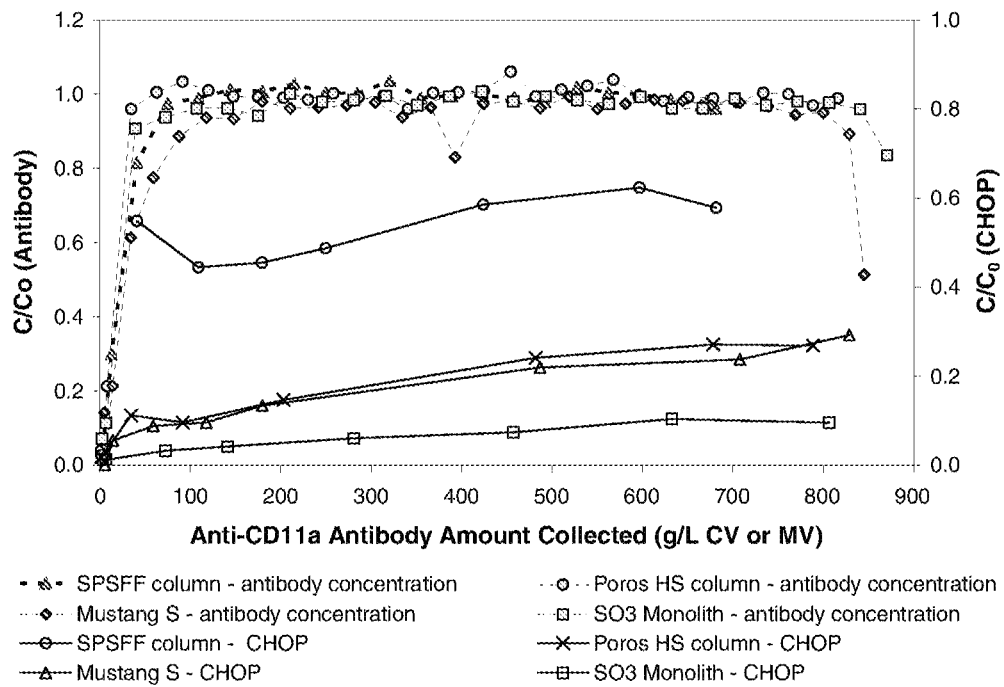
FIG. 2 shows $C/C_0$ (the Mab ("monomer antibody") concentration) and $C/C_0$ (the Chinese Hamster Ovary Protein ("CHOP") concentration) with varying amount of the product comprising anti-CD11a antibody collected (g/L CV or MV) using SPSFF, POROS® HS50, MUSTANG® S, and SO3 monolith. C is the Mab or CHOP concentration in the collected fraction and $C_0$ is the Mab or CHOP concentration in the load.

The performance of the three types of cation exchange materials, resin (POROS® HS50 column (15.1 CV/hr or 75 cm/hr) and SPSFF column (15.7 CV/hr or 75 cm/hr)), membrane (MUSTANG S® (333 MV/hr)), and monolith (SO3 Monolith (353 MV/hr)) with varying amount of the product loaded up to 1000 g/L CV or MV was evaluated at pH 5.5 and 3 mS/cm. As shown in FIG. 2, there was an over 93% monomer anti-CD11a antibody recovery for MUSTANG S®, Monolith SO3, and POROS® HS50 and about 88% monomer anti-CD11a antibody recovery for SPSFF.

The ability of the three types of cation exchange materials, resin (POROS® HS50 column (15.1 CV/hr or 75 cm/hr) and SPSFF column (15.7 CV/hr or 75 cm/hr)), membrane (MUSTANG S® (333 MV/hr)), and monolith (SO3 Monolith (353 MV/hr)) with varying amount of the product loaded up to 1000 g/L CV or MV to remove CHOP was evaluated at pH 5.5 and 3 mS/cm. As shown in FIG. 2, the monolith material, SO3 Monolith, was better at removing CHOP than the other two cation exchange materials. The membrane (MUSTANG S®) and the POROS® HS50 column were similar and better than the SPSFF column in removing CHOP. See FIG. 2.

Figure 3:
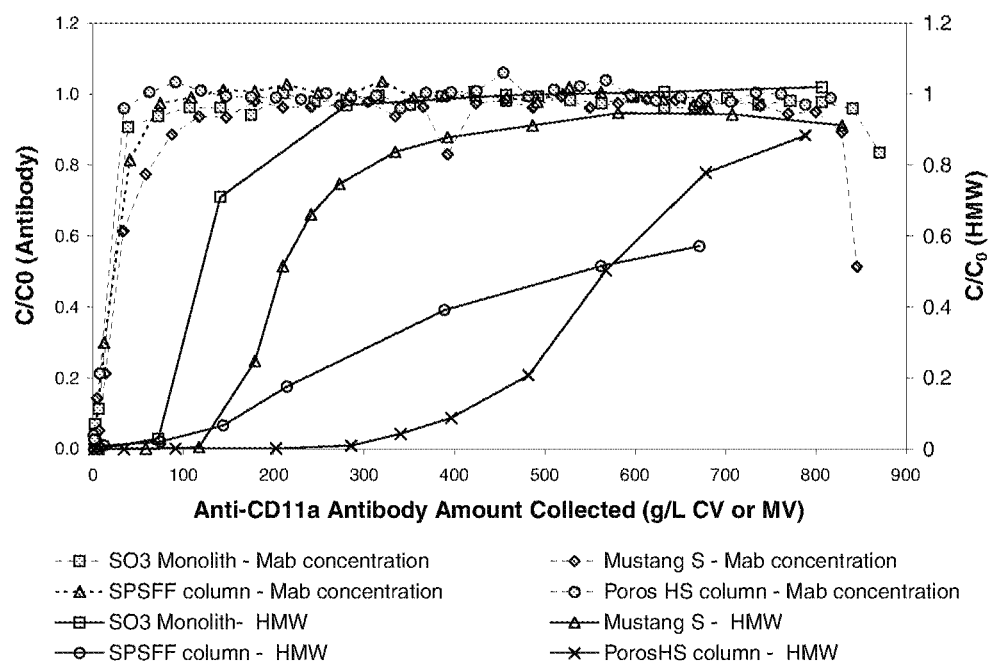
FIG. 3 shows $C/C_0$ (Mab concentration) and $C/C_0$ (the high molecular weight ("HMW") concentration) with varying amount of the product comprising anti-CD11a antibody collected (g/L CV or MV) using SO3 monolith, MUSTANG® S, SPSFF, and POROS® HS50. C is the Mab or HMW percentage in the collected fraction and $C_0$ is the Mab or HMW percentage in the load.
Figure 4A:
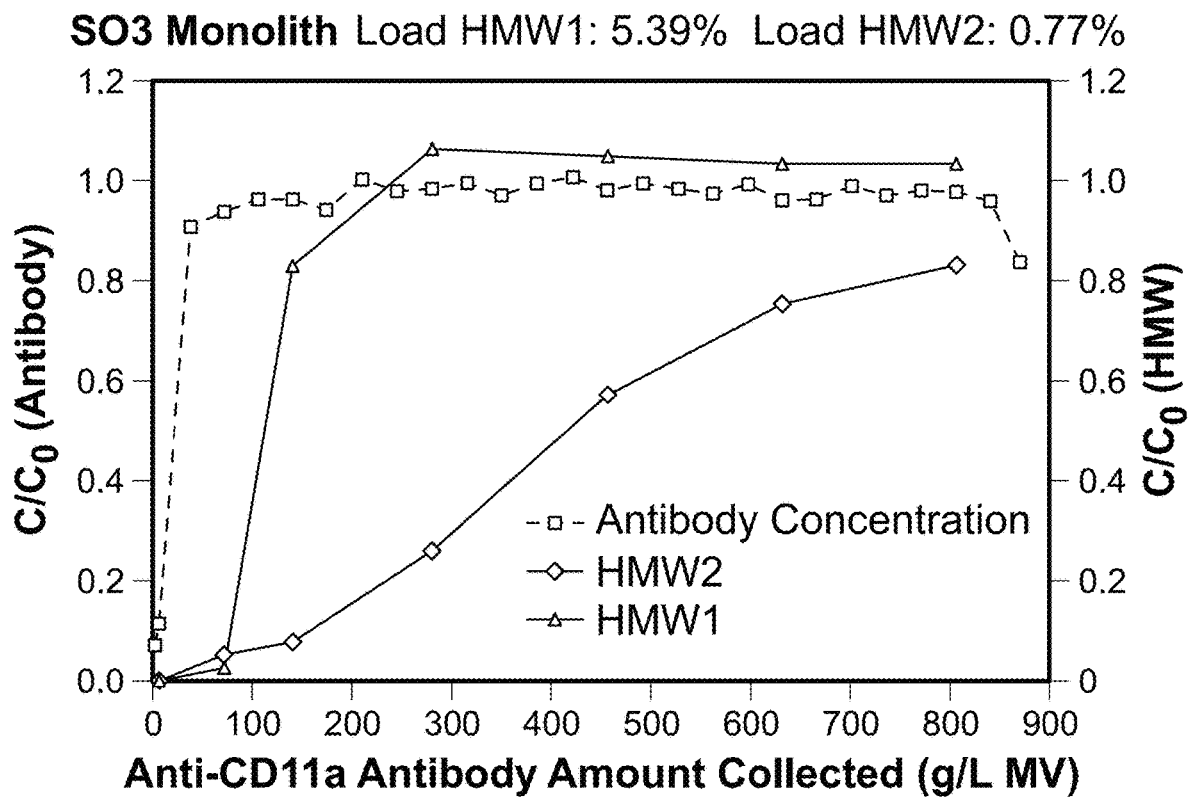
FIG. 4A-D show $C/C_0$ (Mab concentration), $C/C_0$ (HMW1 concentration) and $C/C_0$ (HMW2 concentration) with varying amount of the product comprising anti-CD11a antibody collected (g/L CV or MV) using SO3 monolith, MUSTANG® S, SPSFF, and POROS® HS50.
Figure 4B:
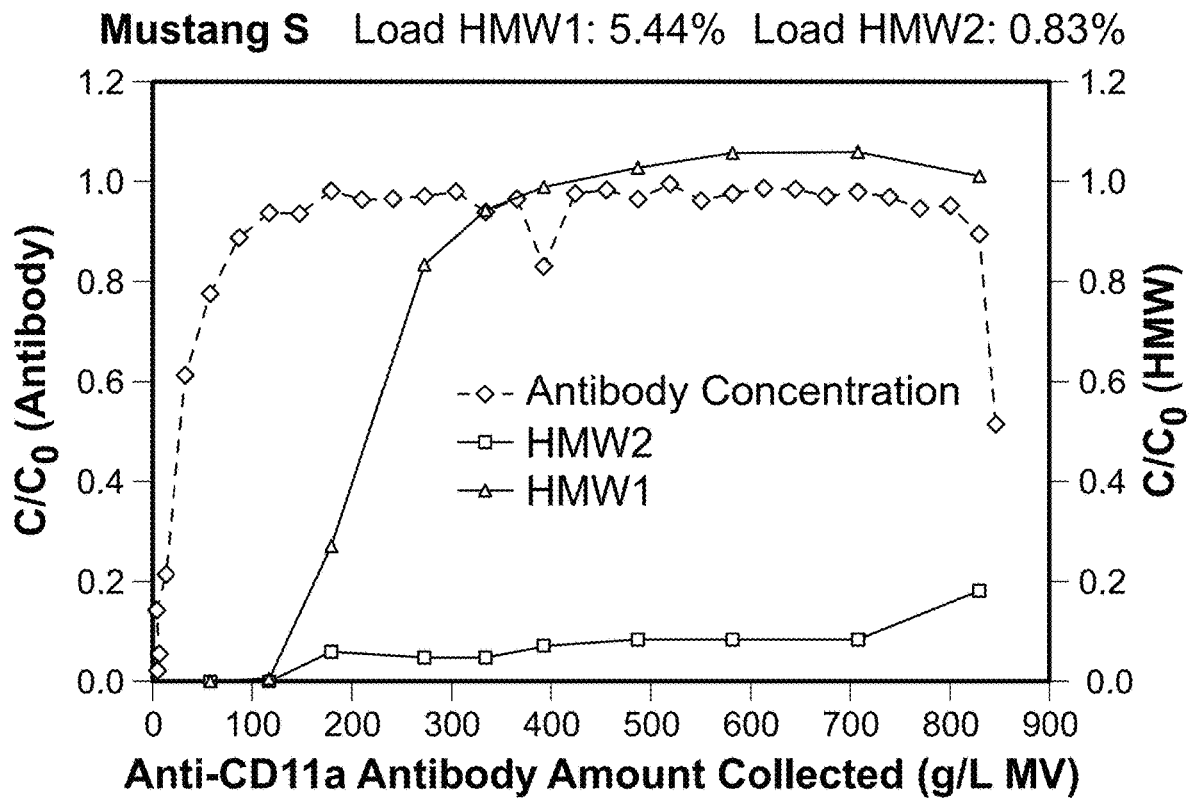
Figure 4C:
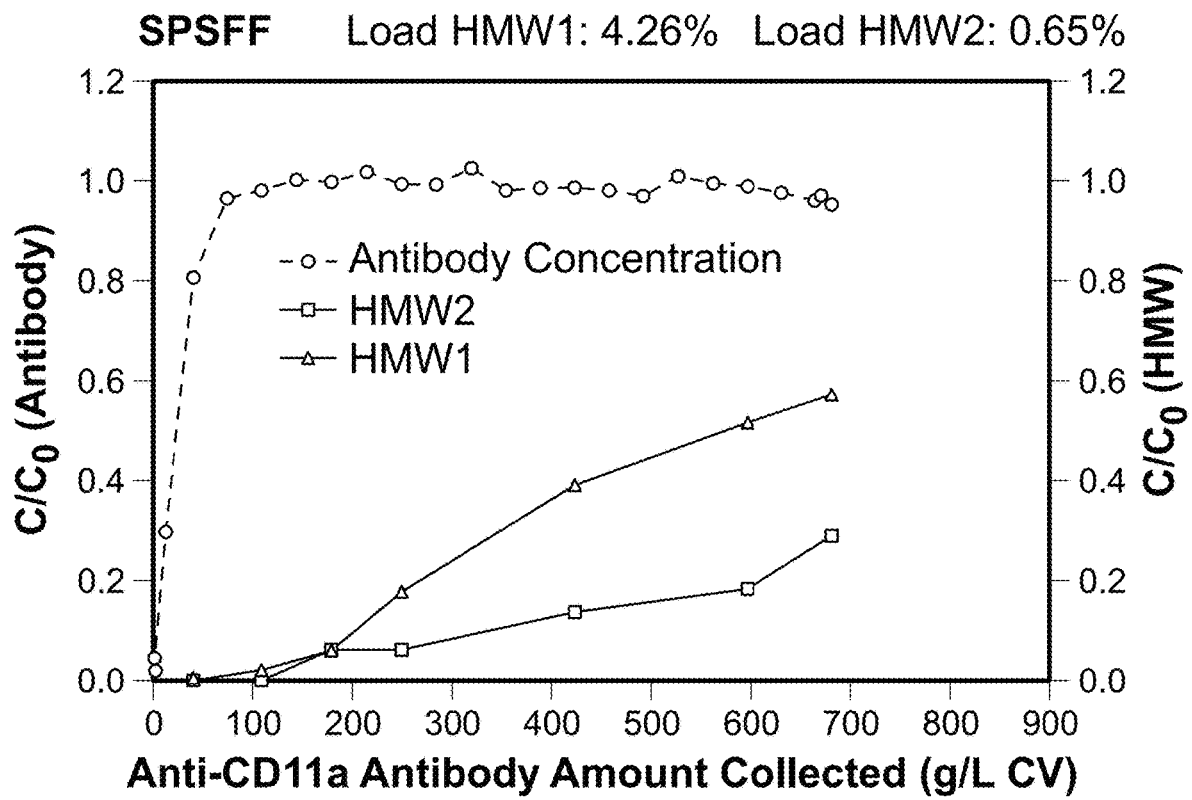
Figure 4D:
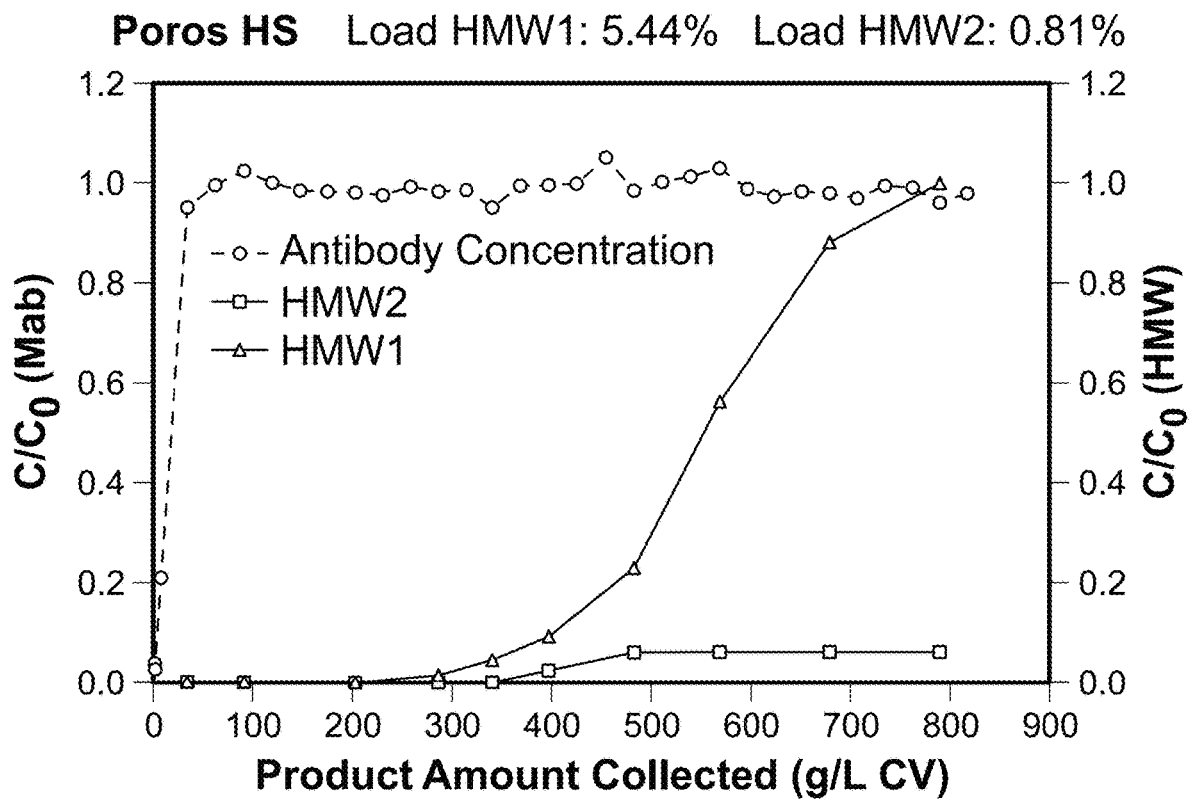

The ability of the three types of cation exchange materials, resin (POROS® HS50 column (15.1 CV/hr or 75 cm/hr) and SPSFF column (15.7 CV/hr or 75 cm/hr)), membrane (MUSTANG S® (333 MV/hr)), and monolith (SO3 Monolith (353 MV/hr)) with varying amount of the product loaded up to 1000 g/L CV or MV to remove HMW was evaluated at pH 5.5 and 3 mS/cm. As shown in FIG. 3, the resin cation exchange material, POROS® HS50, was most effective in removing HMW, followed by SPSFF. Further, MUSTANG S® was better than SO3 monolith in removing HMW. See FIG. 3.

The ability of the cation exchange materials, resin (POROS® HS50 column and SPSFF column), membrane (MUSTANG S®), and monolith (SO3 Monolith) with varying amount of the product loaded up to 1000 g/L CV or MV to remove HMW1 and HMW2 was also evaluated at pH 5.5 and 3 mS/cm. As shown in FIG. 4, POROS® HS50 and MUSTANG S® were more effective in removing HMW2.

Figure 5A:
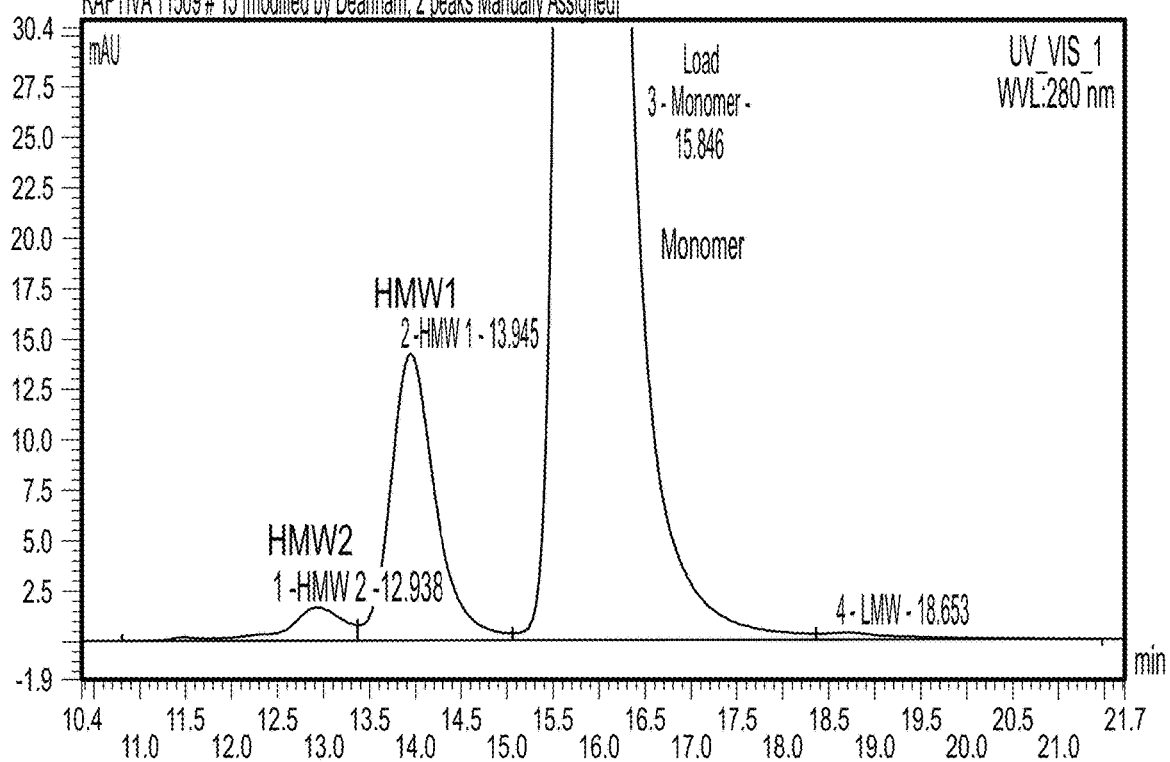
FIG. 5A shows the chromatogram of HMWs and Mab in the product comprising anti-CD11a antibody loaded using POROS® HS50.
Figure 5C:
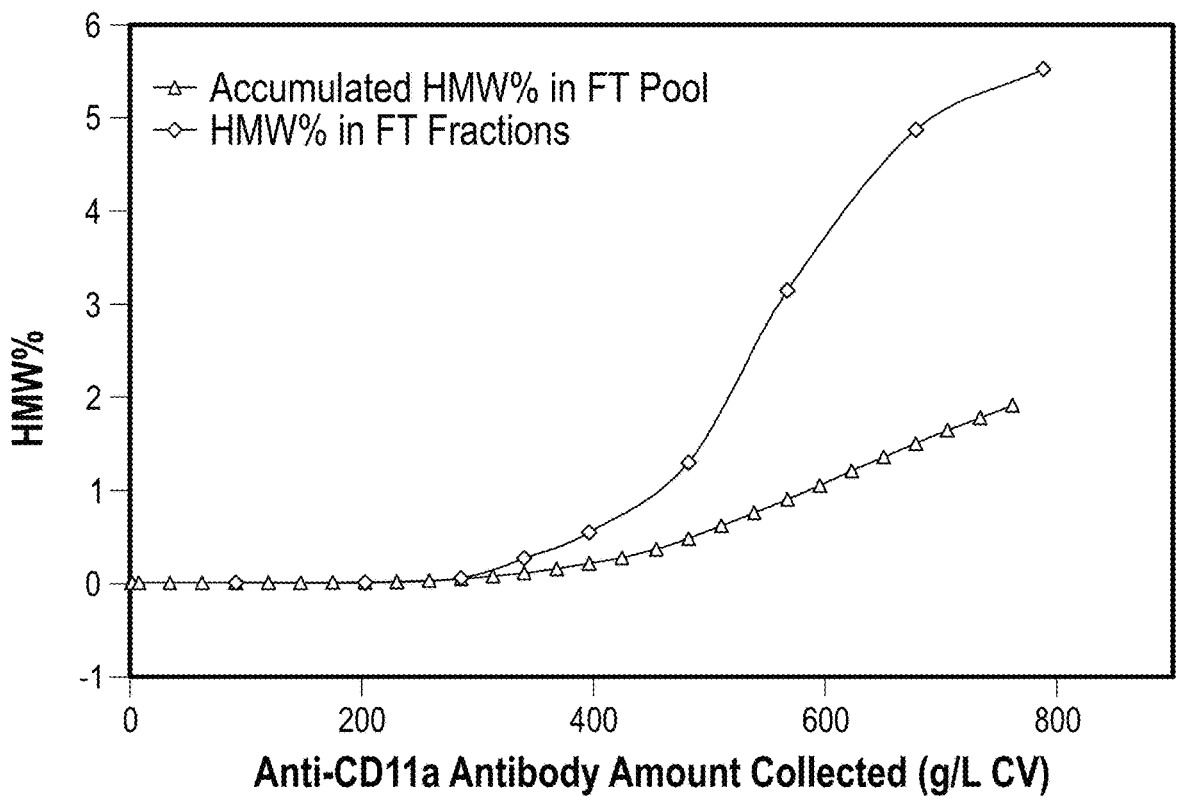
FIG. 5C shows the accumulated HMW % in the flow through ("FT") pool and the HMW % in the FT fractions with varying amount of the product comprising anti-CD11a antibody collected (g/L CV) using POROS® HS50.
Figure 5B:
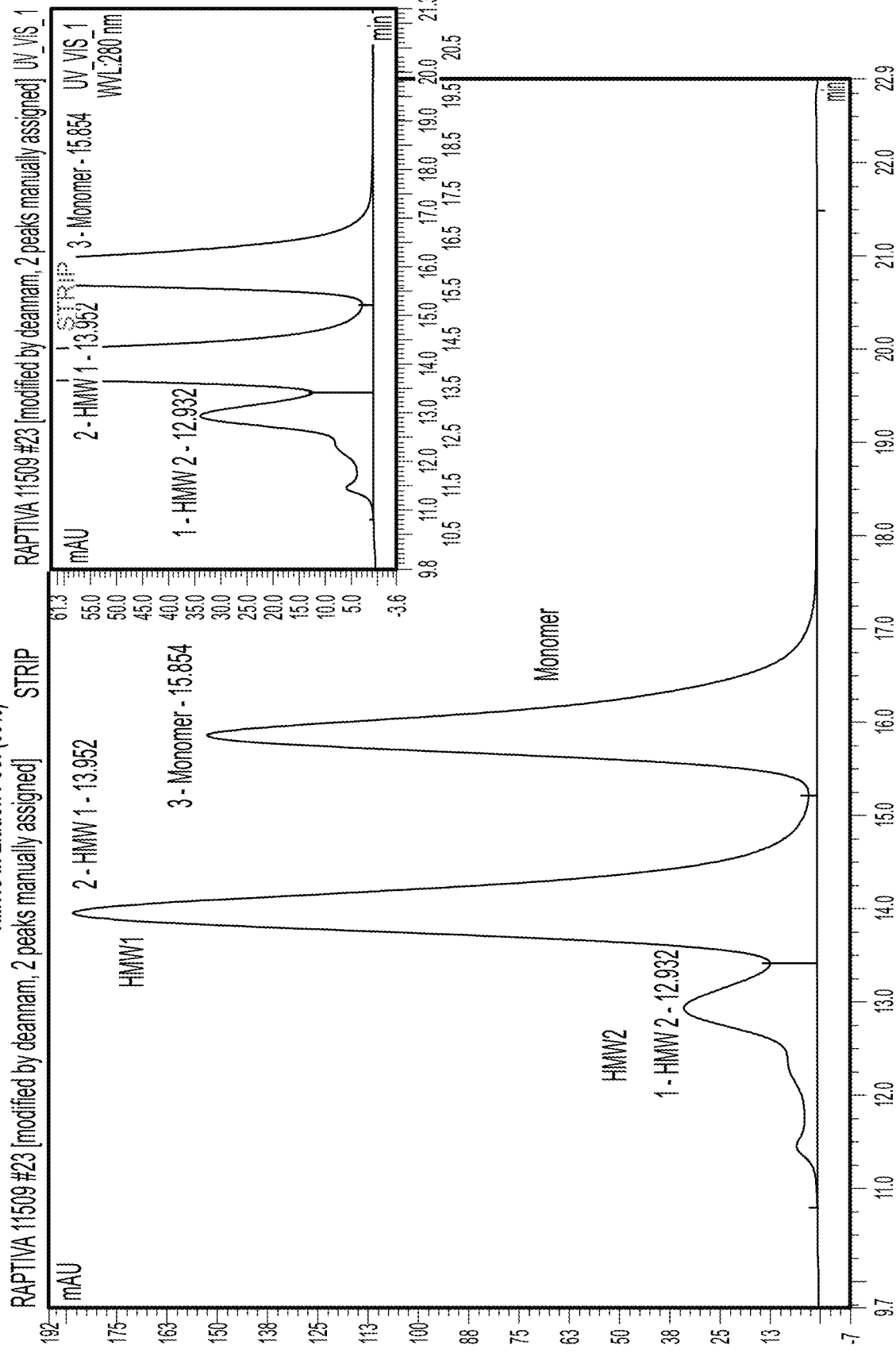
FIG. 5B shows the chromatogram of HMWs and Mab in the elution pool using POROS® HS50 (the inner figure shows an enlarged section of the peaks)

The ability of POROS® HS50 (15.1 CV/hr or 75 cm/hr) to remove HMW1 and HMW2 with the product loaded at varying amount up to 1000 mg/mL CV was examined at pH 5.5 and 3 mS/cm. The HMW was 6.26% and 60% in the load and in the elution pool, respectively. As shown in FIG. 5, POROS® HS50 was effective in removing both HMW1 and HMW2.

Figure 6A:
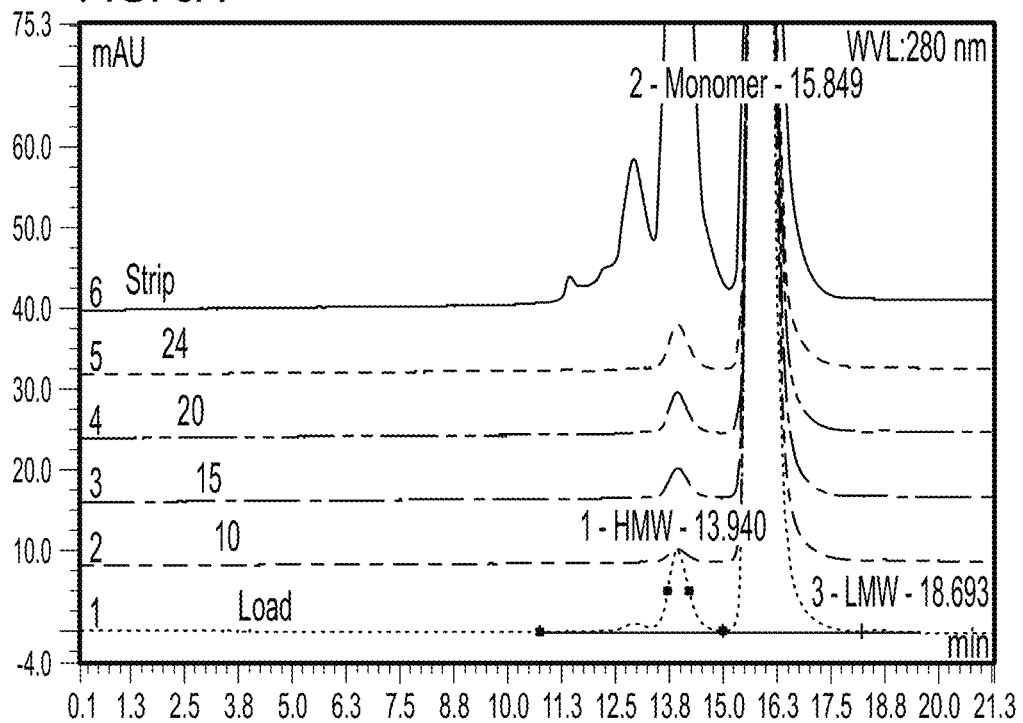
FIG. 6A shows the chromatograms of the FT pool with varying amount of the product comprising anti-CD11a antibody collected using SPSFF column.
Figure 6B:
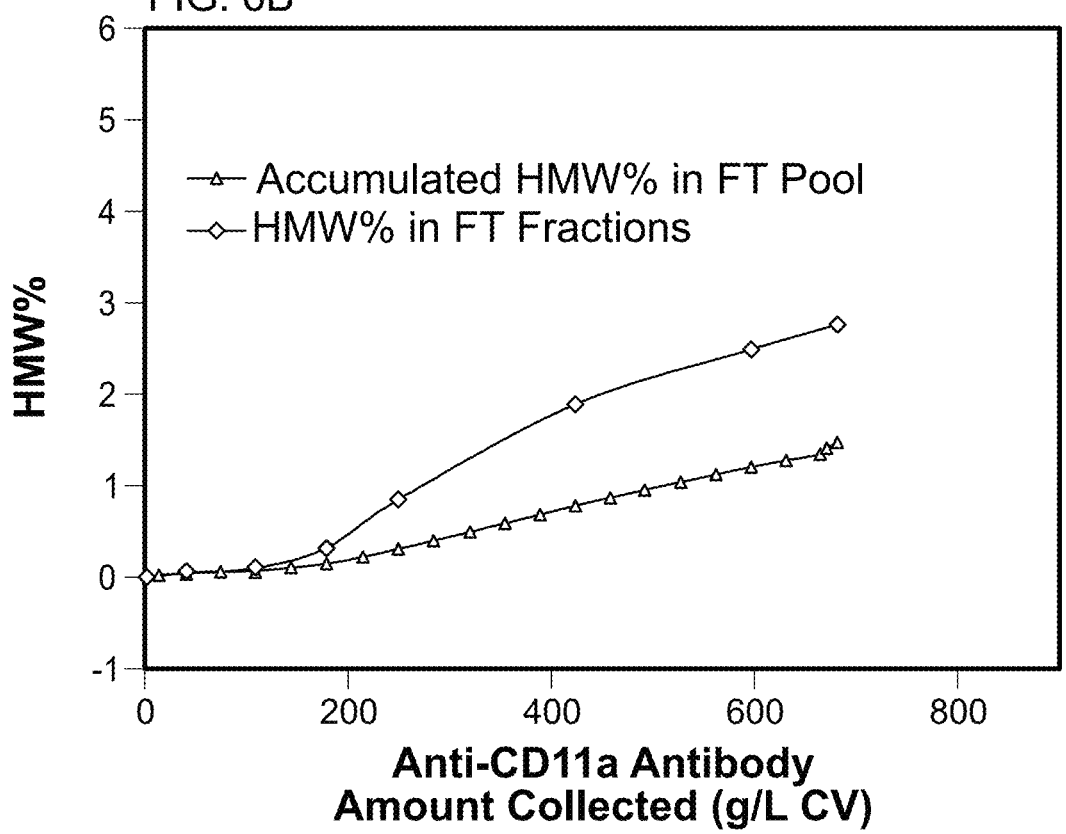
FIG. 6B shows the accumulated HMW % in the FT pool and the HMW % in the FT fractions with varying amount of the product comprising anti-CD11a antibody collected (mg/mL CV) using SPSFF.
Figure 7A:
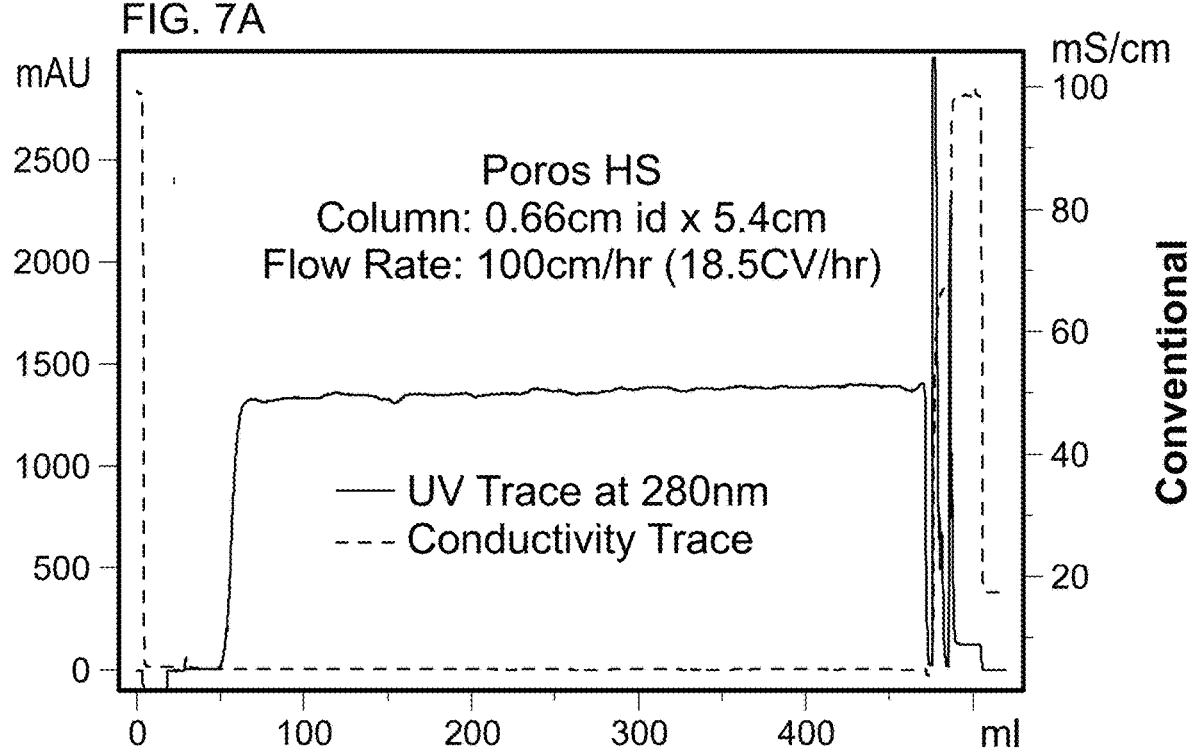
FIG. 7A-D show the chromatograms using POROS® HS50, SPSFF, SO3 Monolith, and MUSTANG® S for the purification of anti-VEGF antibody.
Figure 7B:
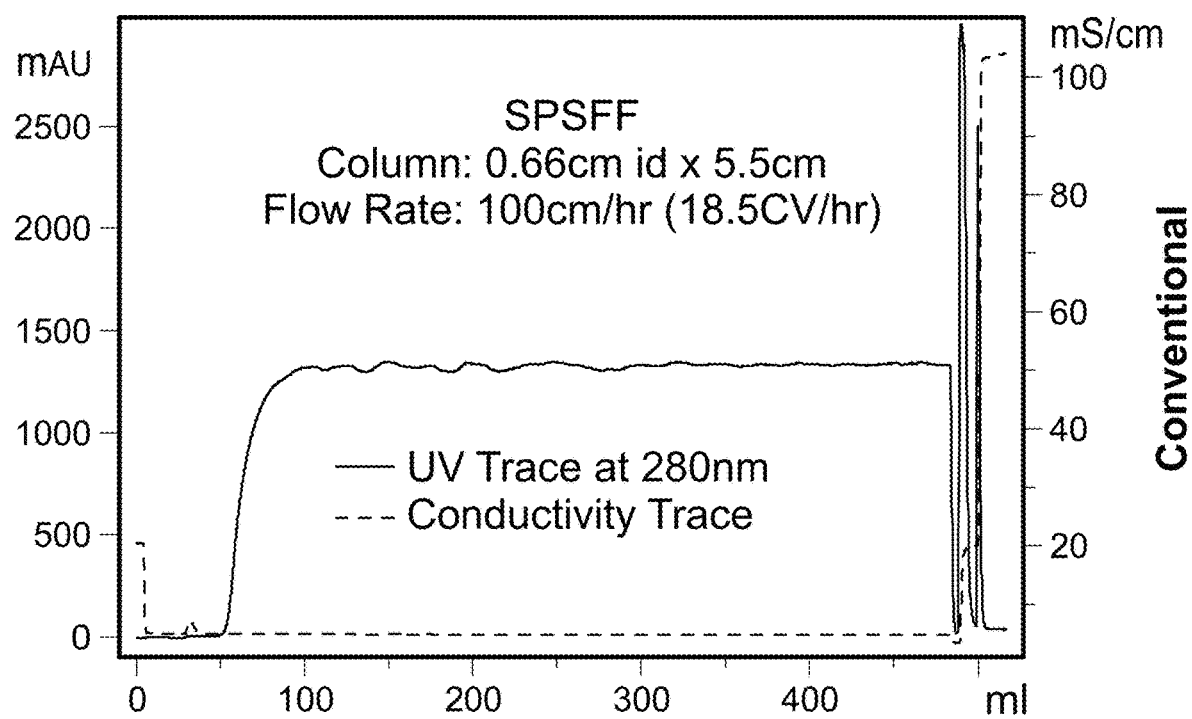
Figure 7C:
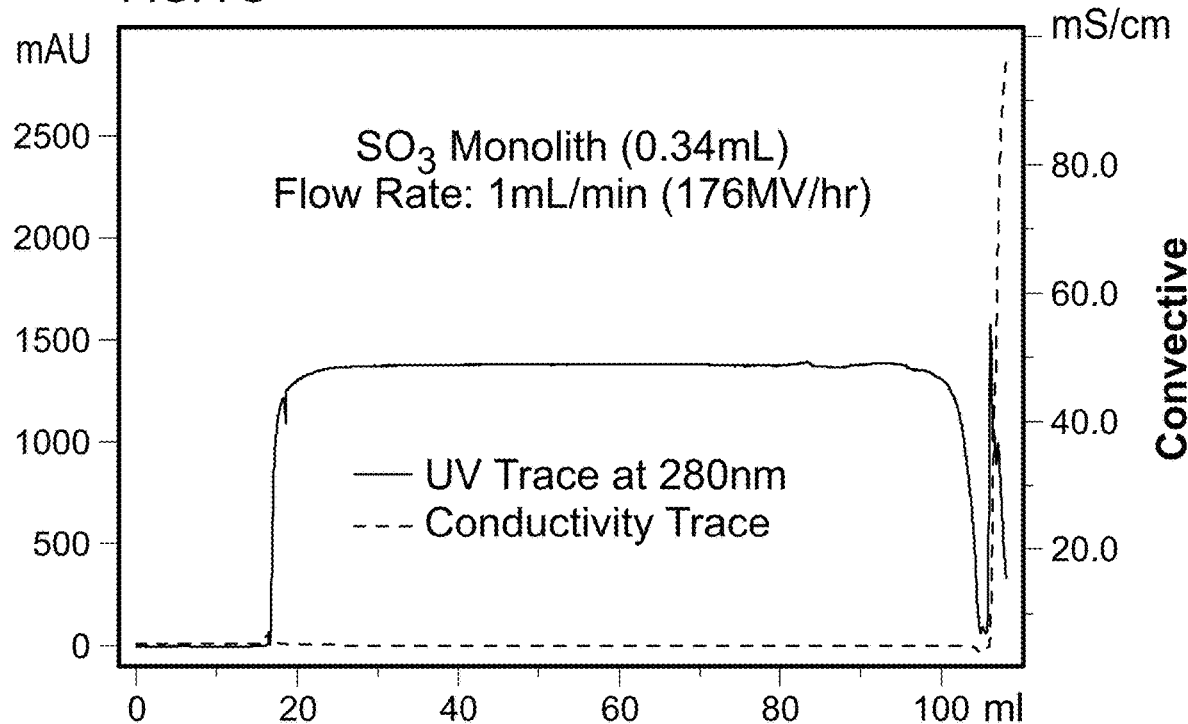
Figure 7D:
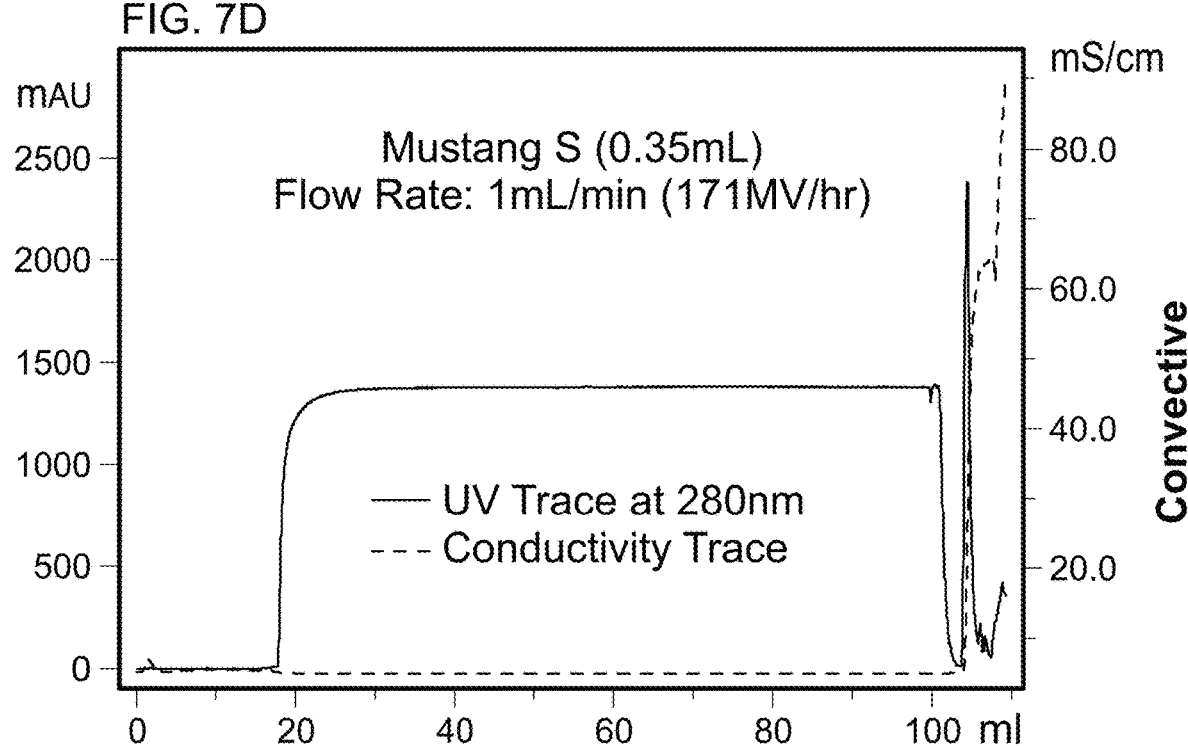

The ability of SPSFF to remove HMW was evaluated with the product loaded at varying amount of product up to about 800 g/L CV at pH 5.5 and 3 mS/cm. FIG. 6 shows the chromatograms and the HMW removal.

The performance of the three types of cation exchange materials, resin (POROS® HS50 column and SPSFF column), membrane (MUSTANG S®), and monolith (SO3 Monolith) were summarized in Table 2. The commercial process for purifying anti-CD11a used the bind-elute mode and the loading density of 15-44 mg/mL CV. As shown in Table 2, SO3 Monolith was most effective in removing CHOP and POROS® HS resin was most effective in removing HMWs. The overloaded POROS® HS process was similar in HMW and CHOP removals as the commercial SPSFF process. See Table 2.

TABLE 2

|  | In load (g/L) | Commercial SPSFF process | In CEX pool | | | |
| --- | --- | --- | --- | --- | --- | --- |
|  |  |  | Poros HS | SPSFF | Mustang S | SO$_3$ monolith |
| CHOP ppm | 600-900 in the commercial process; 600 in the present study | 72-183 | <150 | <400 | <150 | <60 |
| HMW % | ~5 in the commercial process; 6.2 in the present study | 0.2 | 0.4 500 g/L CV collected | 1 500 g/L CV collected | 2.7 500 g/L MV collected | 4.7 500 g/L MV collected |

Purification of Anti-VEGF Antibody

Three types of cation exchange materials were evaluated in this study: resin, membrane, and monolith. The overloaded cation exchange purification processes of anti-VEGF antibody using these three cation exchange materials were evaluated with respect to process performance (e.g., impurities removal, step yield, and product quality).

The chromatograms of the three types of cation exchange materials, resin (POROS® HS50 column (0.66 cm i.d.×5.4 cm, 18.5 CV/hr) and SPSFF column (0.66 cm i.d.×5.5 cm, 18.5 CV/hr)), monolith (SO3 Monolith (0.34 mL, 176 MV/hr)), and membrane (MUSTANG S® (0.35 mL, 171 MV/hr)), loaded with the product close to 1000 g/L CV or MV, were run at pH 5.5 and 5 mS/cm. See FIG. 7.

Figure 8:
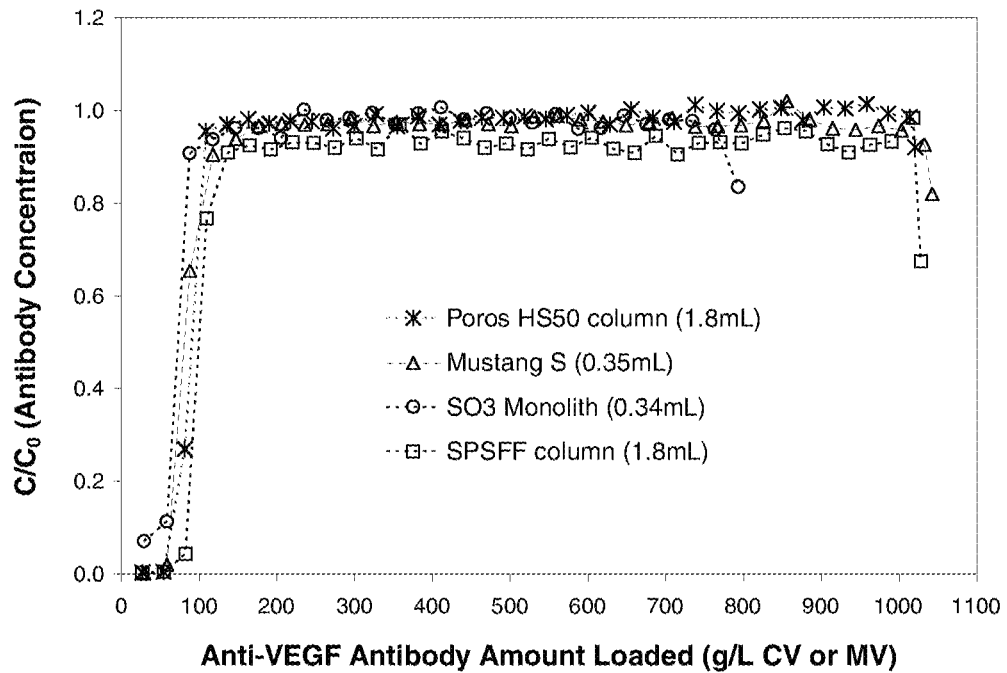
FIG. 8 shows $C/C_0$ (Mab concentration) of anti-VEGF antibody with varying amount of the product loaded (g/L CV or MV) using POROS® HS50, MUSTANG® S, SO3 monolith, and SPSFF.

The performance of the three types of cation exchange materials, resin (POROS® HS50 column (1.8 mL) and SPSFF column (1.8 mL)), membrane (MUSTANG S® (0.35 mL)), and monolith (SO3 Monolith (0.34 mL)), with varying amount of the product loaded between 0 and 1000 g/L CV or MV was evaluated at pH 5.5 and 5 mS/cm. For the membrane and monolithic chromatography, the flow rate used was 100-400 MV/hr. For the resins, the flow rate used was between 50-200 cm/hr (9-36 CV/hr). There was an over 90% monomer anti-VEGF antibody recovery using all cation exchange materials as shown in FIG. 8.

Figure 9:
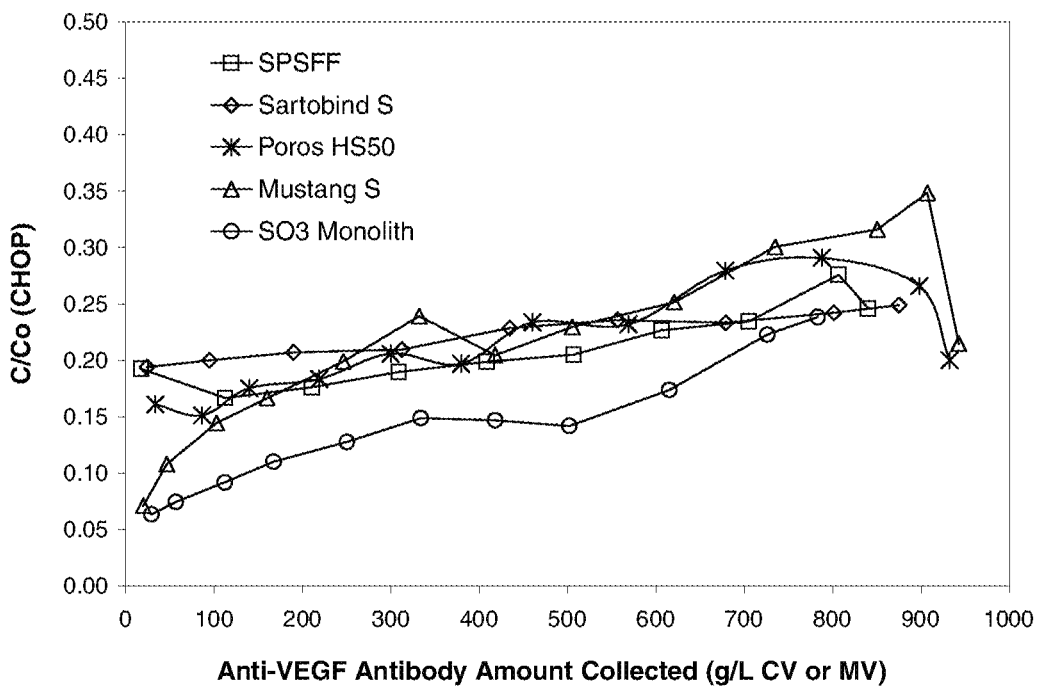
FIG. 9 shows $C/C_0$ (CHOP concentration) with varying amount of the product comprising anti-VEGF antibody collected (g/L CV or MV) using SPSFF, SARTOBIND® S, POROS® HS50, MUSTANG® S, and SO3 monolith.

The ability of the three types of cation exchange materials, resin (POROS® HS50 column (18 CV/hr and 1.7 mL) and SPSFF column (18 CV/hr and 1.7 mL)), membrane (MUSTANG S® (171 MV/hr) and SARTOBIND® S (120 MV/hr)), and monolith (SO3 Monolith (176 MV/hr)), with varying amount of the product loaded between 0 and 1000 g/L CV or MV to remove CHOP was valuated at pH 5.5 and 5 mS/cm. As shown in FIG. 9, the monolith, SO3 Monolith, was better at removing CHOP than the other two cation exchange materials. The resin (POROS® HS50 column and SPSFF column) and the membranes (MUSTANG S® and SARTOBIND® S) cation exchange materials were similar in removing CHOP. See FIG. 9.

Figure 10:
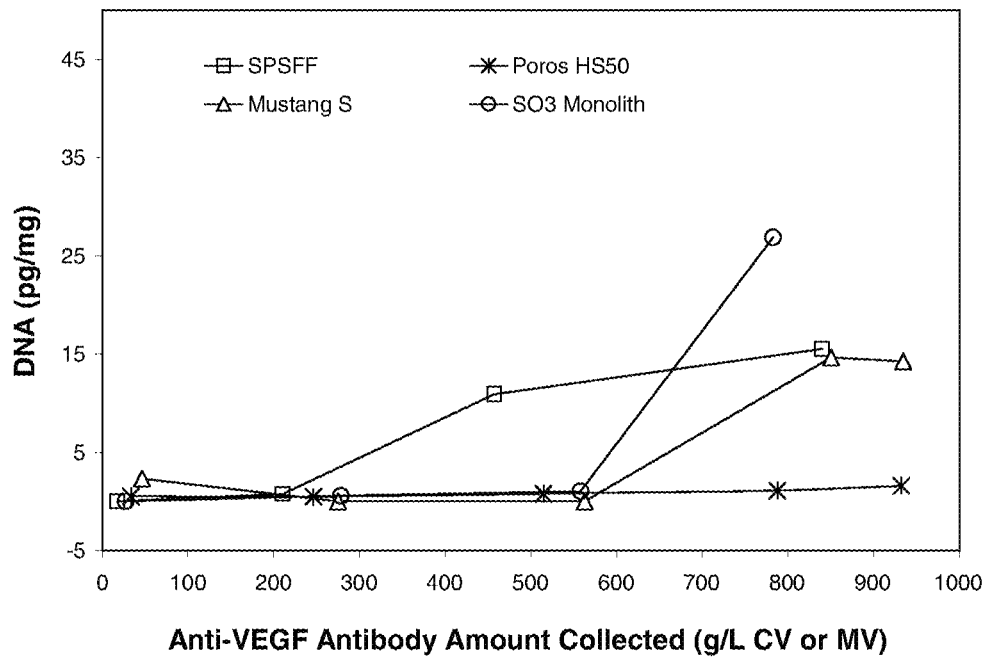
FIG. 10 shows the amount of DNA (pg/mg) with varying amount of the product comprising anti-VEGF antibody collected (g/L CV or MV) using SPSFF, POROS® HS50, MUSTANG® S, and SO3 monolith.

The ability of the three types of cation exchange materials, resin (POROS® HS50 column (18 CV/hr) and SPSFF column (18 CV/hr)), membrane (MUSTANG S® (171 CV/hr)), and monolith (SO3 Monolith (176 CV/hr)), with varying amount of the product loaded between 0 and 1000 g/L CV or MV to remove DNA was evaluated at pH 5.5 and 5 mS/cm. The resin cation exchange material POROS® HS50 was most effective in removing DNA. See FIG. 10.

Figure 11:
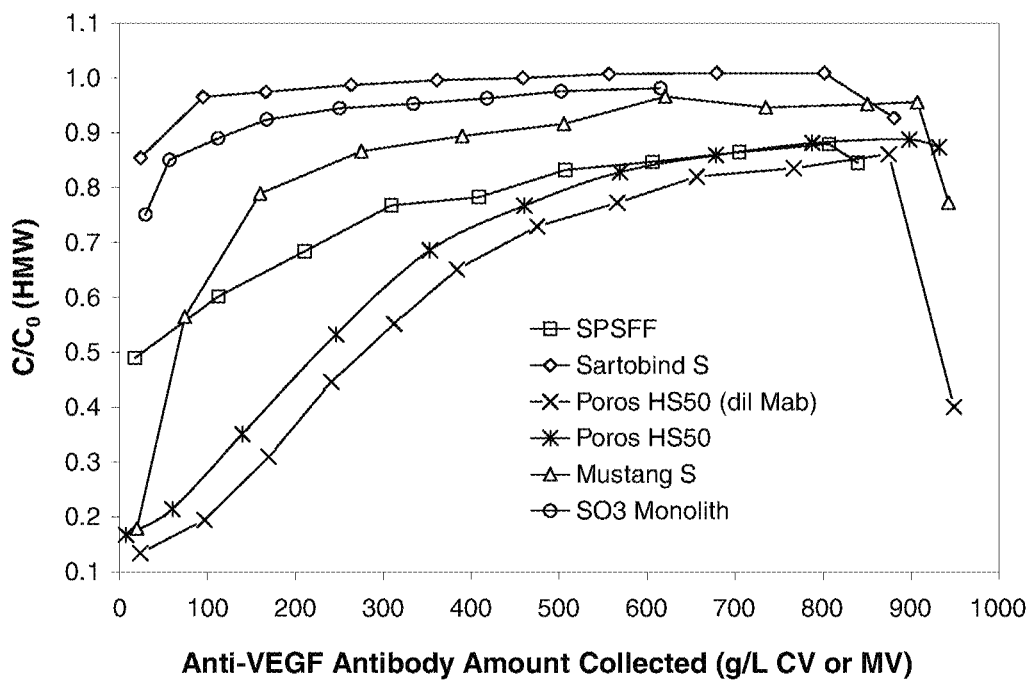
FIG. 11 shows $C/C_0$ (HMW concentration) with varying amount of the product comprising anti-VEGF antibody collected (g/L CV or MV) using SPSFF, SARTOBIND® S, POROS® HS50 with dilute Mab, POROS® HS50, MUSTANG® S, and SO3 monolith.

The ability of the three types of cation exchange materials, resin (POROS® HS50 column (18 CV/hr), POROS® HS50 column (18 CV/hr) with 1:2 diluted monomer antibody ("Mab"), and SPSFF column (18 CV/hr)), membrane (MUSTANG S® (176 MV/hr) and SARTOBIND® S (120 MV/hr)), and monolith (SO3 Monolith (171 MV/hr)), with varying amount of the product loaded between 0 and 1000 g/L CV or MV to remove HMW was valuated at pH 5.5 and 5 mS/cm. As shown in FIG. 11, the resin cation exchange material, POROS® HS50, was most effective in HMW removal followed by SPSFF. Further, MUSTANG S® was better than SO3 monolith in removing HMW. See FIG. 11.

Figure 12B:
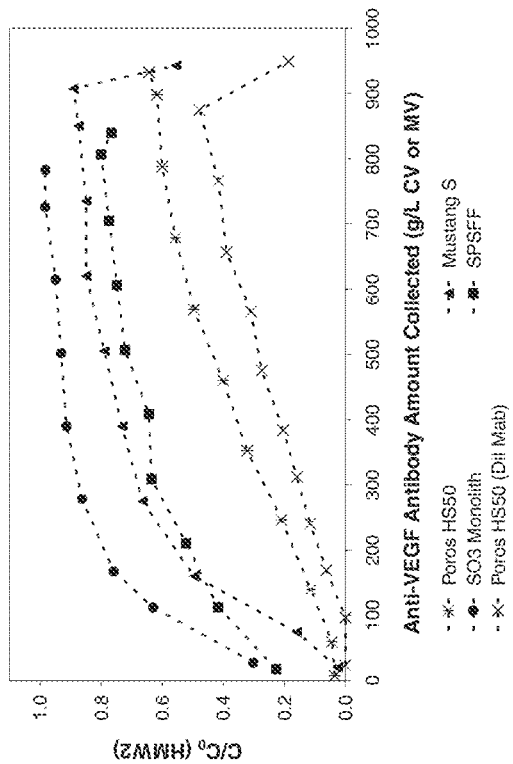
FIG. 12A-B show $C/C_0$ (HMW1 concentration) and $C/C_0$ (HMW 2 concentration) with varying amount of the product comprising anti-VEGF antibody collected (g/L CV or MV) using SPSFF, POROS® HS50 with dilute Mab, POROS® HS50, MUSTANG® S, and SO3 monolith.
Figure 12A:
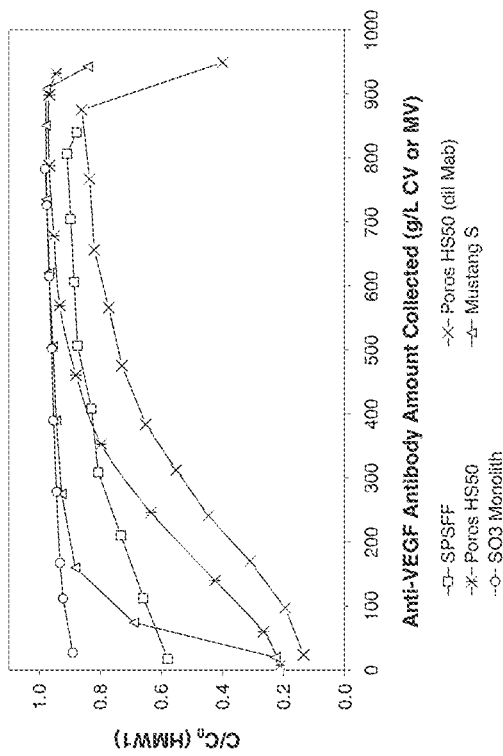

The ability of the cation exchange materials, resin (POROS® HS50 column(18 CV/hr), POROS® HS50 column (18 CV/hr) with diluted Mab, and SPSFF column (18 CV/hr)), membrane (MUSTANG S® (176 MV/hr)), and monolith (SO3 Monolith (171 MV/hr)) with varying amount of the product loaded between 0 and 1000 g/L CV or MV to remove HMW1 and HMW2 was also evaluated at pH 5.5 and 5 mS/cm. As shown in FIG. 12, the HMW2 removal was generally more effective than the HMW1 removal. See FIG. 12.

The dynamic binding capacity ("DBC") of the three types of cation exchange materials, resin (SPSFF column (1.88 mL) and POROS® HS50 column (1.85 mL)), membrane (MUSTANG S® coin (0.35 mL) and MUSTANG S® (Acrodisc 0.18 mL)), and monolith (SO3 Monolith disk (0.34 mL-1 disk) and SO3 Monolith disk (0.68 mL-2 disks)) at pH 5.5 and 5 mS/cm using multiple flow rates was evaluated. As described and shown in Table 3, the cation exchange resin had better Mab binding capacities than the membrane and monolith. In general, the Mab binding capacity of the cation exchange materials correlated with their ability of removing HMW. See FIG. 11 and Table 3. POROS® HS50 showed better mass transport than SPSFF. See Table 3. POROS® HS50 showed a higher DBC than MUSTANG S® and Monolith SO3. See Table 3.

TABLE 3

| Flow rate | | DBC at 5% BT |
|---|---|---|
| SPSFF (0.66 cm i.d. × 5.5 cm = 1.88 mL) | | |
| 9.1 CV/hr | 50 cm/hr | 67.2 |
| 18.2 CV/hr | 100 cm/hr | 52.6 |
| 36.4 CV/hr | 200 cm/hr | 41.0 |
| 54.5 CV/hr | 300 cm/hr | 30.7 |
| Poros 50HS (0.66 cm i.d. × 5.4 cm = 1.85 mL) | | |
| 9.3 CV/hr | 50 cm/hr | 55.7 |
| 18.5 CV/hr | 100 cm/hr | 51.4 |
| 37 CV/hr | 200 cm/hr | 47.4 |
| 55.6 CV/hr | 300 cm/hr | 44.3 |
| Mustang S coin 0.35 mL 21.9 | | |
| 171.4 CV/hr | 1 mL/min | |
| Mustang S (Acrodisc) 0.18 mL 20.6 | | |
| 171.4 CV/hr | 1 mL/min | |
| Monolith SO3 disk (0.34 mL - 1 disk) 17.5 | | |
| 88.2 CV/hr | 0.5 mL/min | |
| 176.5 CV/hr | 1 mL/min | 17.8 |
| Monolith SO3 disk (0.68 mL - 2 disk) 17.6 | | |
| 88.2 CV/hr | 1 mL/min | |

Purification of Anti-CD20 Antibody

The ability of various types of cation exchange resin (POROS® HS50, SE HiCap, SPSFF, SPXL and CAPTO S™) to remove HMW was evaluated using high throughput 96-well plates and batch binding mode with the product loaded at 70-90 mg/mL resin under various pHs and salt concentrations for the purification of an anti-CD20 antibody. The HMW removal was evaluated by the % HMW bound on the resin. As shown in FIG. 13, POROS® HS50 was most effective in removing HMW, followed by SE HiCap. Further, SPSFF was better than SPXL in removing HMW. See FIG. 13. Moreover, SPXL was similar to CAPTO S™ in removing HMW. See FIG. 13.

The ability of various types of resin (POROS® HS50, SE HiCap, SPSFF, SPXL and CAPTO S™) to remove CHOP was evaluated using high throughput 96-well plates with the product loaded at 70-90 mg/mL resin under various pHs and salt concentrations. The CHOP removal was evaluated by the % CHOP bound on the resin. As shown in FIG. 14, POROS® HS50 was most effective in removing CHOP, followed by SE HiCap. Further, SPSFF was better than SPXL in removing CHOP. See FIG. 14. Moreover, SPXL was better than CAPTO S™ in removing CHOP. See FIG. 14.

Figure 15:
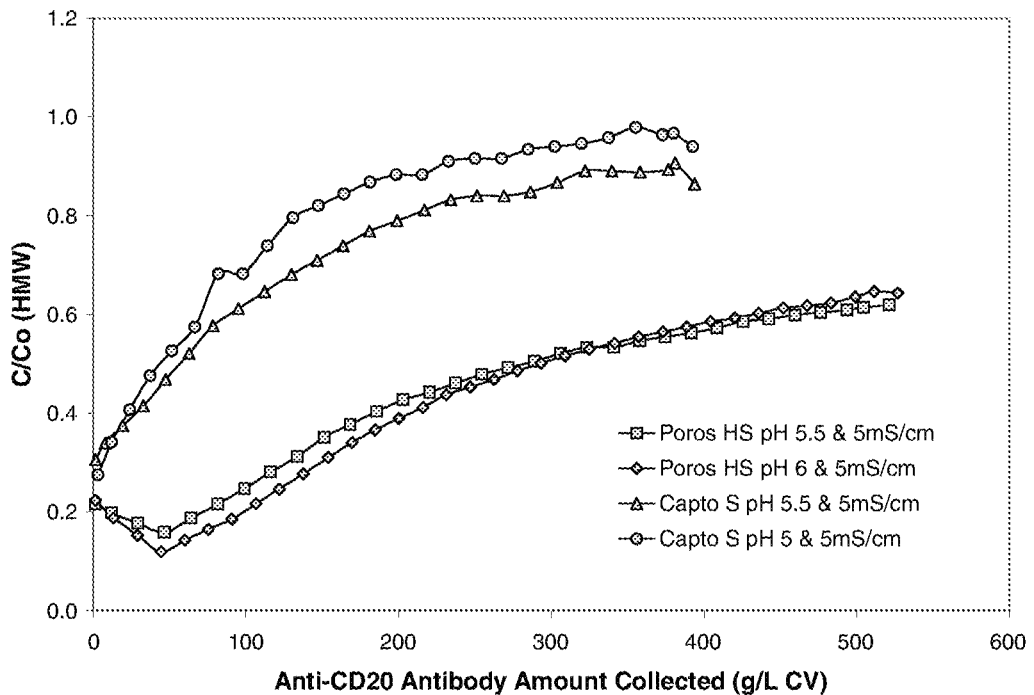
FIG. 15 shows $C/C_0$ (HMW concentration %) with varying amount of the product comprising anti-CD20 antibody collected (g/L CV) using POROS® HS50 and CAPTO S™.
Figure 16:
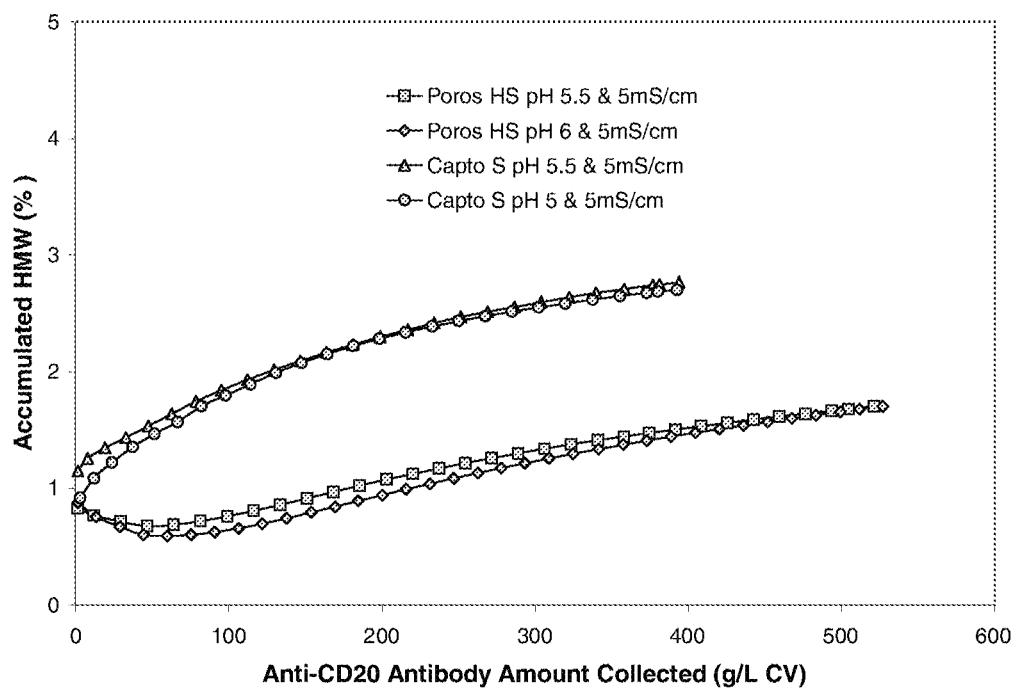
FIG. 16 shows accumulated HMW (%) with varying amount of the product comprising anti-CD20 antibody collected (g/L CV) using POROS® HS50 and CAPTO S™.

The ability of POROS® HS50 and CAPTO S™ resins to remove HMW was further examined using column chromatography with the varying amount of the product loaded at 5 mS/cm and different pHs (POROS® HS50 at pH 5.5 and pH 6 and CAPTO S™ at pH 5 and pH 5.5). As shown in FIG. 15, POROS® HS50 was better than CAPTO S™ in binding HMWs. The accumulated HMW % was lower in the collected product pools from the runs on POROS® HS50 resin than in the collected product pools from the runs on CAPTO S™ resin. See FIG. 16.

Figure 17:
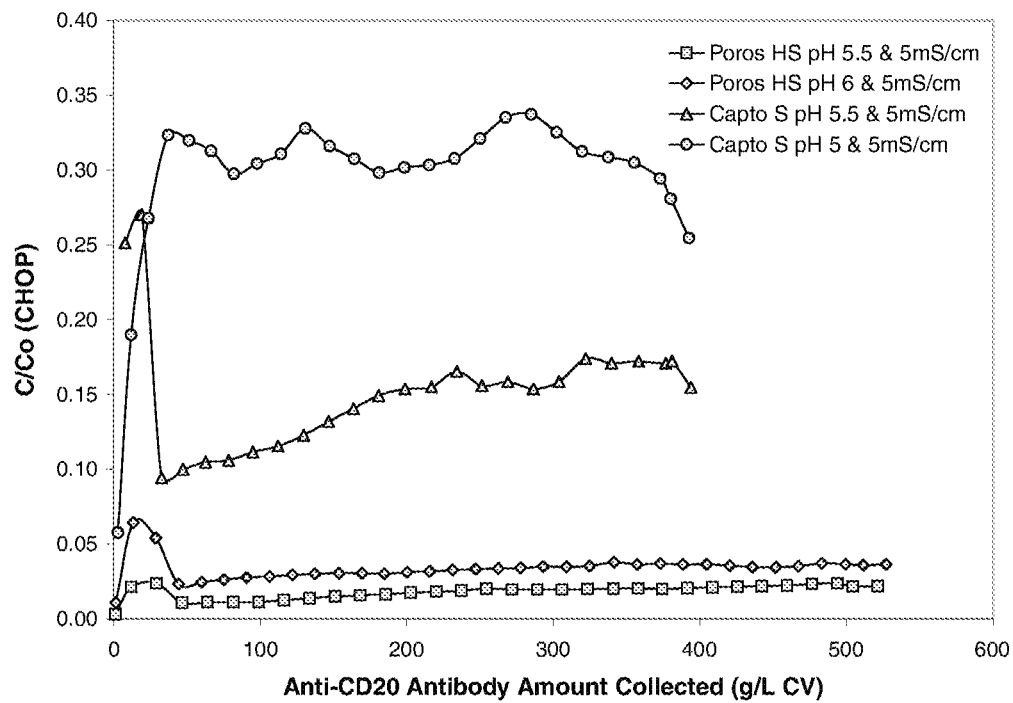
FIG. 17 shows $C/C_0$ (CHOP concentration) with varying amount of the product comprising anti-CD20 antibody collected (g/L CV) using POROS® HS50 and CAPTO S™.
Figure 18:
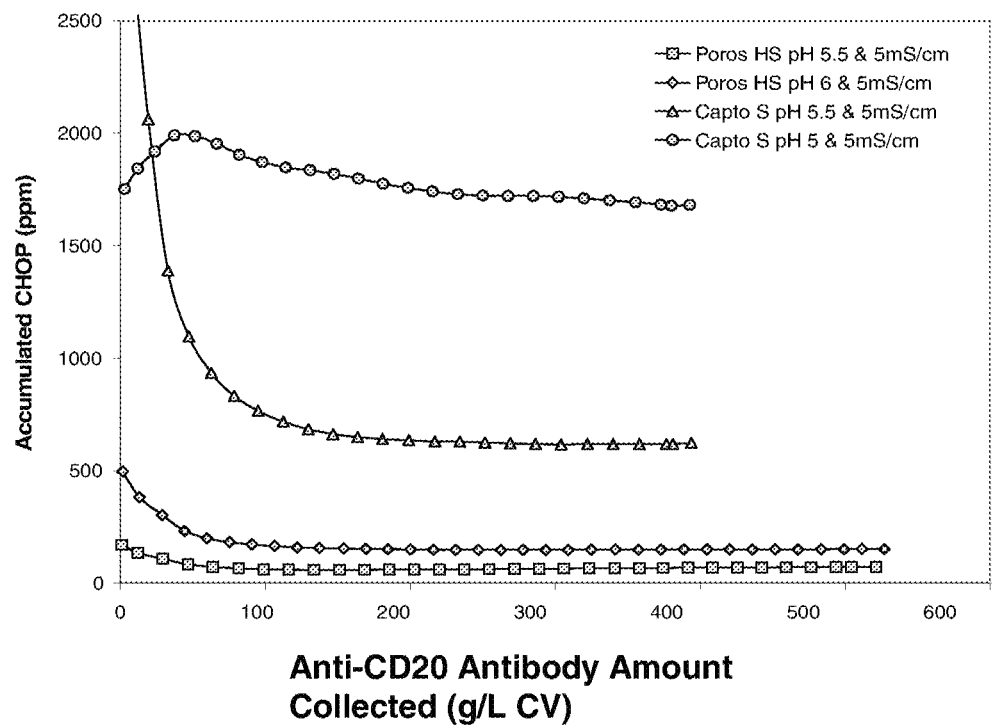
FIG. 18 shows accumulated CHOP (ppm) with varying amount of the product comprising anti-CD20 antibody collected (g/L CV) using POROS® HS50 and CAPTO S™.

The ability of POROS® HS50 and CAPTO S™ resins to remove CHOP was also examined using column chromatography with the varying amount of the product loaded at 5 mS/cm and different pHs (POROS® HS50 at pH 5.5 and pH 6 and CAPTO S™ at pH 5 and pH 5.5). As shown in FIG. 17, POROS® HS50 was better than CAPTO S™ in binding CHOP. The accumulated CHOP was lower in the collected product pools from the runs on POROS® HS50 resin than in the collected product pools from the runs on CAPTO S™ resin. See FIG. 18.

Example 2—Overloaded Cation Exchange Chromatography Using Various Purification Conditions This example describes an overloaded cation exchange chromatography process for purifying antibodies.

Materials and Methods

Purification Methods

The filtered and equilibrated protein pools were prepared as described in Example 1 and used as the product for the cation exchange chromatography.

The columns were packed with POROS® HS50 or SPSFF or CAPTO S™ resin, respectively. The column dimensions were 0.66 cm i.d. by 5 to 15 cm bed height. The flow rates used were 50-200 cm per hour (9-36 column volume (CV) per hour). Chromatography was monitored at 280 nm and performed at room temperature.

To avoid exclusion of antibody from chromatography resin, for example, the optimized loading conductivity is 4-6 mS/cm at pH 5-6, under which the maximum dynamic binding capacity can be obtained. The conductivity of 5-6 mS/cm and pH of 5.0-5.5 was used at the loading condition on the cation exchange columns in the first group study.

The product as determined by 280 nm was loaded up to 1000 g/L of column volume during each run. A wash step using the matrix equilibration buffer was applied immediately following the loading step until the UV trace returned to the baseline. An elution step with a higher salt concentration solution was used to strip out the bound species from the matrix during each chromatographic run. The bound species contained unwanted HMW species, DNA, CHOP, and other impurities. Columns were cleaned with 0.5N NaOH solution after each run and stored in 0.1N NaOH solution.

During the loading and washing steps, the flow through from each run was fractionated and collected in appropriate size cornical tubes. The protein concentration in each fraction was measured using UV-Vis spectrophotometer. The impurity contents such as host cell protein, DNA, leached protein A, and gentamicin were determined in selected fractions to cover the entire loading and washing steps as discussed above.

Experimental Procedures and Results

Purification of Anti-VEGF Antibody using SPSFF

Figure 19A:
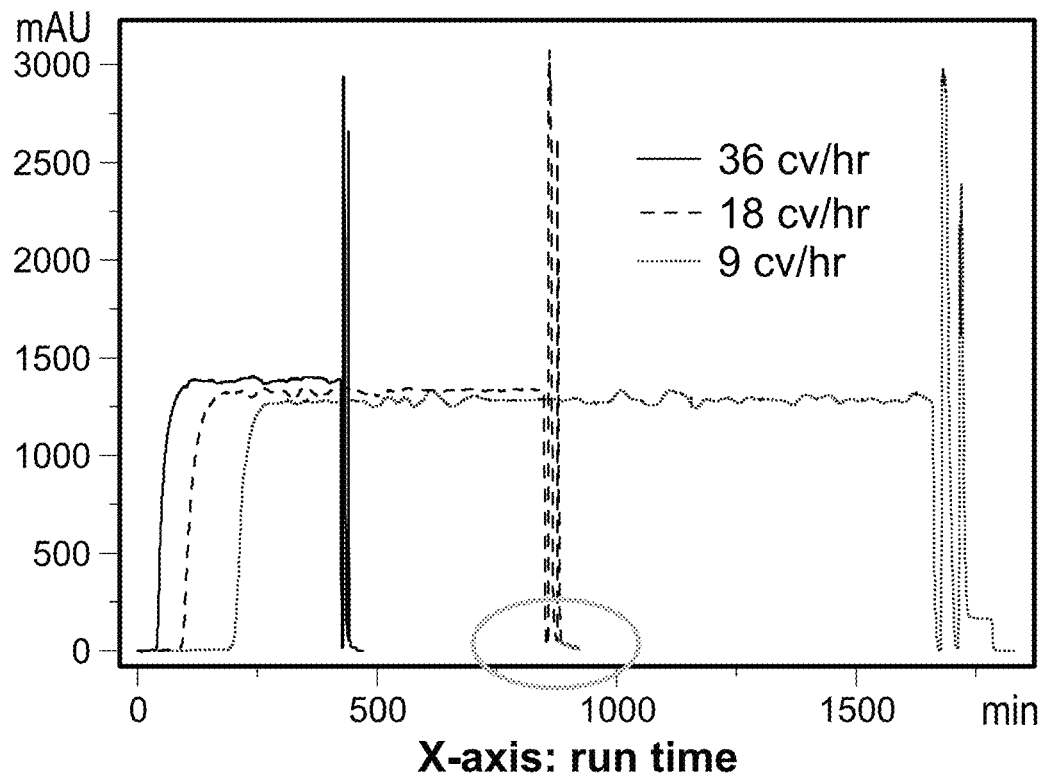
FIGS. 19A-19B show the chromatograms of the UV trace obtained at 280 nm plotted over run time (FIG. 19A) and over product loading volume (FIG. 19B) using SPSFF under various flow rates for the purification of anti-VEGF antibody.
Figure 19B:
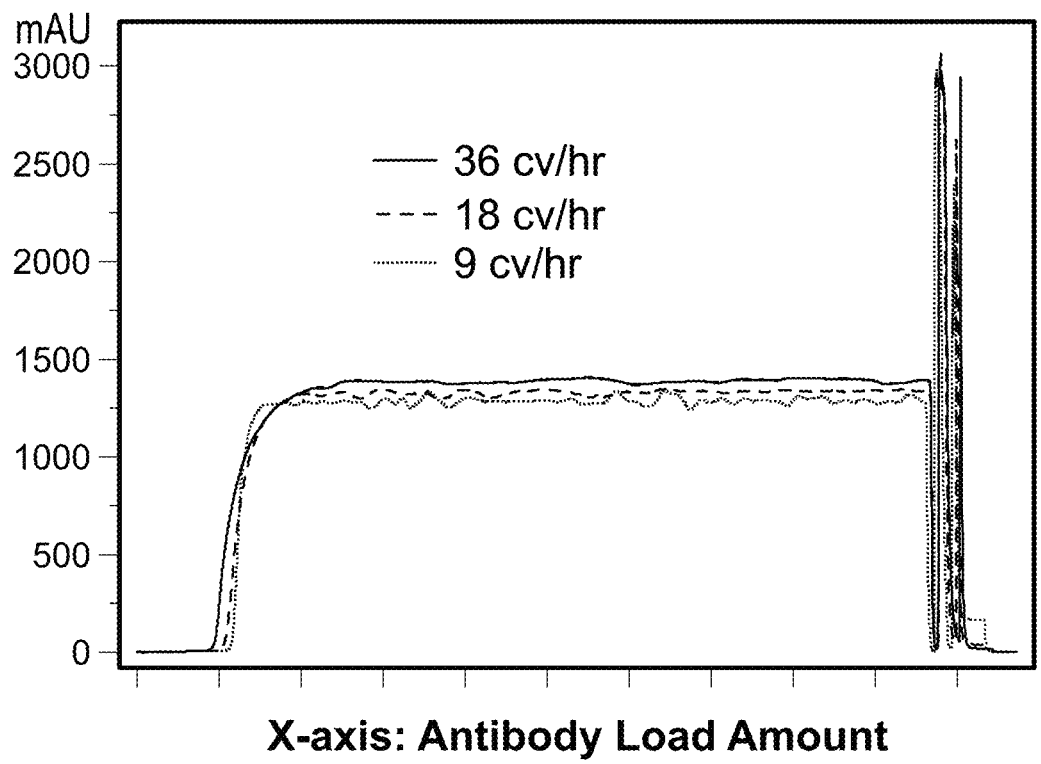

The chromatograms of SPSFF (0.66 cm id×5.5 cm bed height) with the product loading amount of up to 1000 mg/mL CV were run under various flow rates (9 CV/hr, 8 CV/hr, and 36 CV/hr) at pH 5.5, 5 mS/cm in NaAC. See FIG. 19.

Figure 20:
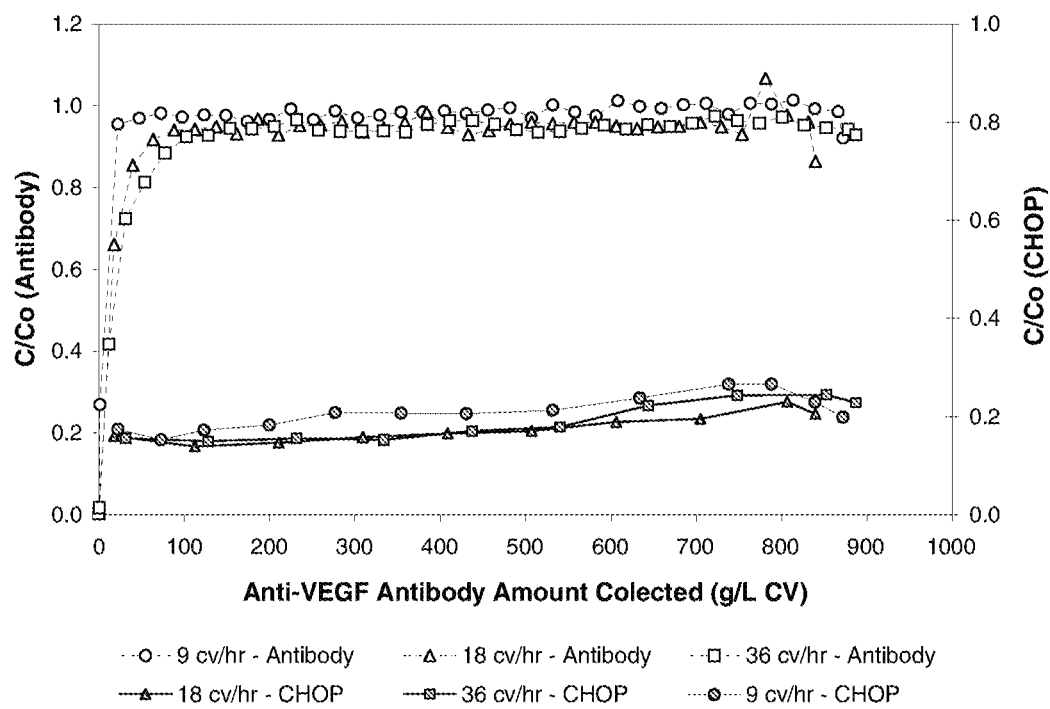
FIG. 20 shows $C/C_0$ (Mab concentration) and $C/C_0$ (CHOP concentration) with varying amount of the product comprising anti-VEGF antibody collected (mg/mL CV) using SPSFF under various flow rates.
Figure 21:
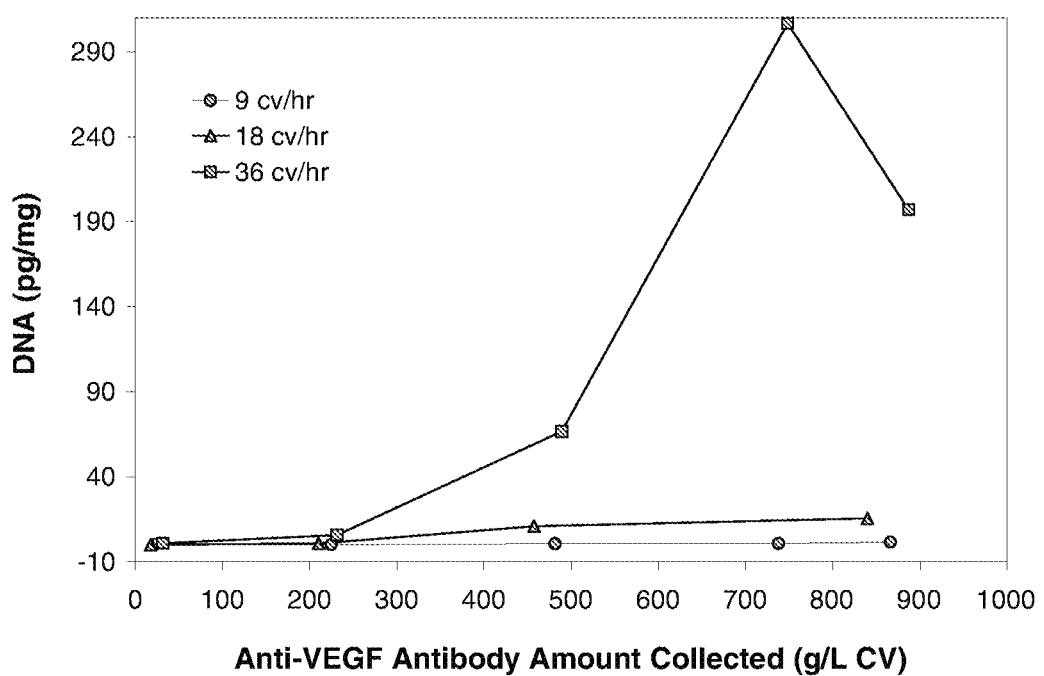
FIG. 21 shows the amount of DNA (pg/mg) with varying amount of the product comprising anti-VEGF antibody collected (mg/mL CV) using SPSFF under various flow rates.
Figure 22:
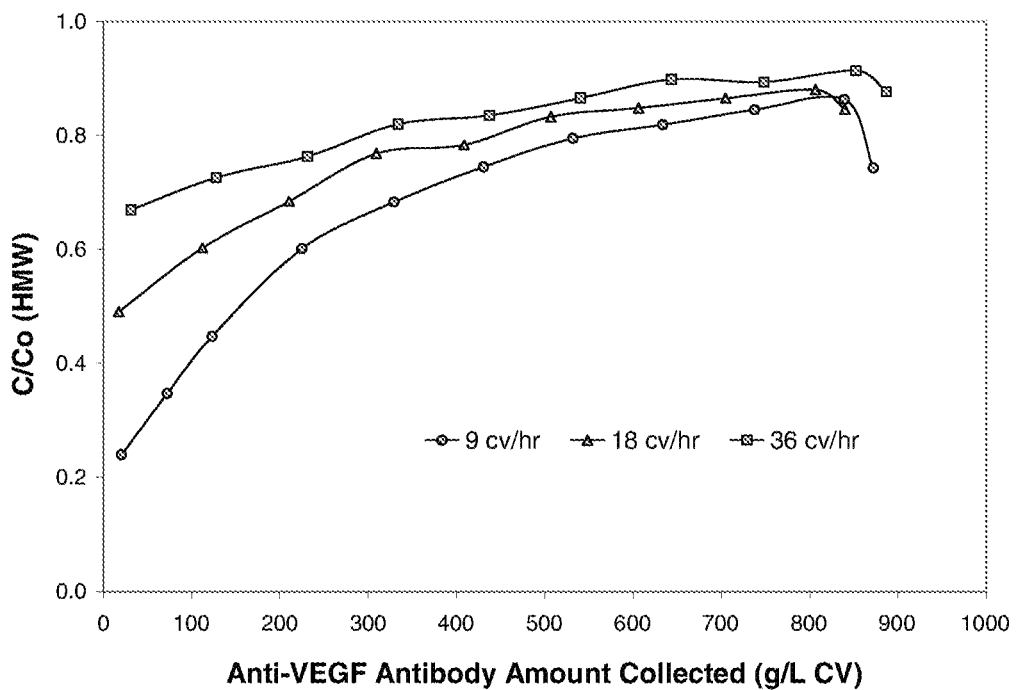
FIG. 22 shows $C/C_0$ (HMW concentration) with varying amount of the product comprising anti-VEGF antibody collected (g/L CV) using SPSFF under various flow rates.

The effects of various flow rates (9 CV/hr, 18 CV/hr, and 36 CV/hr) on CHOP, DNA and HMW removals for SPSFF with varying amount of the product loaded up to 1000 g/L CV were evaluated at pH 5.5 and 5 mS/cm. As shown in FIG. 20, the CHOP removal was not significantly affected by the flow rates tested. However, as shown in FIGS. 21 and 22, the DNA and HMW removals were affected by the flow rates tested.

Purification of Anti-VEGF Antibody Using Poros HS50

Figure 23:
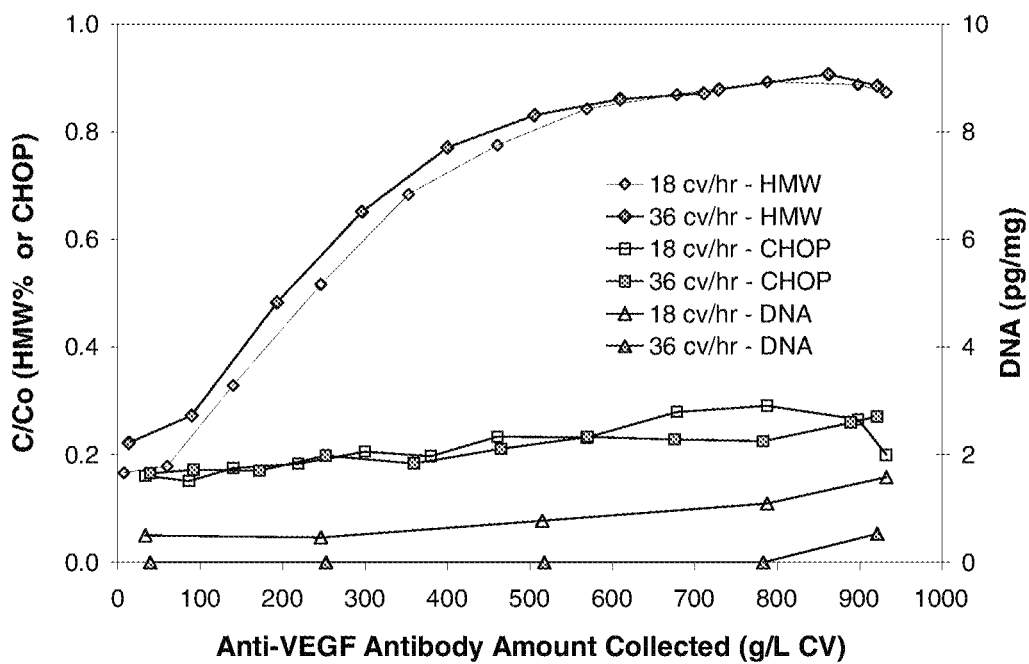
FIG. 23 shows $C/C_0$ (HMW concentration (%)), $C/C_0$ (CHOP concentration (ppm)), and the amount of DNA (pg/mg) with varying amount of the product comprising anti-VEGF antibody collected (g/L CV) using POROS® HS50 under various flow rates.

The effects of various flow rates (18 CV/hr and 36 CV/hr) on CHOP, DNA and HMW removals for Poros HS50 with varying amount of the product loaded up to 1000 g/L CV were evaluated at pH 5.5 and 5 mS/cm. As shown in FIG. 23, the HMW, CHOP and DNA removals were not significantly affected by the flow rates tested.

Figure 24:
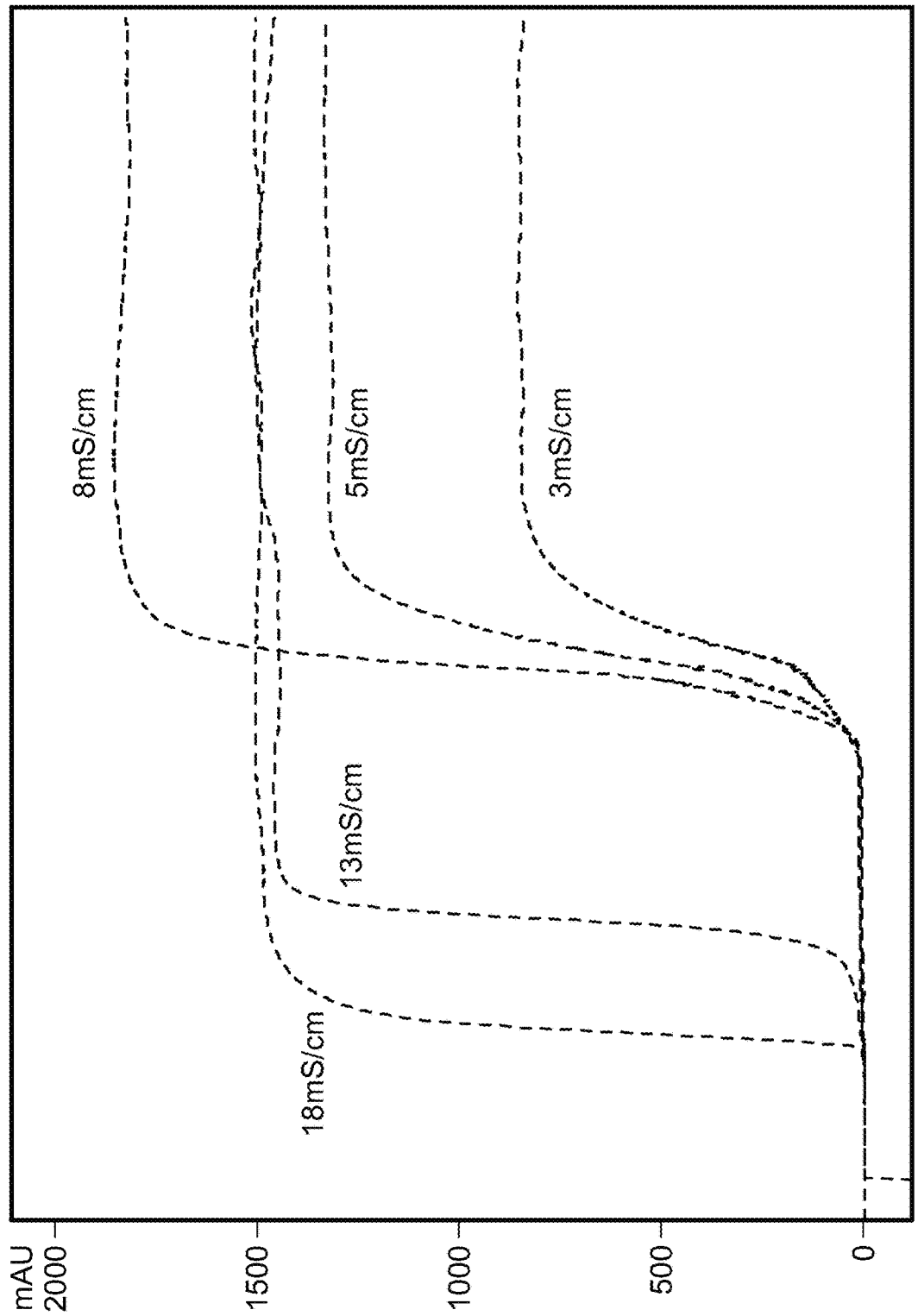
FIG. 24 shows the chromatograms using POROS® HS50 under various loading conductivities for the purification of anti-VEGF antibody.

The Mab binding ability of POROS® HS50 was evaluated at various loading conductivities (3 mS/cm, 5 mS/cm, 8 mS/cm, 13 mS/cm, and 18 mS/cm) at pH 5.5 and 18 CV/hr using varying amount of the product loaded up to 1000 mg/mL CV. As shown in FIG. 24, a higher loading conductivity correlated with a lower Mab binding capacity.

Figure 25A:
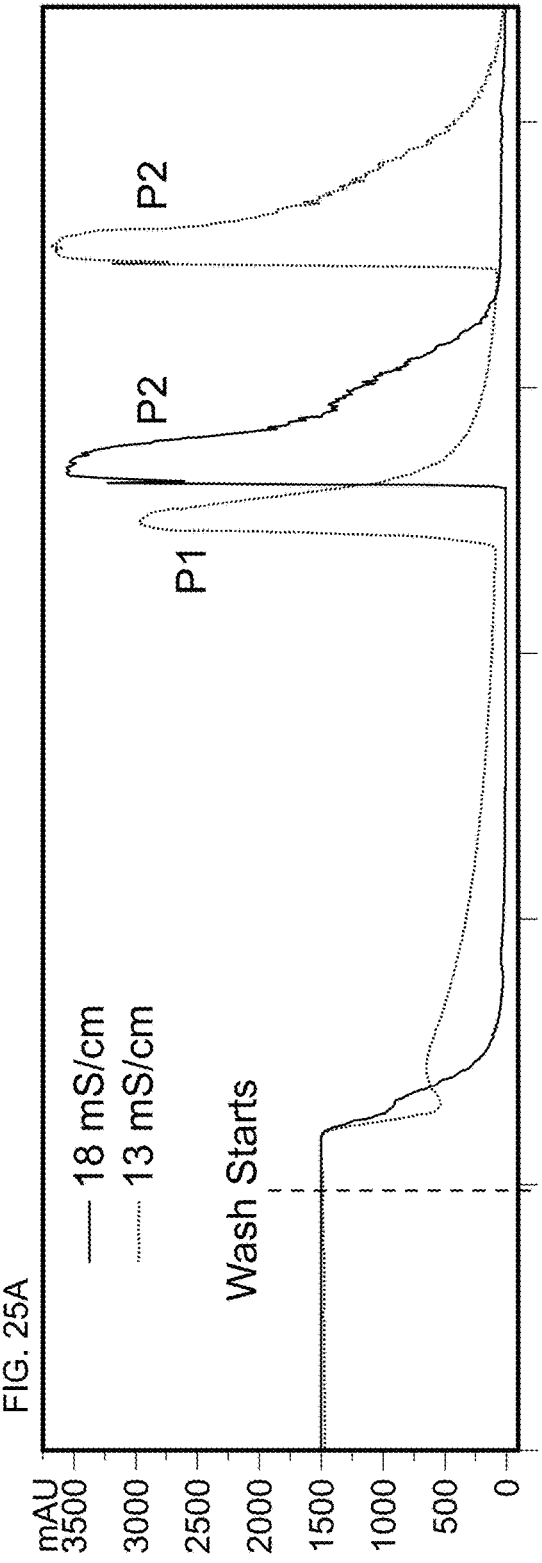
FIG. 25A-B show the chromatograms of the eluate from the elution (P1 peak) and the eluate from the cleaning (P2 peak) using POROS® HS50 loaded with the product comprising anti-VEGF antibody under various loading conductivities.
Figure 25B:
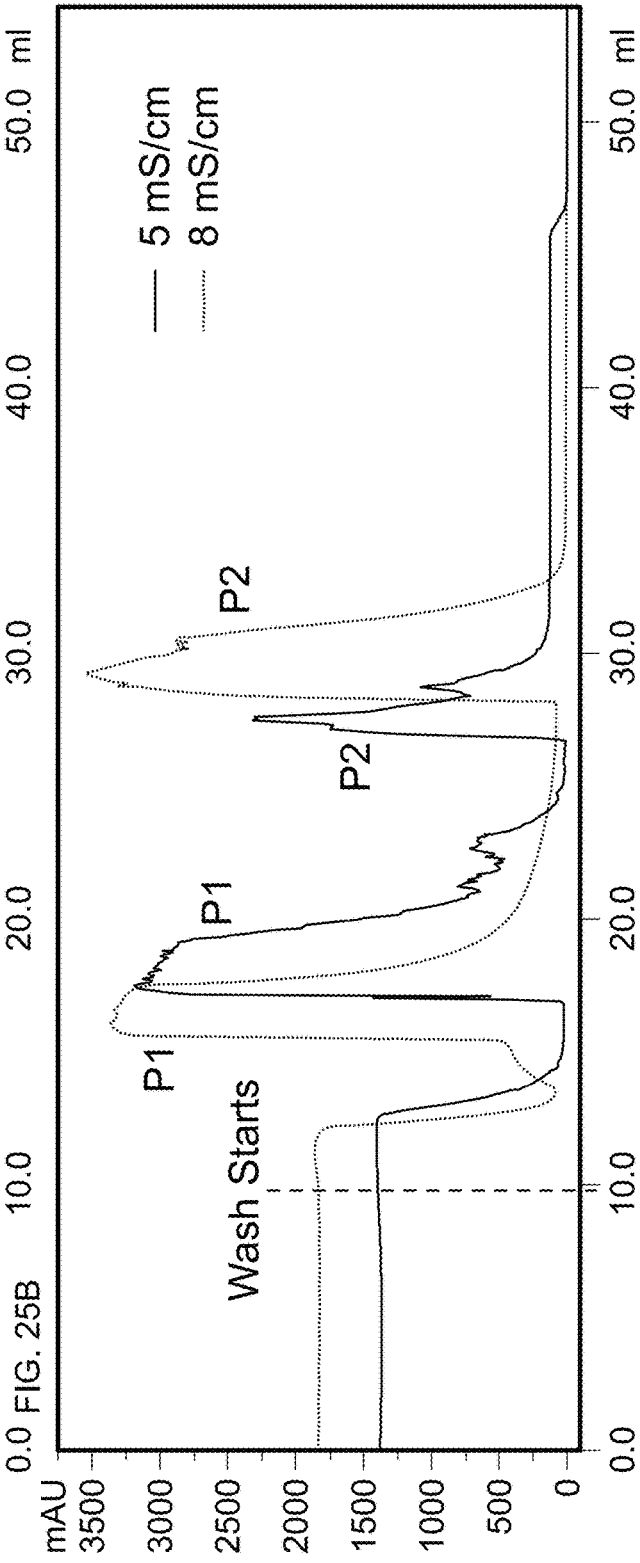

The chromatograms of POROS® HS50 were run under various loading conductivities (5 mS/cm, 8 mS/cm, 13 mS/cm, and 18 mS/cm) at pH 5.5. P1 shows the elution peak with 350 mM NaAC and P2 shows the cleaning peak with 0.5 N NaOH. See FIG. 25. As shown in FIG. 25, there was typical binding to POROS® HS50 under the loading conductivities of 5 mS/cm and 8 mS/cm. Further, there was partial binding at 13 mS/cm. See FIG. 25. At 18 mS/cm, there was typical flow through. See FIG. 25.

Figure 26:
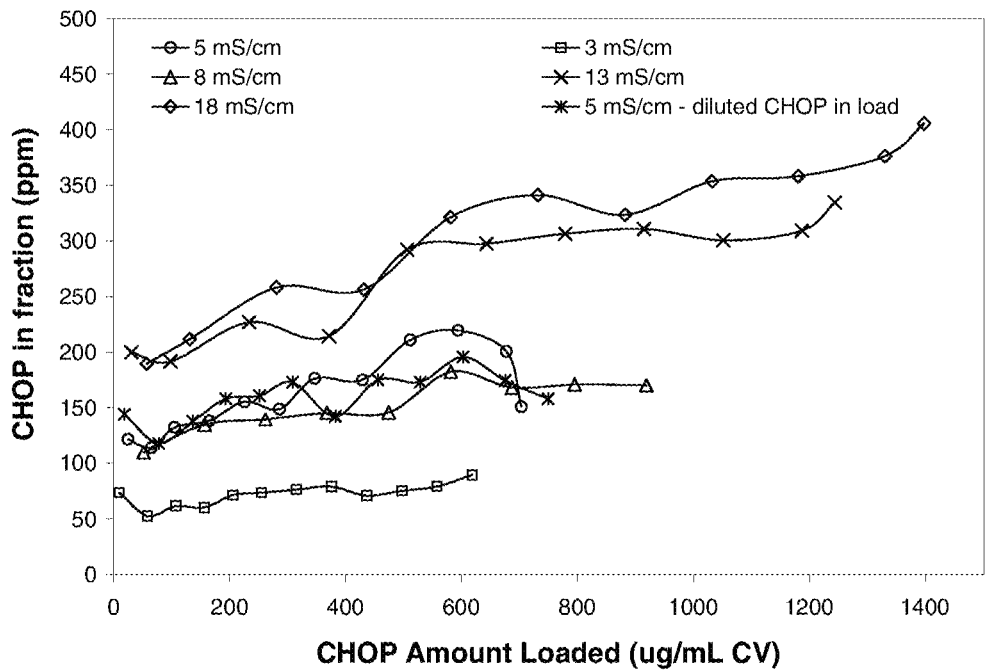
FIG. 26 shows the amount of CHOP in fraction (ppm) with varying amount of CHOP loaded (ug/mL CV) using POROS® HS50 under various loading conductivities for the purification of anti-VEGF antibody.

The ability of POROS® HS50 in CHOP removal was examined at pH 5.5 under various conductivity conditions (3 mS/cm, 5 mS/cm, 5 mS/cm and loaded with ~2 fold diluted CHOP, 8 mS/cm, 13 mS/cm, and 18 mS/cm) with varying amount of the product loaded up to 1000 mg/mL CV at 18 CV/hr. As shown in FIG. 26, the CHOP removal was more effective under lower loading conductivity.

Figure 27:
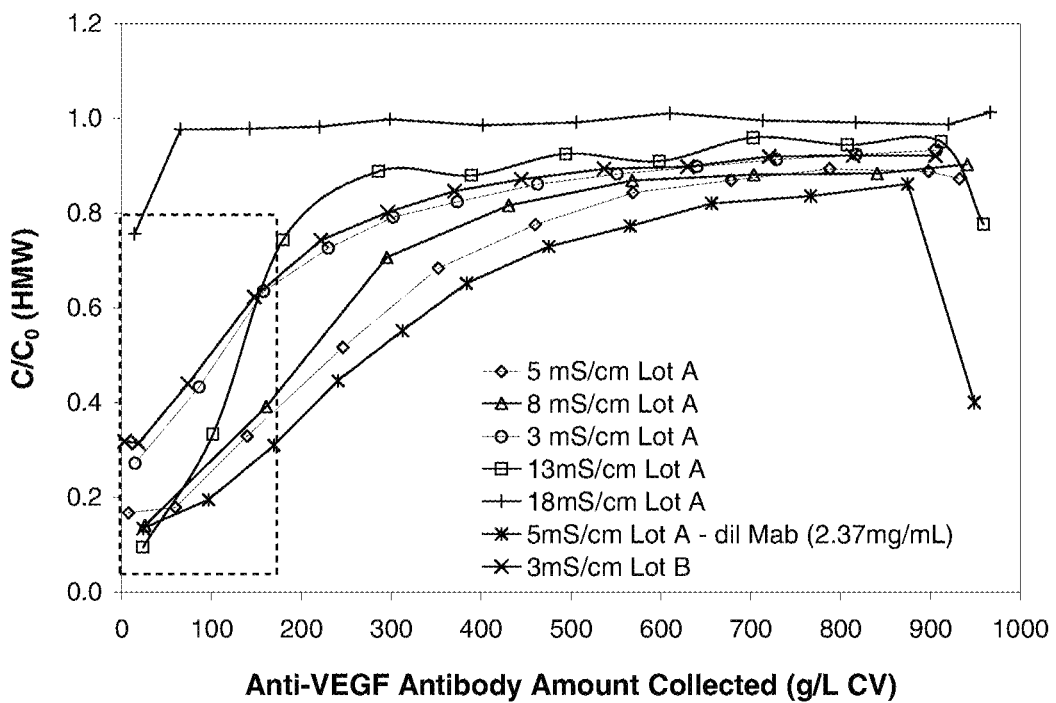
FIG. 27 shows $C/C_0$ (HMW concentration) with varying amount of the product comprising anti-VEGF antibody collected (mg/mL CV) using POROS® HS50 under various loading conductivities.

The ability of POROS® HS50 in HMW removal was evaluated at pH 5.5 under various loading conductivities (3 mS/cm, 5 mS/cm, 5 mS/cm and ~2 fold diluted Mab at 2.37 mg/ml, 8 mS/cm, 13 mS/cm, and 18 mS/cm) with varying amount of the product loaded up to 1000 g/L CV and 18 CV/hr. As shown in FIG. 27, at 3 mS/cm, there was a lower amount of HMW bound to POROS® HS50 at the beginning of the process. At 13 mS/cm, a higher amount of HMW was bound to POROS® HS50 at the beginning of the process and the amount of HMW bound declined over time. See FIG. 27.

Figure 28A:
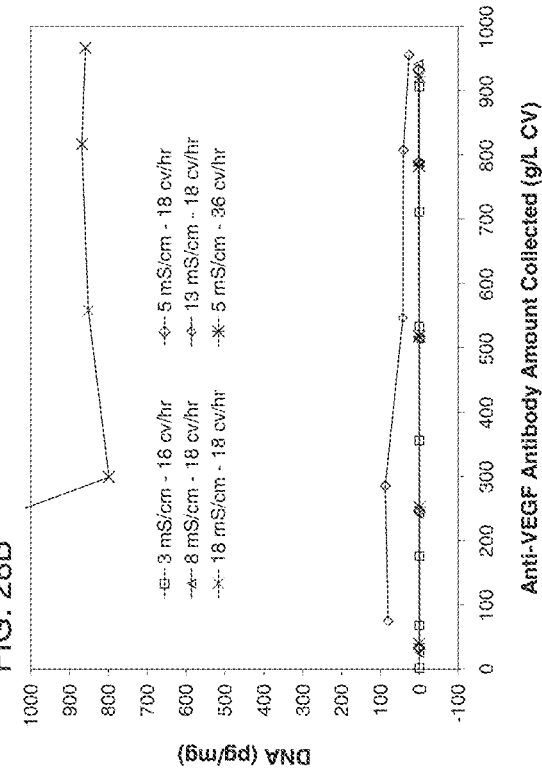
FIGS. 28A-28B show the amount of DNA (pg/ml) with varying amount of the product comprising anti-VEGF antibody collected (g/L CV) under various loading conductivities and various flow rates (different amount of DNA in the load (pg/mg) for different loading conductivity).
Figure 28B:
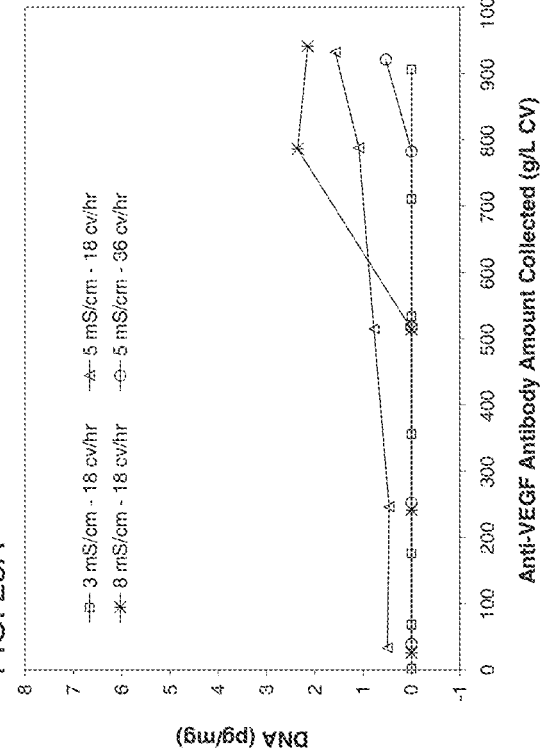

The ability of POROS® HS50 in DNA removal with varying amount of the product loaded up to 1000 mg/mL CV was evaluated under various loading conductivities and flow rates (3 mS/cm and 18 CV/hr, 5 mS/cm and 18 CV/hr, 5 mS/cm and 36 CV/hr, 8 mS/cm and 18 CV/hr, 13 mS/cm and 18 CV/hr, and 18 mS/cm and 18 CV/hr) at pH 5.5. The amounts of DNA in the load were about 1000 pg/mg, 1000 pg/mg, 7000 pg/mg, 16821 pg/mg, and 18566 pg/mg for the loading conductivity conditions of 3 mS/cm, 5 mS/cm, 8 mS/cm, 13 mS/cm, and 18 mS/cm, respectively. As shown in FIGS. 28(A) and (B), POROS® HS50 was able to bind DNA under the loading conductivities tested.

Figure 29:
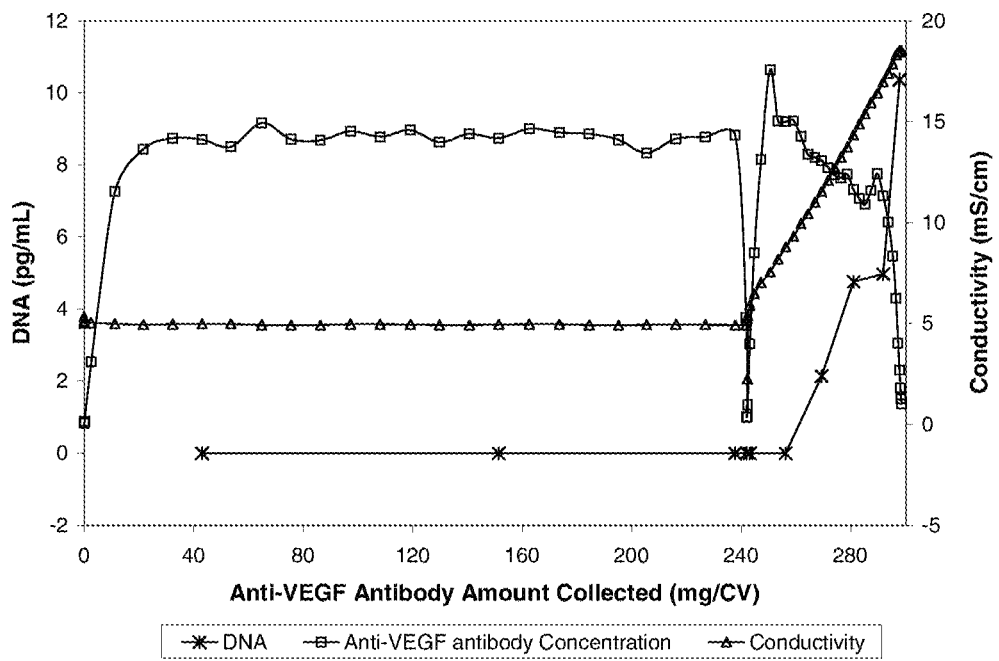
FIG. 29 shows the amount of DNA (pg/mL) and antibody concentration with varying amount of the product comprising anti-VEGF antibody collected (mg/mL CV) using POROS® HS50 eluted with a linear salt gradient elution.

The ability of POROS® HS50 to bind DNA with the product loaded at 300 mg/mL CV was also evaluated at pH 5.5 with the gradient elution. As shown in FIG. 29, DNA was bound to the column at pH 5.5 and 5 mS/cm and eluted off the column during the linear salt gradient elution.

The ability of POROS® HS50 (1.88 mL resin) to remove gentamicin was evaluated at pH 5.5, 5 mS/cm, and 18 CV/hr with varying amount of the product loaded up to about 990 g/L CV. As shown in Table 4, POROS® HS50 was able to remove gentamicin in the overloaded process.

TABLE 4

| Sample ID | Product Collected (g/L) | Gentamicin (pg/mL) | Gentamicin (pg/mg) |
| --- | --- | --- | --- |
| Load | — | 32.875 | 7.15 |
| F5 | 65 | <0.37 | <0.08 |
| F15 | 331 | <0.37 | <0.08 |
| F30 | 727 | <0.37 | <0.08 |
| F35 | 860 | <0.37 | <0.08 |
| Eluate | — | 321.25 | 20 |

The ability of POROS® HS50 (1.88 mL resin) to remove Protein A was evaluated at pH 5.5, 5 mS/cm, and 18 CV/hr with varying amount of the product loaded up to about 990 g/L CV. As shown in Table 5, POROS® HS50 was able to remove Protein A leachate in the overloaded process. The Protein A broke through from the column between 727 and 860 g collected/L CV. See Table 5.

TABLE 5

| Sample ID | Product Collected (g/L) | Protein A (ng/mL) | Protein A (ng/mg) |
| --- | --- | --- | --- |
| Load | — | 22.17 | 4.82 |
| F5 | 65 | <9.8 | <2.18 |
| F15 | 331 | <9.8 | <2.17 |
| F22 | 517 | <9.8 | <2.18 |
| F30 | 727 | <9.8 | <2.20 |
| F35 | 860 | 13.53 | 2.99 |
| Eluate | — | 1324.35 | 82.41 |

Figure 30:
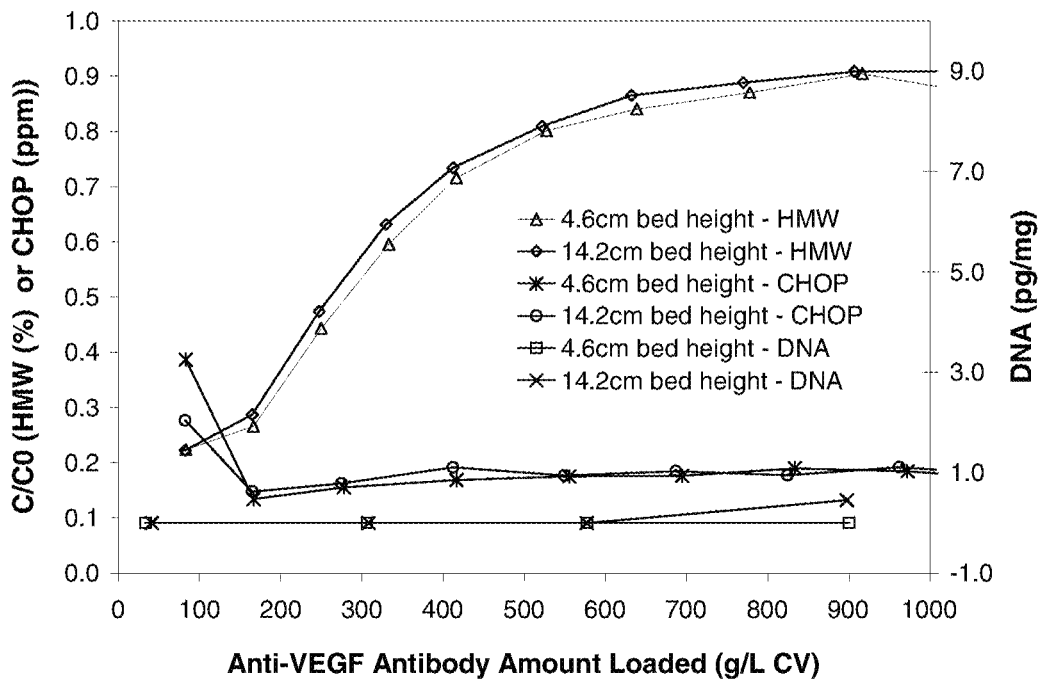
FIG. 30 shows $C/C_0$ (HMW concentration (%)), $C/C_0$ (CHOP concentration (ppm)), and the amount of DNA (pg/mg) with varying amount of the product comprising anti-VEGF antibody loaded (g/L CV) using POROS® HS50 with the bed height of 4.6 cm or 14.2 cm.

The ability of POROS® HS50 to remove HMW, CHOP and DNA under different column bed heights (4.6 cm bed height and 14.2 cm bed height) was evaluated at pH 5.5, 5 mS/cm, and 18 CV/hr with varying amount of the product loaded up to 1000 mg/mL CV. As shown in FIG. 30, the column bed heights tested (4.6 cm and 14.2 cm) had no significant effects on HMW, CHOP, or DNA removal. Further, the column bed heights of 4.6 cm and 14.2 cm kept the same residence time (3 minutes).

The distribution of charged variants in the elution fractions from the POROS® HS50 column (1.88 mL) was evaluated at pH 5.5, 5 mS/cm, and 18 CV/hr, with varying amount of the product loaded up to 1000 g/L CV. The basic variants were treated with CPB (Carboxypeptidase B) prior to the performing the charged variant analysis. As shown in Table 6, the distribution of charged variants (the acidic and basic variants) and main variants in the final pool was not substantially changed. There was a higher percentage of acidic variant in the flow through at the low loading amount. See Table 6. POROS® HS50 was able to bind to some basic variant. See Table 6.

TABLE 6

| | Acidic (%) | Main (%) | Basic (%) |
| --- | --- | --- | --- |
| Load | 28.54 | 60.91 | 10.54 |
| Collected Mab per CV in fraction (g/L cv) | | | |
| 65 | 32.87 | 62.76 | 4.37 |
| 331 | 29.78 | 59.21 | 11.01 |
| 727 | 29.53 | 58.05 | 12.42 |
| 833 | 29.62 | 57.6 | 12.78 |
| Elute Pool (60.8 mg/mL CV) | 8.36 | 32.42 | 59.22 |

Example 3—Purification of Polypeptides Using Mixed Mode Chromatography

This example describes a mixed mode chromatography process for purifying anti-VEGF antibody, anti-CD11a antibody, and anti-CD20 antibody.

Materials and Methods

Purification Methods

The filtered and equilibrated protein pools were prepared as described in Example 1 for subsequent mixed mode chromatography. Pools were adjusted to the pH of 5 to 8.5 with 1.5 M Tris base or 2 N glacial acetic acid. Chloride concentrations were adjusted to 0 mM to 250 mM with the addition of 3M NaCl. Specific mixed mode chromatography conditions were performed as indicated in the Experimental Procedures and Results section below.

Experimental Procedures and Results

The performance of the mixed-mode resin, e.g., CAPTO™ ADHERE, was evaluated using multiple antibodies, anti-VEGF antibody (70 mg/ml resin), anti-CD11a antibody (90 mg/ml resin), and anti-CD20 antibody (90 mg/ml resin) under various pHs and salt conditions in a high throughput screening experiment. The amount of CHOP (ppm) and % HMW in the filtered and equilibrated protein A purified pools was 497 and 7.6 (for anti-VEGF antibody), 820 and 6.4 (for anti-CD11a antibody), and 4720 and 3.5 (for anti-CD20 antibody). FIGS. 31, 32, and 33 show the results for the Mab recovery, the binding of HMW to the resin, and the binding of CHOP to the resin, respectively, under various pHs and salt conditions. As shown in FIG. 31, increasing the pH and conductivity increased the binding of Mab to CAPTO™ ADHERE resin for anti-VEGF antibody and anti-CD20 antibody. The pH had significant effects on the ability of CAPTO™ ADHERE to bind anti-CD11a antibody. See FIG. 31. Increasing the pH increased the percentage of HMW species bound to the CAPTO™ ADHERE resin for anti-VEGF antibody, anti-CD11a antibody, and anti-CD20 antibody. See FIG. 32. The pH had more significant effects than the conductivity on the ability of CAPTO™ ADHERE to bind HMWs. See FIG. 32. CAPTO™ ADHERE resin was able to bind CHOP under the broader pH and conductivity ranges. As shown in FIG. 33, more than 80% of CHOP was bound to the resin for the majority of the contour plots for anti-VEGF antibody, anti-CD11a antibody, and anti-CD20 antibody.

The performance of CAPTO™ ADHERE in the high throughput screening experiment and in the column chromatography for the purification of anti-VEGF antibody is summarized in Table 7. In general, the observations made in the high throughput experiment correlated with the results obtained from the column chromatography experiment.

TABLE 7

| pH | Condo | % Mab in FT | | % HMW in FT | | % HMW Bound | | CHOP (ppm) in FT | | % CHOP Bound | |
|---|---|---|---|---|---|---|---|---|---|---|---|
| | | Well Plate | Column | Well Plate | Column | Well Plate | Column | Well Plate | Column | Well Plate | Column |
| 5.0 | 5.0 | 93 | 100 | 5.9 | 5.1 | −13.8 | 7.8 | 23.0 | 36.0 | 93.4 | 93.0 |
| 7.0 | 5.0 | 67 | 76 | 4.4 | 4.6 | 35.4 | 37.4 | 10.4 | 12.8 | 97.4 | 96.9 |
| 8.0 | 5.0 | 27 | 28 | 1.2 | 1.7 | 83.3 | 77.9 | 17.3 | 31.3 | 95.3 | 92.7 |
| 8.0 | 19.4 | 23 | 21 | 1.9 | 6.9 | 71.0 | 40.1 | 71.1 | 154.9 | 79.6 | 70.9 |
| 8.5 | 5.0 | 13 | 22 | 0.9 | 2.3 | 86.0 | 73.9 | 23.7 | 85.0 | 93.4 | 83.9 |

The ability of CAPTO™ ADHERE to remove CHOP and HMW was also examined in the column chromatography for the purification of anti-CD11a at pH 5.5 and 5 mS/cm. CAPTO™ ADHERE resin was able to reduce CHOP levels to below 20 ppm when the product was loaded at about 700 mg/mL resin; however, CAPTO™ ADHERE was not able to reduce % HMW. Data not shown.

Example 4—Purification of Anti-CD11a Antibody Using a Combination of Overloaded Cation Exchange Chromatography and Standard Anion Exchange Chromatography This example describes a process using a combination of overloaded cation exchange chromatography and standard anion exchange chromatography for purifying a recombinant humanized CD11a antibody.

Materials and Methods

The cell culture fluid containing monoclonal antibody produced in Chinese hamster ovary cells was processed by continuous centrifuge to remove cellular debris, and further clarified through filtration with depth filters and 0.2 um filter. The anti-CD11a antibody was purified by either a) development run overloaded cation exchange: (i) protein A purification (PROSEP® vA), (ii) cation exchange purification (CEX) (POROS® HS50, in overloaded mode), and (ii) anion exchange (AEX) (QSFF), or (b) commercial process (i) protein A purification (PROSEP® vA), (ii) CEX (SPSFF), and (ii) AEX (QSFF). The running conditions are listed in Table 8.

TABLE 8

| | Commercial Process | | | Development Run Overloaded CEX | | |
|---|---|---|---|---|---|---|
| Purification Step | Operating Mode | Operating Condition | Load Density (g/L CV) | Operating Mode | Operating Condition | Load Density (g/L CV) |
| Protein A | B/E | STD | 8-20 | B/E | STD | 8-20 |
| CEX | B/E | pH 5.5, load-4.7 mS/cm, elution-13.25 mS/cm | 15-40 | Overloaded | pH 5.5, 5 mS/cm | 600 |
| AEX | FT | pH 8.0, 6.9 mS/cm | 15-70 | FT | pH 8.0, 5 mS/cm | 70 |

Experimental Procedures and Results

The performance of the process combining the overloaded CEX with the AEX was evaluated with respect to the CHOP removal and Mab recovery. The results are summarized in Table 9.

TABLE 9

| | Commercial Process | | Development Run Overloaded CEX | | |
|---|---|---|---|---|---|
| Purification Step | CHOP (ng/mg) | Monomer (%) | CHOP (ng/mg) | Monomer (%) | Yield (%) |
| Protein A | 677-939 | 94.7-95.9 | 995 | 93.4 | |
| CEX | 116-183 | 99.3-99.8 | 158 | 99.7 | 90 |
| AEX | <22.2 | 99.7-99.8 | 2 | 99.7 | 95 |
| Bulk | <1.48 | 99.6-99.7 | | | |

The ability of POROS® HS50 and QSFF to remove HMW, CHOP, gentamicin, DNA, and leached Protein A was evaluated under two conditions: (a) POROS® HS50 at pH 5.5, 3.5 mS/cm and QSFF at pH 8.0, 3.5 mS/cm; and (b) POROS® HS 50 at pH 5.5, 5.0 mS/cm and QSFF at pH 8.0, 5.0 mS/cm. The results for conditions (a) and (b) are summarized in Table 10 and Table 11, respectively. Gentamicin, DNA, and leached Protein A were removed to below detection limits There was better CHOP removal under condition (a) than under condition (b). There was better HMW removal under condition (b) than under condition (a). The product yield was at least 90% for each chromatography step.

TABLE 10

| Step | HMV (%) Load | HMV (%) Pool | CHOP (ppm) Load | CHOP (ppm) Pool | Genamicin (ng/mg) Load | Genamicin (ng/mg) Pool | DNA (ng/mg) Load | DNA (ng/mg) Pool | Leached ProA (ng/mg) Load | Leached ProA (ng/mg) Pool |
|---|---|---|---|---|---|---|---|---|---|---|
| POROS HS50 | 6.4 | 1.42 | 1168 | 55 | 9.1 | <0.1 | 0.3 | 0.3 | 25 | <2 |
| QSFF | 1.42 | 1.41 | 55 | 2 | <0.1 | <0.1 | 0.5 | 0 | <2 | <2 |

TABLE 11

| Step | HMV (%) Load | HMV (%) Pool | CHOP (ppm) Load | CHOP (ppm) Pool | Gentamicin (ng/mg) Load | Gentamicin (ng/mg) Pool | DNA (ng/mg) Load | DNA (ng/mg) Pool | Leached ProA (ng/mg) Load | Leached ProA (ng/mg) Pool |
|---|---|---|---|---|---|---|---|---|---|---|
| POROS HS50 | 6.59 | 0.28 | 664 | 133 | 5 | <0.1 | 0.3 | <LTR | 21 | <2 |
| QSFF | 0.28 | 0.3 | 133 | 2 | <0.1 | <0.1 | <LTR | <LTR | <2 | <2 |

Example 5—Purification Using a Combination of Overloaded Cation Exchange Chromatography and Mixed Mode Chromatography This example describes a process using a combination of overloaded cation exchange chromatography and mixed mode chromatography for purifying an anti-CD11a antibody and anti-CD20 antibody.

Materials and Methods

The filtered and equilibrated protein pools were prepared as described in Example 1 for subsequent cation exchange chromatography and/or mixed mode chromatography. Specific cation exchange chromatography and/or mixed mode chromatography conditions were performed as indicated in the Experimental Procedures and Results section below.

Experimental Procedures and Results

Anti-CD11a Purification

Experiment 1—The filtered and equilibrated product described above was purified using an overloaded POROS® HS50 column and a CAPTO™ ADHERE column with approximately ~600 g/L CV of product loaded for POROS® HS50 and about ~100 g/L CV for CAPTO™ ADHERE at pH 5.5, 5 mS/cm, and 100 cm/hr. The experiment was performed in two different sequences: a) Sequence A: (i) POROS® HS50 column (0.66 cm×5 cm) and (ii) CAPTO™ ADHERE (1.5 cm×20 cm) or b) Sequence B (i) CAPTO™ ADHERE (0.66 cm×20 cm) and (ii) POROS® HS50 column (0.66 cm×5 cm). For Sequence A, the loading densities for POROS® HS50 column and CAPTO™ ADHERE column were 600 mg/mL resin and 106 mg/mL resin, respectively. For Sequence B, the loading densities for CAPTO™ ADHERE column and POROS® HS50 column were 100 mg/mL resin and 569 mg/mL resin, respectively.

The results on impurity removals are summarized in Table 12 for Sequence A and Table 13 Sequence B. The product recovery yields and the results on impurity removals for both of the procedures were met commercial process purity and yield.

TABLE 12

Sequence A.

| Step Description | Step Recovery | CHOP Conc (ppm) Load | CHOP Conc (ppm) Pool | % HMW Load | % HMW Pool |
|---|---|---|---|---|---|
| Poros HS | 96 | 659 | 110 | 6.4 | 0.5 |
| Capto Adhere | 100 | 110 | 3 | 0.5 | 0.4 |

| Step Description | DNA (pg/mg) Load | DNA (pg/mg) Pool | Leached ProA (ppm) Load | Leached ProA (ppm) Pool | Gentamicin (ppm) Load | Gentamicin (ppm) Pool |
|---|---|---|---|---|---|---|
| Poros HS | 137.6 | <2 | 27 | <2 | 46.8 | <1 |
| Capto Adhere | <2 | <2 | <2 | <2 | <1 | <1 |

TABLE 13

Sequence B.

| Step Description | Step Recovery | CHOP Conc (ppm) Load | CHOP Conc (ppm) Pool | % HMW Load | % HMW Pool |
|---|---|---|---|---|---|
| Capto Adhere | 102 | 659 | 16 | 6.4 | 6.2 |
| Poros HS | 90 | 16 | 2 | 6.2 | 0.3 |

| Step Description | DNA (pg/mg) Load | DNA (pg/mg) Pool | Leached ProA (ppm) Load | Leached ProA (ppm) Pool | Gentamicin (ppm) Load | Gentamicin (ppm) Pool |
|---|---|---|---|---|---|---|
| Capto Adhere | 137.6 | 1.1 | 27 | <2 | 46.8 | <1 |
| Poros HS | 1.1 | <2 | <2 | <2 | <1 | <1 |

Experiment 2—The filtered and equilibrated product described above was continuously purified using CAPTO™ ADHERE (0.66 cm×5.2 cm) then POROS® HS50 column (0.66 cm×4.8 cm) with approximately 566 g/L CV of product loaded for POROS® HS50 and about 614 g/L CV for CAPTO™ ADHERE at pH 5.5, 5 mS/cm, and 100 cm/hr under the conditions recited in the table below.

TABLE 14

Chromatographic conditions used in the continuous processing of anti-CD11a antibody.

| Phase | Buffer/Solution | Process Parameter |
|---|---|---|
| Equilibration | 77 mM NaAc, pH 5.5, 5 mS/cm | 5 CV of Poros HS50 or Capto Adhere resin |
| Load | Conditioned Protein A pool (pH 5.5 & 5 mS/cm) | Load up to 614 g/L Poros HS50 resin; start to pooling at OD280 ≥0.5; end pooling at OD280 ≤0.5 |
| Wash | 77 mM NaAc, pH 5.5, 5 mS/cm | ≥2 CV of Poros HS50 or Capto Adhere column |
| Strip 1 | 2M NaCl | 5 CV of Poros HS50 or Capto Adhere resin |
| Strip 2 | 0.15M acetate buffer, pH 2.8 | 5 CV of Poros HS50 or Capto Adhere resin |
| Sanitization | 0.5N NaOH | 4 CV of Poros HS50 or Capto Adhere column |
| Storage | 0.1N NaOH | 3 CV of Poros HS50 or Capto Adhere resin |

Figure 34:
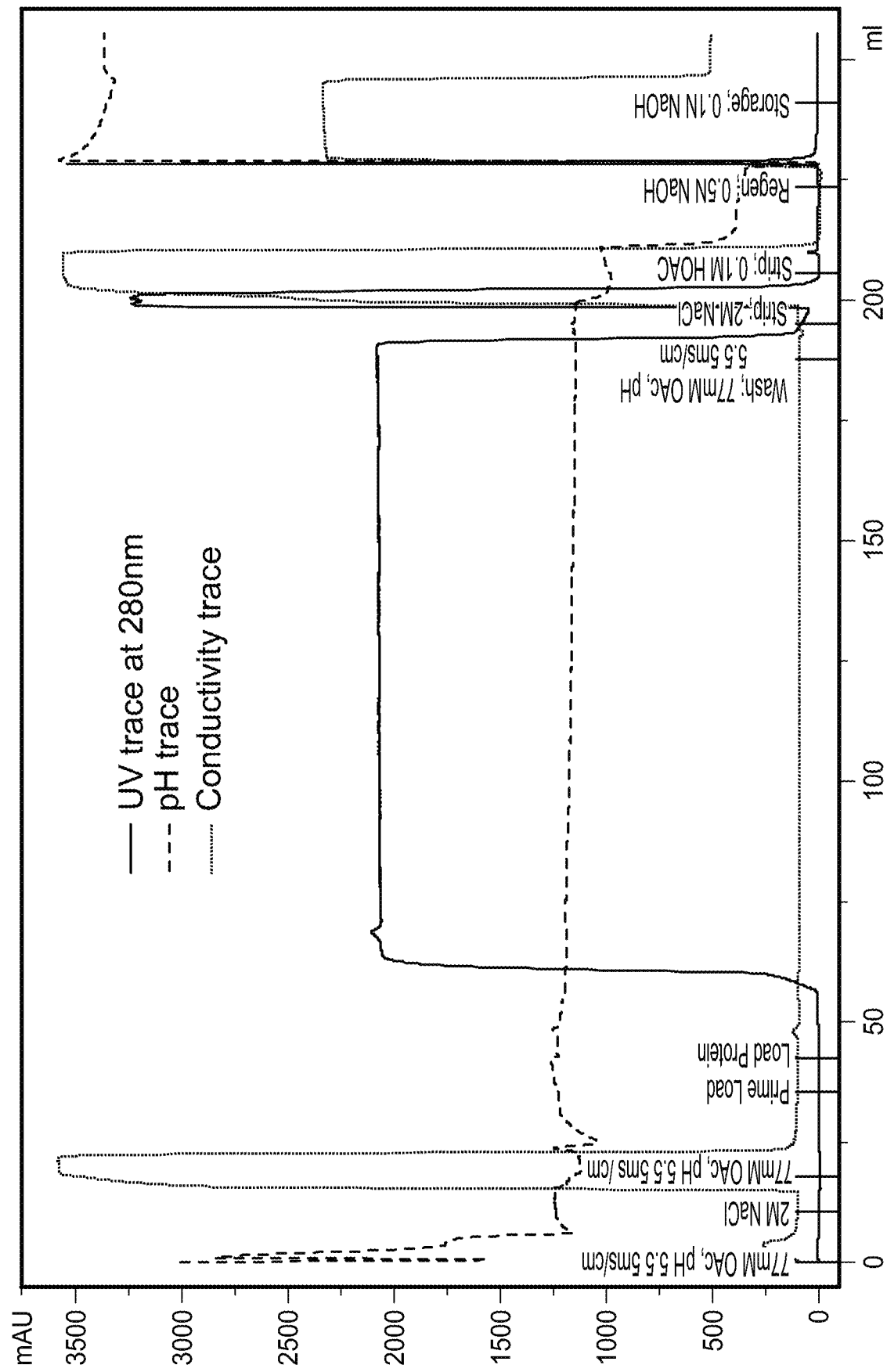
FIG. 34 shows the chromatograms using the coupled CAPTO™ ADHERE column and POROS® HS50 column for the purification of anti-CD11a antibody.

The chromatogram results for the continuous process are shown in FIG. 34. The continuous processing resulted in the Mab recovery yield of about 90%. Data not shown. In addition, there was 617 ppm CHOP in the load but only 3.4 ppm in the pool, there was 6.37% HMW in the load but only 0.6% in the pool (90% HMW removal), and DNA, Protein A leachate, and gentamicin was below detection limits.

Anti-CD20 Purification

Experiment 1—The product pool from Protein A chromatography was purified using POROS® HS50 column (0.66 cm×5 cm) with approximately 600 g/L CV of product loaded and CAPTO™ ADHERE (0.66 cm×8 cm) with approximately 316 g/L CV for CAPTO™ ADHERE at pH 5.5, 5 mS/cm, and 100 cm/hr.

Results are provided in Table 15 below. The overloaded POROS® HS resulted in ~50% reduction in % HMW and 98% CHOP reduction. POROS® HS50 was the best resin compared to SE Hicap, SPFF, SPXL and CAPTO S™ in reducing % HMW (data not shown). CAPTO™ ADHERE resulted in no additional % HMW reduction, but a 99% CHOP reduction (CHOP break through was observed).

TABLE 15

| Resin | Step Recovery | % HMW Load | % HMW Pool | CHOP (ppm) Load | CHOP (ppm) Pool |
|---|---|---|---|---|---|
| Poros 50 HS | 90 | 3.8 | 1.7 | 3812 | 72 |
| Capto Adhere | 100 | 3.5 | 3.4 | 4722 | 49 |

Experiment 2—The filtered and equilibrated product described above was continuously purified using an overloaded POROS® HS50 column (0.66 cm×4.8 cm) and a CAPTO™ ADHERE (0.66 cm×7 cm) column with approximately ~600 g/L CV of product loaded for POROS® HS50 and about ~340 g/L CV for CAPTO™ ADHERE at pH 5.5, 5 mS/cm, and 100 cm/hr. The experiment was performed in two different sequences: a) Sequence A: (i) POROS® HS50 column and (ii) CAPTO™ ADHERE or b) Sequence B (i) CAPTO™ ADHERE and (ii) POROS® HS50 column under the conditions recited in the table below.

TABLE 16

Chromatographic conditions used in continuous processing of anti-CD20 antibody.

| Phase | Buffer/Solution | Process Parameter |
|---|---|---|
| Equilibration | 77 mM NaAc, pH 5.5, 5 mS/cm | 5 CV of Poros HS50 or Capto Adhere resin Load up to 600 g/L |
| Load | Conditioned Protein A pool at pH 5.5 & 5 mS/cm | Poros HS50 resin (it equals to 340 g/L Capto Adhere resin); start to pooling at OD280 ≥0.5; end pooling at OD280 ≤0.5 |
| Wash | ~80 mM NaAc, pH 5.5, 5 mS/cm | ≥2 CV of Poros HS50 or Capto Adhere column |
| Strip 1 | 2M NaCl | 5 CV of Poros HS50 or Capto Adhere resin |
| Strip 2 | 0.15M acetate buffer, pH 2.8 | 5 CV of Poros HS50 or Capto Adhere resin |
| Sanitization | 0.5N NaOH | 4 CV of Poros HS50 or Capto Adhere column |
| Storage | 0.1N NaOH | 3 CV of Poros HS50 or Capto Adhere resin |

Results are provided in Table 17 below. The continuous processing resulted in the Mab recovery yield of about 90% (POROS® HS50 then CAPTO™ ADHERE) and about 87% (CAPTO™ ADHERE then POROS® HS50). The overloaded POROS® HS resulted in ~59% reduction in % HMW, CHOP was reduced to less than 10 ppm, and DNA, Protein A leachate, gentamicin were below detectable limits.

TABLE 17

| Step Order | Step Recovery (%) | % HMW Load | % HMW Pool | CHOP Conc (ppm) Load | CHOP Conc (ppm) Pool |
|---|---|---|---|---|---|
| Poros HS/ Capto Adhere | 92 | 3.7 | 1.5 | 5607 | 5 |
| Capto Adhere/ Poros HS | 87 | 3.7 | 1.5 | 4797 | 6 |

What is claimed is:

1. A method for purifying an antibody or immunoadhesin from a composition comprising the antibody or immunoadhesin and at least one contaminant, wherein the method comprises either (i) or (ii):
   (i) sequential steps of (a) loading the composition onto a cation exchange material at a loading density of greater than about 150 g/L of cation exchange material; and (b) loading a composition recovered from the cation exchange material as an unbound fraction onto a mixed mode material; or
   (ii) sequential steps of (a) loading the composition onto a mixed mode material; and (b) loading a composition recovered from mixed mode material as an unbound fraction onto a cation exchange material at a loading density of greater than about 150 g/L of cation exchange material;
   wherein the cation exchange material is resin particles.

2. The method of claim 1, wherein the antibody or immunoadhesin has a pI of between about 6 and about 10.

3. The method of claim 2, wherein the antibody or immunoadhesin has a pI of between about 7 and about 9.

4. The method of claim 1, wherein the antibody or immunoadhesin is an immunoadhesin.

5. The method of claim 1, wherein the antibody or immunoadhesin is an antibody.

6. The method of claim 5, wherein the antibody is a monoclonal antibody.

7. The method of claim 6, wherein the monoclonal antibody is a chimeric antibody, humanized antibody, or human antibody.

8. The method of claim 6, wherein the monoclonal antibody is an IgG monoclonal antibody.

9. The method of claim 5, wherein the antibody is an antigen binding fragment.

10. The method of claim 9, wherein the antigen binding fragment is selected from the group consisting of a Fab fragment, a Fab'fragment, a F(ab')$_2$ fragment, a scFv, a Fv, and a diabody.

11. The method of claim 1, wherein the at least one contaminant is any one or more of Chinese Hamster Ovary Protein (CHOP), leached protein A, DNA, aggregated protein, cell culture media component, gentamicin, and viral contaminant.

12. The method of claim 1, wherein the sequential steps in (i) and/or (ii) are continuous.

13. The method of claim 1, wherein the method is (i).

14. The method of claim 1, wherein the method is (ii).

15. The method of claim 1, wherein the loading density is between about 150 g/L and about 2000 g/L of cation exchange material.

16. The method of claim 15, wherein the density is between about 500 g/L and about 1000 g/L of cation exchange material.

17. The method of claim 1, wherein the cation exchange material comprises a carboxylic acid functional group or a sulfonic acid functional group.

18. The method of claim 17, wherein the functional group is sulphopropyl, sulfoethyl, sulfoisobutyl, or carboxyl.

19. The method of claim 1, wherein the mixed mode material comprises functional groups capable of anionic exchange and hydrophobic interactions.

20. The method of claim 1, wherein the method comprises use of an equilibration buffer, a wash buffer, and/or a loading buffer with the cation exchange material and/or mixed mode material, and the conductivity of the equilibration buffer, the wash buffer, and/or the loading buffer is between about 2 mS/cm to about 25 mS/cm.

21. The method of claim 20, wherein the conductivity of the equilibration buffer, the wash buffer, and/or the loading buffer is between about 3 mS/cm and 8 mS/cm.

22. The method of claim 1, wherein the method comprises use of an equilibration buffer, a wash buffer, and/or a loading buffer with the cation exchange material and/or the mixed mode material, and the pH of the equilibration buffer, the wash buffer, and/or the loading buffer is between about 4.5 and about 6.5.

23. The method of claim 20, wherein the equilibration buffer, the wash buffer, and/or the loading buffer with the cation exchange material and/or the mixed mode material are the same.

24. The method of claim 1 further comprises subjecting the composition comprising the antibody or immunoadhesin to one or more further purification steps either before or after steps (a) and (b).

25. The method of claim 1 further comprising recovering the purified antibody or immunoadhesin.

26. The method of claim 25 further comprising combining the purified antibody or immunoadhesin with a pharmaceutically acceptable carrier.

27. The method of claim 5, wherein the antibody is an anti-CD20 antibody, an anti-CD11a antibody or an anti-VEGF antibody.

* * * * *